(12) United States Patent
Kim et al.

(10) Patent No.: US 10,501,473 B2
(45) Date of Patent: Dec. 10, 2019

(54) FUSED HETEROCYCLIC RING COMPOUNDS AND METHOD OF TREATING RETINAL DISEASE USING SAME

(71) Applicant: THE INDUSTRY & ACADEMIC COOPERATION IN CHUNGNAM NATIONAL UNIVERSITY (IAC), Daejeon (KR)

(72) Inventors: Eunhee Kim, Daejeon (KR); Sung-Eun Yoo, Sejong-si (KR); Nam Sook Kang, Daejeon (KR); Tae-Sung Koo, Daejeon (KR); Min-Young Park, Daejeon (KR); Young-Hoon Kim, Gyeonggi-do (KR); Hyun-Ju Bae, Gyeonggi-do (KR); Jin-Woo Kim, Gyeonggi-do (KR); Tae-Kyu In, Chungcheongnam-do (KR); Choun-Ki Joo, Seoul (KR)

(73) Assignee: THE INDUSTRY & ACADEMIC COOPERATION IN CHUNGNAM NATIONAL UNIVERSITY (IAC) (KR)

( * ) Notice: Subject to any disclaimer, the term of this patent is extended or adjusted under 35 U.S.C. 154(b) by 2 days.

(21) Appl. No.: 15/417,724

(22) Filed: Jan. 27, 2017

(65) Prior Publication Data

US 2017/0152268 A1     Jun. 1, 2017

Related U.S. Application Data

(63) Continuation of application No. PCT/KR2015/007562, filed on Jul. 21, 2015.

(30) Foreign Application Priority Data

Jul. 28, 2014  (KR) .................. 10-2014-0095676

(51) Int. Cl.

| | |
|---|---|
| *A61K 31/5377* | (2006.01) |
| *A61K 31/4353* | (2006.01) |
| *C07D 495/04* | (2006.01) |
| *C07D 413/06* | (2006.01) |
| *A23L 33/16* | (2016.01) |
| *A23L 33/00* | (2016.01) |
| *C07D 209/42* | (2006.01) |
| *C07D 235/24* | (2006.01) |
| *C07D 307/85* | (2006.01) |
| *C07D 333/58* | (2006.01) |
| *C07D 333/60* | (2006.01) |
| *C07D 333/74* | (2006.01) |
| *C07D 409/04* | (2006.01) |
| *C07D 409/06* | (2006.01) |

(52) U.S. Cl.
CPC ............ *C07D 495/04* (2013.01); *A23L 33/16* (2016.08); *A23L 33/40* (2016.08); *C07D 209/42* (2013.01); *C07D 235/24* (2013.01); *C07D 307/85* (2013.01); *C07D 333/58* (2013.01); *C07D 333/60* (2013.01); *C07D 333/74* (2013.01); *C07D 409/04* (2013.01); *C07D 409/06* (2013.01); *C07D 413/06* (2013.01); *A23V 2002/00* (2013.01)

(58) Field of Classification Search
None
See application file for complete search history.

(56) References Cited

FOREIGN PATENT DOCUMENTS

| | | | |
|---|---|---|---|
| JP | 2004-509059 | 3/2004 | |
| JP | 2004-512324 | 4/2004 | |
| JP | 2006-503827 | 2/2006 | |
| JP | 2006-522812 | 10/2006 | |
| JP | 2008-503511 | 2/2008 | |
| JP | 2009-542679 | 12/2009 | |
| WO | WO-2007010085 A2 * | 1/2007 | ........... C07D 209/46 |
| WO | WO 2009/088531 | 7/2009 | |
| WO | WO 2009/158011 | 12/2009 | |

OTHER PUBLICATIONS

Valderrama, J. et al. Synthetic Communications 27(12), 2143-2157 (1997). (Year: 1997).*
International Search Report prepared by the Korean Intellectual Property Office dated Oct. 8, 2015, for International Application No. PCT/KR2015/007562.
Terzioglu et al. "Synthesis and structure-activity relationships of indole and benzimidazole piperazines as histamine $H_4$ receptor antagonists", Bioorganic & Medicinal Chemistry Letters 14 (2004) 5251-5256.
Yarovenko et al. "Synthesis and reactivity monothiooxamides of the aminonitroarene series", Russian Chemical Bulletin, International Edition, 2009, vol. 58(6), pp. 1276-1280.
Baba et aL "Preparation of N,N-Dimethyl Aromatic: Amides from Aromatic: Aldehydes with Dimethylamine and iodine Reagents", Synlett, 2012, vol. 23, pp. 1175-1180.
Chi-Ting et al., "The Synthesis of Some Indole and Benzofuran Derivatives Carrying a Dialkylaminomethyl Side Chain", Acta Chimica Sinica, 1962, vol. 28(4). pp. 236-243.
Tavares et al. "6-(4-Chlorophenyl)-3-substituted-thieno[3,2-d]pyrimidin-4(3H)-one Based Melanin-Concentrating Hormone Receptor 1 Antagonist", Journal of Medicinal Chemistry, 2006, vol. 49, pp. 7108-7118.
Database PubChem [Online] National Center for Biotechnology Information, U.S. National Library of Medicine, 2005 [retrieved on Sep. 18, 2005]. Retrieved from the Internet: pubchem.ncbi.nlm.nih.gov/compound/5133795.

(Continued)

*Primary Examiner* — Samantha L Shterengarts
(74) *Attorney, Agent, or Firm* — Sheridan Ross P.C.

(57) ABSTRACT

The present invention relates to a novel indene derivative, a preparation method for the same, and a pharmaceutical composition for treating retinal disease comprising the same as an active ingredient. The novel indene derivative of the present invention, the optional isomer of the same, or the pharmaceutically acceptable salts of the same have excellent inhibitory efficiency of receptor-interacting serine-threonine-protein kinase 1 (RIPK1). Therefore, the composition containing the same as an active ingredient can be effectively used as a pharmaceutical composition for treating retinal disease.

7 Claims, 15 Drawing Sheets

(56) References Cited

OTHER PUBLICATIONS

Database PubChem [Online] National Center for Biotechnology information, U.S National Library of Medicine. 2005 [retrieved on Jul. 29, 2005]. Retrieved from the Internet: pubchem.ncbi.nlm.nih.gov/compound/29883316.

Database PubChem [Online] National Center for Biotechnology information, U.S National Library of Medicine, 2005 [retrieved on Sep. 13, 2005I, Retrieved from the Internet: pubchem.ncbi.nlm.nih.gov/compound/4210929.

Dong et al. "Necrostatin-1 Protects Photoreceptors from Cell Death and Improves Functional Outcome after Experimental Retinal Detachment", The American Journal of Pathology, vol. 181, No. 5, Nov. 2012, pp. 1634-1641.

Sato et al. "Receptor Interacting Protein Kinase-Mediated Necrosis Contributes to Cone and Rod Photoreceptor Degeneration in the Retina Lacking Interphotoreceptor Retinoid-Binding Protein", The Journal of Neuroscience, Oct. 30, 2013, 33(44): 17458-17468.

Murakami et al. "RIP Kinase-Mediated Necrosis as an Alternative Mechanism of Photoreceptor Death", Oncotarget, June, vol. 2, No. 6, pp. 497-509.

Trichonas et al. "Receptor interacting protein kinases mediate retinal detachment-induced photoreceptor necrosis and compensate for inhibition of apoptosis", Proceedings of the National Academy of Sciences of the United States of America, Dec. 14, 2010, vol. 107, No. 50, pp. 21695-21700.

Pierson et al. "5-Hydroxyindole-2-carboxylic Acid Amides: Novel Histamine-3 Receptor Inverse Agonists for the Treatment of Obesity," Journal of Medicinal Chemistry, Jul. 2009, vol. 52, No. 13, pp. 3855-3868.

Buchel "Synthesen von elektronegativ substituierten Benzimidazolen," Z. Fur Naturforsch. B, 1970, vol. 25, No. 9, pp. 945-953.

Kabalka et al. "A microwave-enhanced, solventless Mannich condensation of terminal alkynes and secondary amines with paraformaldehyde on cuprous iodide doped alumina," Tetrahedron, 2006, vol. 62, pp. 857-867.

Valderrama et al. "Synthesis and in Vitro Antiprotozoal Activity of Thiophene Ring-Containing Quinones," Chem. Pharm. Bull. Sep. 1999, vol. 47, No. 9, pp. 1221-1226.

\* cited by examiner

FUSED HETEROCYCLIC RING COMPOUNDS AND METHOD OF TREATING RETINAL DISEASE USING SAME

CROSS-REFERENCES TO RELATED APPLICATION

The application is a continuation of PCT Application No. PCT/KR2015/007562 having an international filing date of 21 Jul. 2015, which PCT application claimed claims the benefit of priority from Korean Patent Application No. 10-2014-0095676, filed on Jul. 28, 2014 the disclosures of each of which are incorporated herein by reference.

BACKGROUND OF THE INVENTION

1. Field of the Invention

The present invention relates to a novel indene derivative, a preparation method for the same, and a pharmaceutical composition for preventing or treating retinal disease comprising the same as an active ingredient.

2. Description of the Related Art

The nerve tissue located in the center of the inner retina of the eye is called the macula. Most of the visual cells responding to the light stimulus are gathered here and the image of an object becomes focused in the center of the macula, suggesting that it plays a very important role in visual acuity. AMD (Age-related Macular Degeneration) is a chronic disease characterized by degeneration of macula pigment epithelium, Bruch's membrane, and choroidal capillaries of the macula. Anatomically, the neurosensory retina is located in front of the retinal pigment epithelium and depends on the retinal pigment epithelium for its nutrition, support, recirculation, and waste treatment. The said Bruch's membrane is a five-layered structure that is interposed between the choroid and the retinal pigment epithelium. The innermost layer is the basement membrane of the retinal pigment epithelium and the outermost layer is the basement membrane of the choroidal capillary endothelial cells. That is, AMD is a degenerative disease developed in the retinal pigment epithelium, Bruch's membrane and choroidal capillary complex.

This disease mainly occurs in people aged 50 years or older. In the West, this disease is the main cause of blindness in people over 60 and it is increasing in Korea. The cause of AMD is not clearly understood yet, but aging is the most possible risk factor (since the disease rate rapidly increases in those over 75). The most possible environmental cause is smoking. In addition, hypertension, obesity, genetic predisposition, excessive UV exposure, Low serum antioxidant concentration, etc, are regarded as the causes.

There are two types of macular degeneration, which are dry (nonexudative) macular degeneration and wet (exudative) macular degeneration. In the case of dry macular degeneration (dry AMD, nonexudative AMD, nonneovascular AMD), waste is deposited to form a yellow sediment called drusen under the retina and when this deposit is growing it disturbs blood flow to the retina particularly to the macula, resulting in the blurry vision and visual impairment. Dry macular degeneration does not cause sudden loss of vision, but it can progress to wet macular degeneration.

Wet macular degeneration (wet AMD, exudative AMD, neovascular AMD) is caused when angiogenesis is developed in the choroid below the retina. When the weak new blood vessel is broken, it results in bleeding or extrusion that causes degeneration of the macula area of the retina to cause vision impairment. Wet macular degeneration progresses rapidly, so that the visual acuity worsens within weeks and blindness may occur between two months and three years.

The treatment methods for macular degeneration known so far are photodynamic therapy (PDT) and anti-VEGF injection. In PDT, visudyne, the light-sensitive material is injected through blood vessel and when the light-sensitive material reaches to the newly formed blood vessels of the retina after a little while a special laser reacting to the light-sensitive material only is irradiated to the eyes to destroy the newly formed blood vessels selectively. However, there are many cases of recurrence even after this treatment, so it is often necessary to repeat the treatment. In the case of the repeated treatment, the retina itself may also be damaged.

The antibody (anti-VEGF) injection is an intravitreal injection of an antibody (anti-VEGF) that inhibits the formation and proliferation of new blood vessels by selectively binding to vascular endothelial growth factor (VEGF), which is an important factor for the generation and progression of new blood vessels. The protein antibodies used for the anti-VEGF injection are Lucentis and Avastin. Lucentis is a drug approved by FDA for the treatment of wet macular degeneration agent. Avastin is a drug approved for the treatment of cancer and is used for eye disease. However, the anti-VEGF injection is costly and is inconvenient because it cannot be dropped or applied to the eye and instead requires direct injection through the eye. It also needs a regular treatment once a month, suggesting that there is a risk of bleeding, pain, infection, retinal detachment, etc.

Therefore, studies to treat macular degeneration via different methods from the above have been going on. Recently, a strategy to develop a neuroprotectant that inhibits the death of the retinal nerve causing macular degeneration has been proposed (*Retina today* 2012. 64-65). Phosphorylation of RIPK1 (receptor-interacting serine/threonine-protein kinase 1) was observed in the retina of rats when the photoreceptor degeneration was induced by retinal detachment. It has been reported that the phosphorylation was reduced and the photoreceptor degeneration was also protected by the treatment of the RIPK1 enzyme activity inhibitor, Necrostain-1 (Nec-1) (*Am J Pathol* 2012. 181, 1634-1641).

In addition, there are other papers published continuously about the protection of retinal degeneration by the RIPK1 inhibitor Nec-1 (*J Neurosci,* 2013. 33(44), 17458-17468; *Am J Pathol* 2012. 181, 1634-1641; *Oncotarget,* 2011. 2(6), 497-509; *Proc Natl Acad Sci USA,* 2010. 107(50):21695-21700). This means that the RIPK1 enzyme activity inhibitor can be used as a macular degeneration treating agent.

Therefore, the present inventors confirmed that the novel indene derivative could inhibit RIPK1 enzyme activity when it was applied to the eye, suggesting that the novel indene derivative could be useful for the treatment of retinal disease such as macular degeneration, leading to the completion of the invention.

SUMMARY OF THE INVENTION

It is an object of the present invention to provide a novel indene derivative, an optical isomer thereof, or a pharmaceutically acceptable salt of the same.

It is another object of the present invention to provide a method for preparing the indene derivative above.

It is also an object of the present invention to provide a pharmaceutical composition for the prevention or treatment of retinal disease comprising the indene derivative above as an active ingredient.

It is further an object of the present invention to provide a health functional food for the prevention or improvement of retinal disease comprising the indene derivative above as an active ingredient.

To achieve the above objects, the present invention provides a compound represented by formula 1, an optical isomer, or a pharmaceutically acceptable salt of the same.

[Formula 1]

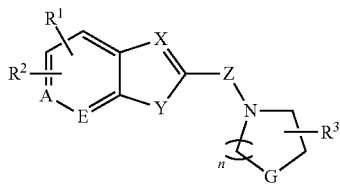

In the formula 1, $R^1$ is substituted 5-10 membered heteroaryl containing —H, —OH, —NH$_2$, halogen, straight or branched C$_{1-10}$ alkyl, straight or branched C$_{1-10}$ alkoxy, —C(=O) NR$^5$R$^6$, —NR$^7$R$^8$, substituted C$_{6-10}$ aryl, and one or more hetero atoms selected from the group consisting of N, O, and S, C$_{6-10}$ aryl substituted straight or branched C$_{1-10}$ alkyl, C$_{6-10}$ aryl substituted straight or branched C$_{1-10}$ alkoxy, substituted C$_{6-10}$ aryloxy, C$_{6-10}$ aryl substituted straight or branched C$_{1-10}$ alkylsulfonyl, or C$_{6-10}$ aryl substituted straight or branched C$_{1-10}$ alkylthio, In the substituted 5-10 membered heteroaryl, C$_{6-10}$ aryl substituted straight or branched C$_{1-10}$ alkyl, C$_{6-10}$ aryl substituted straight or branched C$_{1-10}$ alkoxy, substituted C$_{6-10}$ aryloxy, C$_{6-10}$ aryl substituted straight or branched C$_{1-10}$ alkylsulfonyl, or C$_{6-10}$ aryl substituted straight or branched C$_{1-10}$ alkylthio, one or more substituents selected from the group consisting of —OH, —NR$^9$R$^{10}$, straight or branched C$_{1-5}$ alkyl, halogen, nitrile, straight or branched C$_{1-5}$ alkoxy which is unsubstituted or substituted with one or more halogen, straight or branched C$_{1-5}$ alkylthio, phenyl, —C(=O)OH, —S(=O)OCH$_3$, and —C(=O)NH$_2$ are substituted and 5-8 membered heteroaryl containing one or more heteroatoms selected from the group consisting of N, O, and S can be fused, Wherein R$^5$ and R$^6$ are independently —H, or straight or branched C$_{1-5}$ alkyl, R$^7$ and R$^8$ are independently —H, straight or branched C$_{1-5}$ alkyl, straight or branched C$_{1-5}$ alkylcarbonyl, substituted C$_{6-10}$ arylsulfonyl, or substituted C$_{6-10}$ aryl. In the substituted C$_{6-10}$ arylsulfonyl and substituted C$_{6-10}$ aryl, one or more halogen atoms can be substituted, R$^9$ and R$^{10}$ are independently —H, straight or branched C$_{1-5}$ alkyl, straight or branched C$_{1-5}$ alkoxy, or straight or branched C$_{1-5}$ alkylcarbonyl;

R$^2$ is —H, —OH, halogen, straight or branched C$_{1-10}$ alkyl, or straight or branched C$_{1-10}$ alkoxy, Wherein R$^1$ and R$^2$ can form C$_{6-10}$ aryl along with carbon atoms which are conjugated to the same;

R$^3$ is —H, —OH, straight or branched C$_{1-5}$ alkyl, amine, or —C(=O)OH;

G is —O—, —CH$_2$—, —NH—, —N(CH$_3$)—, or —S—;

Y is —O—, —S—, or —NR$^4$—,

Wherein, R$^4$ is —H, or straight or branched C$_{1-5}$ alkyl;

X, E, A are independently —CH=, or —N=;

Z is —C(=O)—, or —CH$_2$—;

N is an integer of 1-5.

The present invention also provides a method for preparing the compound represented by formula 1 containing the step of reacting the compound represented by formula 2 with the compound represented by formula 3 to give the compound represented by formula 1 (step 1) as shown in the below reaction formula 1.

[Reaction Formula 1]

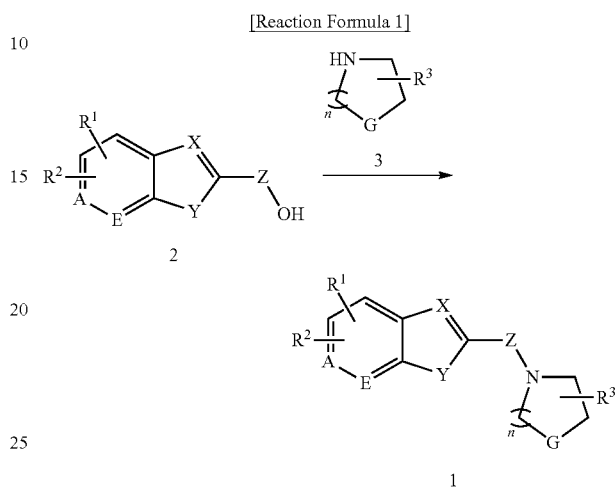

(In the reaction formula 1, R$^1$, R$^2$, R$^3$, A, E, X, Y, Z, G, and n are as defined in formula 1).

The present invention also provides a method for preparing the compound represented by formula 1 containing the step of reacting the compound represented by formula 4 with the compound represented by formula 5 to give the compound represented by formula 1 (step 1) as shown in the below reaction formula 2.

[Reaction Formula 2]

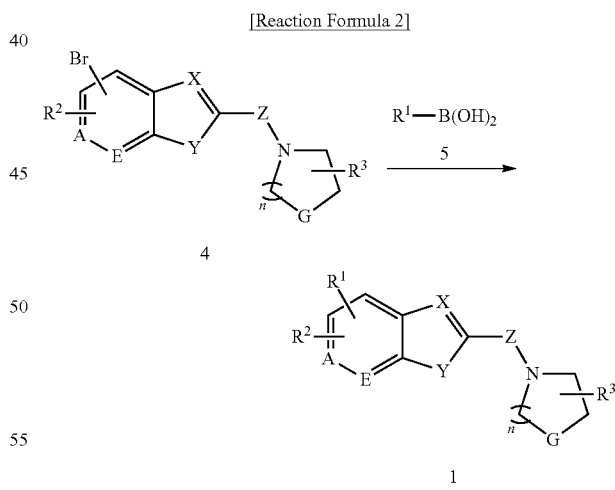

(In the reaction formula 2, R$^1$, R$^2$, R$^3$, A, E, X, Y, Z, G, and n are as defined in formula 1).

The present invention also provides a pharmaceutical composition for the prevention or treatment of retinal disease comprising the compound represented by formula 1, the optical isomer thereof, or the pharmaceutically acceptable salt of the same as an active ingredient.

In addition, the present invention provides a health functional food for the prevention or improvement of retinal disease comprising the compound represented by formula 1, the optical isomer thereof, or the pharmaceutically acceptable salt of the same as an active ingredient.

Advantageous Effect

The novel indene derivative of the present invention, the optical isomer of the same, or the pharmaceutically acceptable salt of the same has excellent inhibitory efficiency of receptor-interacting serine/threonine-protein kinase 1 (RIPK1). Therefore, the composition containing the same as an active ingredient can be effectively used as a pharmaceutical composition for preventing or treating retinal disease exemplified by retinitis pigmentosa (RP), Leber congenital amaurosis (LCA), Stargardts disease, Usher syndrome, choroideremia, rod-cone or cone-rod dystrophy, ciliopathy, mitochondrial disorders, progressive retinal atrophy, degenerative retinal diseases, age-related macular degeneration (AMD), wet AMD, dry AMD, geographical atrophy, inherited or acquired macular degeneration, retinal photoreceptor diseases, retinal pigment epithelial diseases, diabetic retinopathy, cystic macular edema, uveitis, retinal detachment, traumatic retinal injury, iatrogenic retinal injury, macular holes, macular capillarectasia, ganglion cell diseases, optic nerve diseases, glaucoma, optic neuropathy, ischemic retinal diseases, retinopathy of prematurity, occlusion of retinal vessels, inherited macroaneurysm, retinal vascular diseases, ophthalmic vascular diseases, glaucomatous retinal neurodegeneration, ischemic optic neuropathy and the like.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
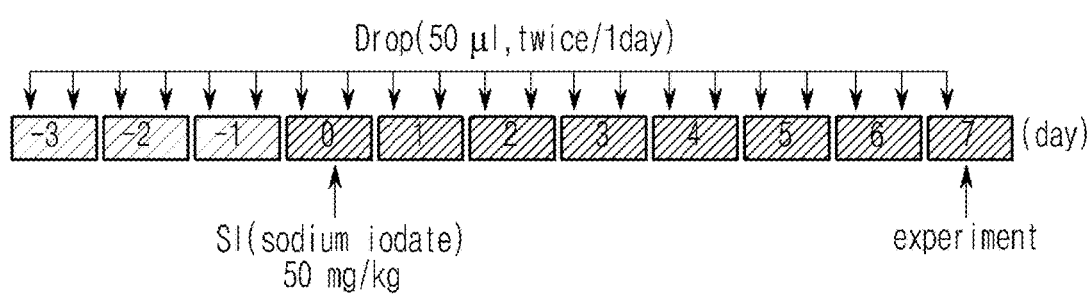
FIG. 1 is a schematic diagram illustrating the construction of a dry macular degeneration rat model and the instillation of the compounds of examples.

Hereinafter, the present invention is described in detail.

The present invention provides a compound represented by formula 1, an optical isomer, or a pharmaceutically acceptable salt of the same.

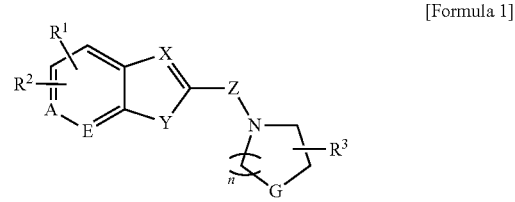

[Formula 1]

In the formula 1, $R^1$ is substituted 5-10 membered heteroaryl containing —H, —OH, —NH$_2$, halogen, straight or branched C$_{1-10}$ alkyl, straight or branched C$_{1-10}$ alkoxy, —C(=O)NR$^5$R$^6$, —NR$^7$R$^8$, substituted C$_{6-10}$ aryl, and one or more hetero atoms selected from the group consisting of N, O, and S, C$_{6-10}$ aryl substituted straight or branched C$_{1-10}$ alkyl, C$_{6-10}$ aryl substituted straight or branched C$_{1-10}$ alkoxy, substituted C$_{6-10}$ aryloxy, C$_{6-10}$ aryl substituted straight or branched C$_{1-10}$ alkylsulfonyl, or C$_{6-10}$ aryl substituted straight or branched C$_{1-10}$ alkylthio, In the substituted 5-10 membered heteroaryl, C$_{6-10}$ aryl substituted straight or branched C$_{1-10}$ alkyl, C$_{6-10}$ aryl substituted straight or branched C$_{1-10}$ alkoxy, substituted C$_{6-10}$ aryloxy, C$_{6-10}$ aryl substituted straight or branched C$_{1-10}$ alkylsulfonyl, or C$_{6-10}$ aryl substituted straight or branched C$_{1-10}$ alkylthio, one or more substituents selected from the group consisting of —OH, —NR$^9$R$^{10}$, straight or branched C$_{1-5}$ alkyl, halogen, nitrile, straight or branched C$_{1-5}$ alkoxy which is unsubstituted or substituted with one or more halogen, straight or branched C$_{1-5}$ alkylthio, phenyl, —C(=O)OH, —S(=O)OCH$_3$, and —C(=O)NH$_2$ are substituted and 5-8 membered heteroaryl containing one or more heteroatoms selected from the group consisting of N, O, and S can be fused, Wherein $R^5$ and $R^6$ are independently —H, or straight or branched $C_{1-5}$ alkyl, $R^7$ and $R^8$ are independently —H, straight or branched $C_{1-5}$ alkyl, straight or branched $C_{1-5}$ alkylcarbonyl, substituted $C_{6-10}$ arylsulfonyl, or substituted $C_{6-10}$ aryl. In the substituted $C_{6-10}$ arylsulfonyl and substituted $C_{6-10}$ aryl, one or more halogen atoms can be substituted, $R^9$ and $R^{10}$ are independently —H, straight or branched $C_{1-5}$ alkyl, straight or branched $C_{1-5}$ alkoxy, or straight or branched $C_{1-5}$ alkylcarbonyl;

$R^2$ is —H, —OH, halogen, straight or branched $C_{1-10}$ alkyl, or straight or branched $C_{1-10}$ alkoxy, Wherein $R^1$ and $R^2$ can form $C_{6-10}$ aryl along with carbon atoms which are conjugated to the same;

$R^3$ is —H, —OH, straight or branched $C_{1-5}$ alkyl, amine, or —C(=O)OH;

G is —O—, —CH$_2$—, —NH—, —N(CH$_3$)—, or —S—;
Y is —O—, —S—, or —NR$^4$—,
Wherein, $R^4$ is —H, or straight or branched $C_{1-5}$ alkyl;
X, E, and A are independently —CH=, or —N=;
Z is —C(=O)—, or —CH$_2$—;
N is an integer of 1-5.

At least one of the followings is preferably excluded;
X, E, and A are —CH=, Y is —NH—, Z is —C(=O)—, n is 2, G is —O—, $R^3$ is —H, and one of $R^1$ and $R^2$ is —Cl, the other is —H;

X is —N=, E and A are —CH=, Y is —NH—, Z is —C(=O)—, n is 2, G is —O—, $R^3$ is —H, and one of $R^1$ and $R^2$ is —CH$_3$, the other is —H;

X is —N=, E and A are —CH=, Y is —NH—, Z is —C(=O)—,
n is 2, G is —O—, $R^3$ is —H, and $R^1$ and $R^2$ are both —H;

X, E, and A are —CH=, Y is —O—, Z is —C(=O)—, n is 2, G is —O—, $R^3$ is —H, and $R^1$ and $R^2$ are both —H;

X, E, and A is —CH=, Y is —NCH$_3$—, Z is —C(=O)—, n is 2, G is —O—, $R^3$ is —H, and $R^1$ and $R^2$ are both —H; X, E, and A is —CH=, Y is —S—, Z is —C(=O)—, n is 2,
G is —O—, $R^3$ is —H, and one of $R^1$ and $R^2$ is —NH$_2$, the other is —H;

X, E, and A is —CH=, Y is —S—, Z is —C(=O)—, n is 2, G is —O—, $R^3$ is —H, and $R^1$ and $R^2$ are phenyl along with carbon atoms which are conjugated to the same;

X, E, and A is —CH=, Y is —O—, Z is —C(=O)—, n is 2, G is —O—, $R^3$ is —H, and one of $R^1$ and $R^2$ is —Br, the other is —H;

X, E, and A is —CH=, Y is —NH—, Z is —C(=O)—, n is 2, G is —O—, $R^3$ is —H, and one of $R^1$ and $R^2$ is methyl, the other is —H;

X, E, and A is —CH=, Y is —NH—, Z is —C(=O)—, n is 2, G is —O—, $R^3$ is —H, and one of $R^1$ and $R^2$ is methoxy, the other is —H; and X, E, and A is —CH=, Y is —O—, Z is —C(=O)—, n is 2, G is —O—, $R^3$ is —H, and one of $R^1$ and $R^2$ is methoxy, the other is —H.

Preferably,
$R^1$ is substituted 5-8 membered heteroaryl containing —H, —OH, —NH$_2$, halogen, straight or branched $C_{1-5}$ alkyl, straight or branched $C_{1-5}$ alkoxy, —C(=O)NR$^5$R$^6$, —NR$^7$R$^8$, substituted $C_{6-8}$ aryl, and one or more hetero atoms selected from the group consisting of, N, O, and S, $C_{6-8}$ aryl substituted straight or branched $C_{1-5}$ alkyl, $C_{6-8}$ aryl substituted straight or branched $C_{1-5}$ alkoxy, substituted $C_{6-8}$ aryloxy, $C_{6-8}$ aryl substituted straight or branched $C_{1-5}$ alkylsulfonyl, or $C_{6-8}$ aryl substituted straight or branched $C_{1-5}$ alkylthio, In the substituted 5-8 membered heteroaryl, $C_{6-8}$ aryl substituted straight or branched $C_{1-5}$ alkyl, $C_{6-8}$ aryl substituted straight or branched $C_{1-5}$ alkoxy, substituted $C_{6-8}$ aryloxy, $C_{6-8}$ aryl substituted straight or branched $C_{1-5}$ alkylsulfonyl, or $C_{6-8}$ aryl substituted straight or branched $C_{1-5}$ alkylthio, one or more substituents selected from the group consisting of —OH, —NR$^9$R$^{10}$, straight or branched $C_{1-3}$ alkyl, halogen, nitrile, straight or branched $C_{1-5}$ alkoxy which is unsubstituted or substituted with one or more halogen, straight or branched $C_{1-5}$ alkylthio, phenyl, C(=O)OH, —S(=O)OCH$_3$, and —C(=O)NH$_2$ are substituted and 5-6 membered heteroaryl containing one or more heteroatoms selected from the group consisting of N, O, and S can be fused, Wherein $R^5$ and $R^6$ are independently —H, or straight or branched $C_{1-3}$ alkyl, $R^7$ and $R^8$ are independently —H, straight or branched $C_{1-3}$ alkyl, straight or branched $C_{1-5}$ alkylcarbonyl, substituted $C_{6-8}$ arylsulfonyl, or substituted $C_{6-10}$ aryl. In the substituted $C_{6-8}$ arylsulfonyl and substituted $C_{6-10}$ aryl, one or more halogen atoms can be substituted, $R^9$ and $R^{10}$ are independently —H, straight or branched $C_{1-5}$ alkyl, straight or branched $C_{1-5}$ alkoxy, or straight or branched $C_{1-5}$ alkylcarbonyl;

$R^2$ is —H, —OH, halogen, straight or branched $C_{1-5}$ alkyl, or straight or branched $C_{1-5}$ alkoxy, Wherein $R^1$ and $R^2$ can form $C_{6-8}$ aryl along with carbon atoms which are conjugated to the same;

$R^3$ is —H, —OH, straight or branched $C_{1-3}$ alkyl, amine, or —C(=O)OH;

G is —O—, —CH$_2$—, —NH—, —N(CH$_3$)—, or —S—;
Y is —O—, —S—, or —NR$^4$—,
Wherein, $R^4$ is —H, or straight or branched $C_{1-3}$ alkyl;
X, E, and A are independently —CH=, or —N=;
Z is —C(=O)—, or —CH$_2$—;
N is an integer of 1-4.

At least one of the followings is preferably excluded;
X, E, and A are —CH=, Y is —NH—, Z is —C(=O)—, n is 2, G is —O—, $R^3$ is —H, and one of $R^1$ and $R^2$ is —Cl, the other is —H;

X is —N=, E and A are —CH=, Y is —NH—, Z is —C(=O)—, n is 2, G is —O—, $R^3$ is —H, and one of $R^1$ and $R^2$ is —CH$_3$, the other is —H;

X is —N=, E and A are —CH=, Y is —NH—, Z is —C(=O)—, n is 2, G is —O—, $R^3$ is —H, and $R^1$ and $R^2$ are both —H;

X, E, and A are —CH=, Y is —O—, Z is —C(=O)—, n is 2, G is —O—, $R^3$ is —H, and $R^1$ and $R^2$ are both —H;

X, E, and A is —CH=, Y is —NCH$_3$—, Z is —C(=O)—, n is 2, G is —O—, $R^3$ is —H, and $R^1$ and $R^2$ are both —H;

X, E, and A is —CH=, Y is —S—, Z is —C(=O)—, n is 2, G is —O—, $R^3$ is —H, and one of $R^1$ and $R^2$ is —NH$_2$, the other is —H;

X, E, and A is —CH=, Y is —S—, Z is —C(=O)—, n is 2, G is —O—, $R^3$ is —H, and $R^1$ and $R^2$ are phenyl along with carbon atoms which are conjugated to the same;

X, E, and A is —CH=, Y is —O—, Z is —C(=O)—, n is 2, G is —O—, $R^3$ is —H, and one of $R^1$ and $R^2$ is —Br, the other is —H;

X, E, and A is —CH=, Y is —NH—, Z is —C(=O)—, n is 2, G is —O—, $R^3$ is —H, and one of $R^1$ and $R^2$ is methyl, the other is —H;

X, E, and A is —CH═, Y is —NH—, Z is —C(═O)—, n is 2, G is —O—, $R^3$ is —H, and one of $R^1$ and $R^2$ is methoxy, the other is —H; and
X, E, and A is —CH═, Y is —O—, Z is —C(═O)—, n is 2, G is —O—, $R^3$ is —H, and one of $R^1$ and $R^2$ is methoxy, the other is —H.
More preferably,
$R^1$ is —H, methyl, methoxy, —OH, —Cl, —Br, —$NH_2$,
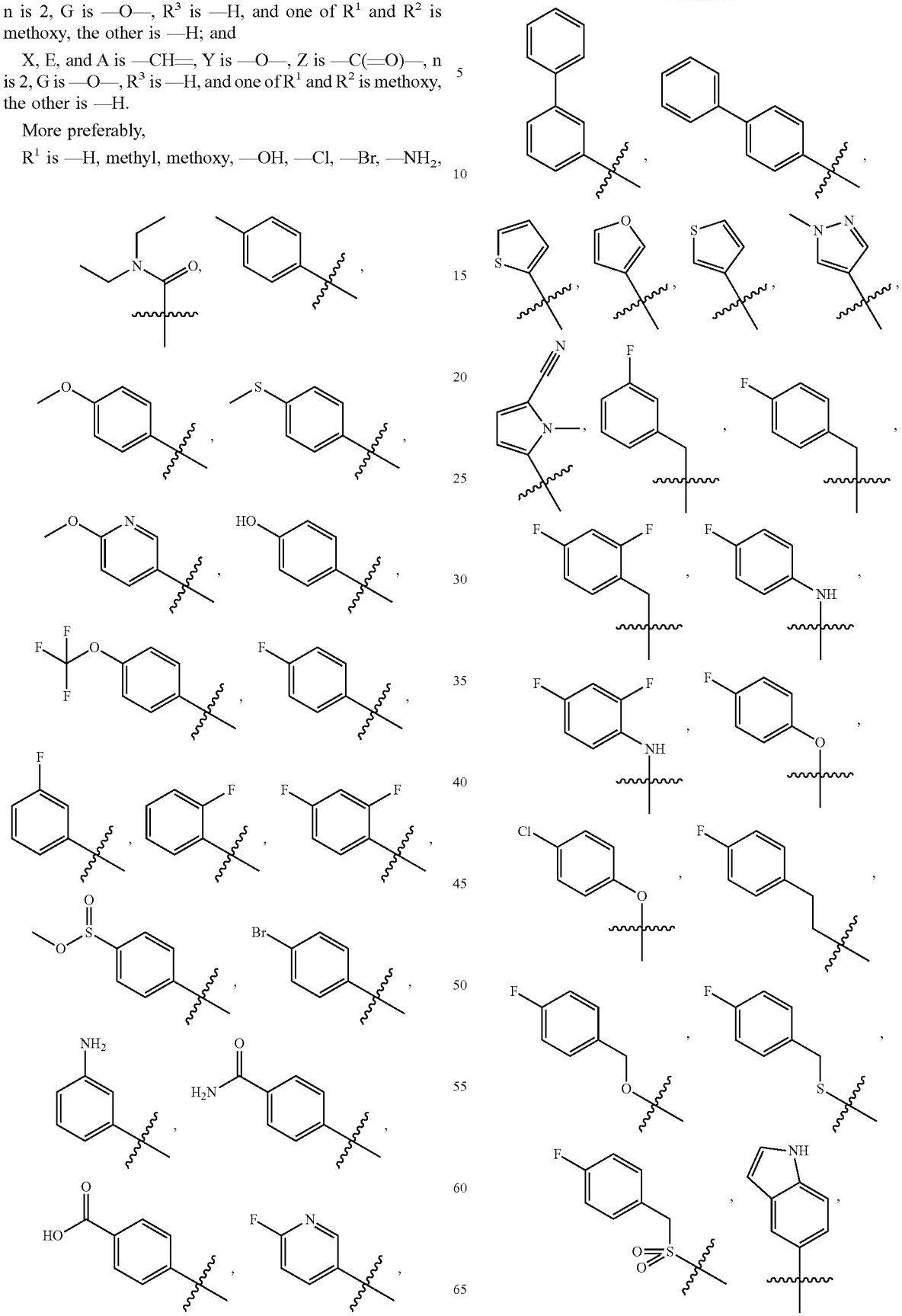

-continued

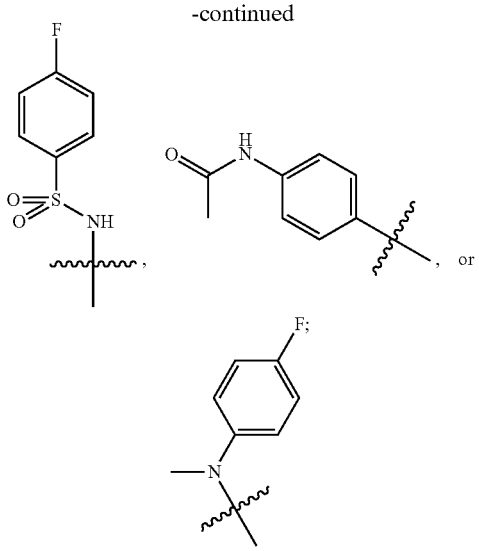

R² is —H, methyl, or —Cl,
Wherein R¹ and R² can form phenyl along with carbon atoms which are conjugated to the same;
R³ is —H, —OH, methyl, amine, or —C(=O)OH;
G is —O—, —CH₂—, —NH—, —N(CH₃)—, or —S—;
Y is —O—, —S—, or —NR⁴—,
Wherein, R⁴ is —H or methyl;
X, E, and A are independently —CH= or —N=;
Z is —C(=O)— or —CH₂—;
N is an integer of 1-3.

At least one of the followings is preferably excluded;
X, E, and A are —CH=, Y is —NH—, Z is —C(=O)—, n is 2, G is —O—, R³ is —H, and one of R¹ and R² is —Cl, the other is —H;

X is —N=, E and A are —CH=, Y is —NH—, Z is —C(=O)—, n is 2, G is —O—, R³ is —H, and one of R¹ and R² is —CH₃, the other is —H;

X is —N=, E and A are —CH=, Y is —NH—, Z is —C(=O)—, n is 2, G is —O—, R³ is —H, and R¹ and R² are both —H;

X, E, and A are —CH=, Y is —O—, Z is —C(=O)—, n is 2, G is —O—, R³ is —H, and R¹ and R² are both —H;

X, E, and A is —CH=, Y is —NCH₃—, Z is —C(=O)—, n is 2, G is —O—, R³ is —H, and R¹ and R² are both —H;

X, E, and A is —CH=, Y is —S—, Z is —C(=O)—, n is 2, G is —O—, R³ is —H, and one of R¹ and R² is —NH₂, the other is —H;

X, E, and A is —CH=, Y is —S—, Z is —C(=O)—, n is 2, G is —O—, R³ is —H, and R¹ and R² are phenyl along with carbon atoms which are conjugated to the same;

X, E, and A is —CH=, Y is —O—, Z is —C(=O)—, n is 2, G is —O—, R³ is —H, and one of R¹ and R² is —Br, the other is —H;

X, E, and A is —CH=, Y is —NH—, Z is —C(=O)—, n is 2, G is —O—, R³ is —H, and one of R¹ and R² is methyl, the other is —H;

X, E, and A is —CH=, Y is —NH—, Z is —C(=O)—, n is 2, G is —O—, R³ is —H, and one of R¹ and R² is methoxy, the other is —H; and X, E, and A is —CH=, Y is —O—, Z is —C(=O)—, n is 2, G is —O—, R³ is —H, and one of R¹ and R² is methoxy, the other is —H.

The compound represented by formula 1 of the present invention can be exemplified by the following compounds:
(1) (4-bromo-7-chlorothieno[2,3-c]pyridine-2-yl)(morpholino)methanone;
(2) (4-(4-fluorophenyl)thieno[2,3-c]pyridine-2-yl)(morpholino)methanone;
(3) (4-bromothieno[2,3-c]pyridine-2-yl)(morpholino)methanone;
(4) (4-(4-fluorophenyl)thieno[2,3-b]pyridine-2-yl)(morpholino)methanone;
(5) (7-chloro-4-(4-fluorophenyl)thieno[2,3-c]pyridine-2-yl)(morpholino)methanone;
(6) morpholino(naphtho[1,2-b]thiophene-2-yl)methanone;
(7) 4-((4-(4-fluorophenyl)benzo[b]thiophene-2-yl)methyl)morpholine;
(8) 4-(4-(4-fluorophenyl)benzo[b]thiophene-2-carbonyl)morpholine-3-carboxylic acid;
(9) (4-(1H-indole-5-yl)benzo[b]thiophene-2-yl)(morpholino)methanone;
(10) N-(4-(2-(morpholine-4-carbonyl)benzo[b]thiophene-4-yl)phenyl)acetamide;
(11) (5-hydroxy-1H-indole-2-yl)(morpholino)methanone;
(12) (5-chloro-1H-indole-2-yl)(morpholino)methanone;
(13) (5-methyl-1H-benzo[d]imidazole-2-yl)(morpholino)methanone;
(14) (5-bromo-1H-benzo[d]imidazole-2-yl)(morpholino)methanone;
(15) benzofuran-2-yl(morpholino)methanone;
(16) (5-bromobenzofuran-2-yl)(morpholino)methanone;
(17) (4,6-dimethylbenzo[b]thiophene-2-yl)(morpholino)methanone;
(18) (6,7-dimethylbenzo[b]thiophene-2-yl)(morpholino)methanone;
(19) (6-methoxybenzo[b]thiophene-2-yl)(morpholino)methanone;
(20) N,N-diethyl-2-(morpholine-4-carbonyl)benzo[b]thiophene-4-carboxamide;
(21) (5-methyl-1H-indole-2-yl)(morpholino)methanone;
(22) (5-methoxy-1H-indole-2-yl)(morpholino)methanone;
(23) (1H-benzo[d]imidazole-2-yl)(morpholino)methanone;
(24) (5-methoxy-1H-benzo[d]imidazole-2-yl)(morpholino)methanone;
(25) (1-methyl-1H-indole-2-yl)(morpholino)methanone;
(26) (5-methoxybenzofuran-2-yl)(morpholino)methanone;
(27) (6-methylbenzofuran-2-yl)(morpholino)methanone;
(28) (5-aminobenzo[b]thiophene-2-yl)(morpholino)methanone;
(29) (7-bromobenzo[b]thiophene-2-yl)(morpholino)methanone;
(30) (4-(2-fluorophenyl)benzo[b]thiophene-2-yl)(morpholino)methanone;
(31) (4-(biphenyl-4-yl)benzo[b]thiophene-2-yl)(morpholino)methanone;
(32) morpholino(4-p-tolylbenzo[b]thiophene-2-yl)methanone;
(33) 4-(2-(morpholine-4-carbonyl)benzo[b]thiophene-4-yl)benzoic acid;
(34) (4-(4-methoxyphenyl)benzo[b]thiophene-2-yl)(morpholino)methanone;
(35) (4-(4-fluorophenyl)benzo[b]thiophene-2-yl) (pyrrolidine-1-yl)methanone;
(36) (4-(3-fluorophenyl)benzo[b]thiophene-2-yl)(morpholino)methanone;
(37) (4-aminopiperidine-1-yl) (4-(4-fluorophenyl)benzo[b]thiophene-2-yl)methanone hydrochloride;
(38) (4-(4-fluorophenyl)benzo[b]thiophene-2-yl) (piperazine-1-yl)methanone hydrochloride;

(39) (4-(4-fluorophenyl)benzo[b]thiophene-2-yl)(morpholino)methanone;
(40) (5-(4-fluorophenyl)benzo[b]thiophene-2-yl)(morpholino)methanone;
(41) (4-(biphenyl-3-yl)benzo[b]thiophene-2-yl)(morpholino)methanone;
(42) (4-(3-aminophenyl)benzo[b]thiophene-2-yl)(morpholino)methanone;
(43) 4-(2-(morpholine-4-carbonyl)benzo[b]thiophene-4-yl)benzamide;
(44) (4-(4-hydroxyphenyl)benzo[b]thiophene-2-yl)(morpholino)methanone;
(45) morpholino(4-(4-(trifluoromethoxy)phenyl)benzo[b]thiophene-2-yl)methanone;
(46) (4-(4-fluorophenyl)benzo[b]thiophene-2-yl) (oxazolidine-3-yl)methanone;
(47) (4-(4-fluorophenyl)benzo[b]thiophene-2-yl) (piperidine-1-yl)methanone;
(48) (4-(4-fluorophenyl)benzo[b]thiophene-2-yl) (4-hydroxypiperidine-1-yl)methanone;
(49) (4-(4-fluorophenyl)benzo[b]thiophene-2-yl) (4-methylpiperazine-1-yl)methanone hydrochloride;
(50) (4-(4-(methylthio)phenyl)benzo[b]thiophene-2-yl)(morpholino)methanone;
(51) (4-(4-fluorophenyl)benzo[b]thiophene-2-yl)(thiomorpholino)methanone;
(52) (4-(4-fluorophenyl)benzo[b]thiophene-2-yl)(1,4-oxazepane-4-yl)methanone;
(53) (7-chloro-4-(4-fluorophenyl)benzo[b]thiophene-2-yl)(morpholino)methanone;
(54) (4-(4-bromophenyl)benzo[b]thiophene-2-yl)(morpholino)methanone;
(55) (4-(6-methoxypyridine-3-yl)benzo[b]thiophene-2-yl)(morpholino)methanone;
(56) (4-(3-fluorobenzyl)benzo[b]thiophene-2-yl)(morpholino)methanone;
(57) (4-(2,4-difluorobenzyl)benzo[b]thiophene-2-yl)(morpholino)methanone;
(58) (4-(2,4-difluorophenylamino)benzo[b]thiophene-2-yl)(morpholino)methanone;
(59) (4-(4-fluorophenoxy)benzo[b]thiophene-2-yl)(morpholino)methanone;
(60) (4-(4-fluorophenethyl)benzo[b]thiophene-2-yl)(morpholino)methanone;
(61) (4-(4-fluorobenzyloxy)benzo[b]thiophene-2-yl)(morpholino)methanone;
(62) (4-(4-fluorobenzylsulfonyl)benzo[b]thiophene-2-yl)(morpholino)methanone;
(63) (4-(2,4-difluorophenyl)benzo[b]thiophene-2-yl)(morpholino)methanone;
(64) methyl 4-(2-(morpholine-4-carbonyl)benzo[b]thiophene-4-yl)benzene sulfinate,
(65) (7-(4-fluorophenyl)benzo[b]thiophene-2-yl)(morpholino)methanone;
(66) (4-(6-fluoropyridine-3-yl)benzo[b]thiophene-2-yl)(morpholino)methanone hydrochloride;
(67) (4-(4-fluorobenzyl)benzo[b]thiophene-2-yl)(morpholino)methanone;
(68) (4-(4-fluorophenylamino)benzo[b]thiophene-2-yl)(morpholino)methanone;
(69) (4-((4-fluorophenyl)(methyl)amino)benzo[b]thiophene-2-yl)(morpholino)methanone;
(70) 4-fluoro-N-(2-(morpholine-4-carbonyl)benzo[b]thiophene-4-yl)benzenesulfonamide;
(71) (4-(4-fluorobenzylthio)benzo[b]thiophene-2-yl)(morpholino)methanone;
(72) 1-methyl-5-(2-(morpholine-4-carbonyl)benzo[b]thiophene-4-yl)-1H-pyrrole-2-carbonitrile;
(73) (4-(1-methyl-1H-pyrazol-4-yl)benzo[b]thiophene-2-yl)(morpholino)methanone;
(74) morpholino(4-(thiophene-2-yl)benzo[b]thiophene-2-yl)methanone;
(75) (4-(furan-3-yl)benzo[b]thiophene-2-yl)(morpholino)methanone; and
(76) morpholino(4-(thiophene-3-yl)benzo[b]thiophene-2-yl)methanone.

Among the compounds of examples 1~76, one or more compounds selected from the group consisting of the compounds of examples 6, 12, 13, 15, 16, 21, 22, 23, 25, 26, and 28 are preferably excluded.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydriodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the compound represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, an optical isomer, or a hydrate possibly produced from the same.

The present invention also provides a method for preparing the compound represented by formula 1 containing the step of reacting the compound represented by formula 2 with the compound represented by formula 3 to give the compound represented by formula 1 (step 1) as shown in the below reaction formula 1.

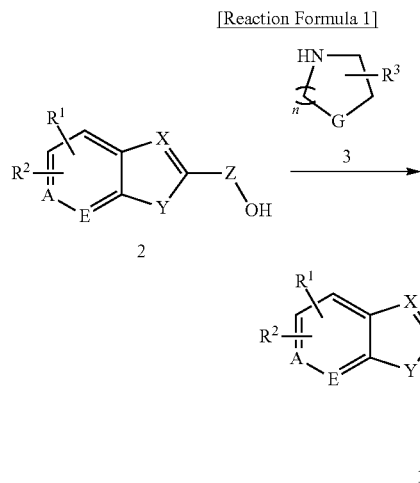

In the reaction formula 1, $R^1$, $R^2$, $R^3$, A, E, X, Y, Z, G, and n are as defined in formula 1.

Hereinafter, the method for preparing the compound represented by formula 1 of the present invention is described in more detail step by step.

In the method for preparing the compound represented by formula 1 of the invention, step 1 is to give the compound represented by formula 1 by reacting the compound represented by formula 2 with the compound represented by formula 3. More particularly, the compound represented by formula 2 was dissolved in an organic solvent, to which the compound represented by formula 3 and 1-ethyl-3-(3-dimethylaminopropyl)carbodiimide (EDC), 1-hydroxybenzotriazole (HOBT), and TEA were slowly added stepwise, followed by stirring to give the compound represented by formula 1.

At this time, the organic solvent above is preferably selected from the group consisting of dimethylformamide (DMF); ether solvents including dimethylene glycol ether (DME), ethyl ether, and 1,2-dimethoxyethane; lower alcohols including methanol, ethanol, propanol, and butanol; dimethylsulfoxide (DMSO), tetrahydrofuran, dioxane, acetonagensulfonate, toluenesulfonate, chlorobenzenesulfonate, xylensulfonate, phenylacetate, phenylpropionate, phenylbutylate, citrate, lactate, β-hydroxybutylate, glycolate, malate, tartrate, nethanesulfonate, propanesulfonate, naphthalene-1-sulfonate, naphathalene-2-sulfonate, and mandelate, and dimethylformamide is more preferred.

The reaction temperature is preferably between 0° C. and the boiling point of the solvent. The reaction time is not limited, but 0.5-10 hour reaction is preferred.

The present invention also provides a method for preparing the compound represented by formula 1 containing the step of reacting the compound represented by formula 4 with the compound represented by formula 5 to give the compound represented by formula 1 (step 1) as shown in the below reaction formula 2.

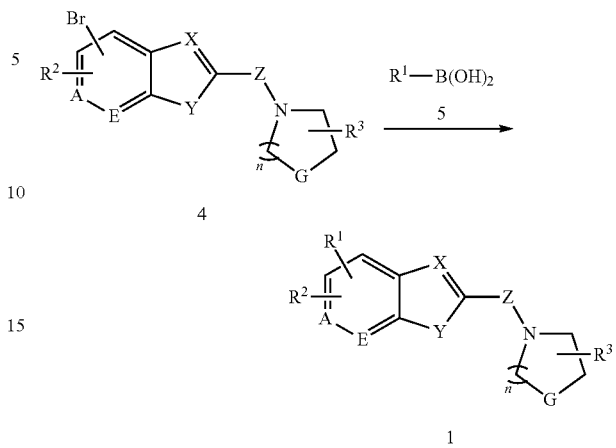

In the reaction formula 2, $R^1$, $R^2$, $R^3$, A, E, X, Y, Z, G, and n are as defined in formula 1.

Hereinafter, the method for preparing the compound represented by formula 1 of the present invention is described in more detail step by step.

In the method for preparing the compound represented by formula 1 of the invention, step 1 is to give the compound represented by formula 1 by reacting the compound represented by formula 4 with the compound represented by formula 5. More particularly, the compound represented by formula 4 was dissolved in an organic solvent, to which the compound represented by formula 5, an catalyst, and a base were added, followed by stirring to give the compound represented by formula 1.

At this time, the organic solvent above is preferably selected from the group consisting of dimethylformamide (DMF); ether solvents including dimethylene glycol ether (DME), ethyl ether, and 1,2-dimethoxyethane; lower alcohols including methanol, ethanol, propanol, and butanol; dimethylsulfoxide (DMSO), tetrahydrofuran, dioxane, acetonagensulfonate, toluenesulfonate, chlorobenzenesulfonate, xylensulfonate, phenylacetate, phenylpropionate, phenylbutylate, citrate, lactate, β-hydroxybutylate, glycolate, malate, tartrate, nethanesulfonate, propanesulfonate, naphthalene-1-sulfonate, naphathalene-2-sulfonate, and mandelate, and dimethylformamide is more preferred.

$Pd(PPh_3)_4$ can be used as the catalyst.

The base used herein is selected from the group consisting of organic bases such as pyridine, triethylamine, N,N-diisopropylethylamine (DIPEA), and 1,8-diazabicyclo[5.4.0]-7-undecene (DBU); and inorganic bases such as sodium hydroxide, sodium carbonate, potassium carbonate, cesium carbonate, and sodium hydride, which can be used by equivalent or excessive amount.

The reaction temperature is preferably between 0° C. and the boiling point of the solvent. The reaction time is not limited, but 0.5-10 hour reaction is preferred.

The present invention also provides a pharmaceutical composition for the prevention or treatment of retinal disease comprising the compound represented by formula 1, the optical isomer thereof, or the pharmaceutically acceptable salt of the same as an active ingredient.

At this time, the pharmaceutical composition is characterized by the activity of inhibiting RIPK1 (receptor-interacting serine/threonine-protein kinase 1). More precisely, RIPK1 is autophosphorylated in disease condition, and is thereafter bound to RIPK3 (receptor-interacting serine-threonine kinase 3) to form a necrosome and to stimulate the downstream signal system with it. As a result, necroptosis is induced. The compound of the invention inhibits the autophosphorylation of RPIK1, the key protein involved in necroptosis, and also inhibits the downstream death signal transduction. In conclusion, the compound of the invention has the function of protecting retinal nerve cells from death.

The retinal disease above can be retinitis pigmentosa (RP), Leber congenital amaurosis (LCA), Stargardts disease, Usher syndrome, choroideremia, rod-cone or cone-rod dystrophy, ciliopathy, mitochondrial disorders, progressive retinal atrophy, degenerative retinal diseases, age-related macular degeneration (AMD), wet AMD, dry AMD, geographical atrophy, inherited or acquired macular degeneration, retinal photoreceptor diseases, retinal pigment epithelial diseases, diabetic retinopathy, cystic macular edema, uveitis, retinal detachment, traumatic retinal injury, iatrogenic retinal injury, macular holes, macular capillarectasia, ganglion cell diseases, optic nerve diseases, glaucoma, optic neuropathy, ischemic retinal diseases, retinopathy of prematurity, occlusion of retinal vessels, inherited macroaneurysm, retinal vascular diseases, ophthalmic vascular diseases, glaucomatous retinal neurodegeneration, or ischemic optic neuropathy.

The eye drop of the invention can be formulated as a preservative-containing eye drop or a preservative-free eye drop. The preservative herein can be one or more compounds selected from the group consisting of benzalkonium chloride, methylparaben, and ethylparaben. The content of the preservative is preferably 5~15 weight part for 100 weight part of the main component.

Further, the formulations of the eye drop of the present invention can be, for example, aqueous solutions, suspensions, emulsions, etc., and aqueous solutions are more preferred. More particularly, when the eye drop formulation is an aqueous solution, a solvent is added to the eye drop composition, and sterilized purified water or distilled water for injection is preferably used as the solvent. In this case, it is necessary to adjust the amount of the solvent in the total amount of the final eye drop product. In the case of eye drop, the concentration of the eye drop is adjusted by the content of the solvent in addition to the eye drop composition.

The recommended dose and administration times of the eye drop composition of the present invention can be properly adjusted according to the symptoms in the range of 5~6 times of administration per day and 1 drop for one time administration.

The present invention also provides a health functional food for the prevention or improvement of retinal disease comprising the compound represented by formula 1, the optical isomer thereof, or the pharmaceutically acceptable salt of the same as an active ingredient.

At this time, the retinal disease above can be retinitis pigmentosa (RP), Leber congenital amaurosis (LCA), Stargardts disease, Usher syndrome, choroideremia, rod-cone or cone-rod dystrophy, ciliopathy, mitochondrial disorders, progressive retinal atrophy, degenerative retinal diseases, age-related macular degeneration (AMD), wet AMD, dry AMD, geographical atrophy, inherited or acquired macular degeneration, retinal photoreceptor diseases, retinal pigment epithelial diseases, diabetic retinopathy, cystic macular edema, uveitis, retinal detachment, traumatic retinal injury, iatrogenic retinal injury, macular holes, macular capillarectasia, ganglion cell diseases, optic nerve diseases, glaucoma, optic neuropathy, ischemic retinal diseases, retinopathy of prematurity, occlusion of retinal vessels, inherited macroaneurysm, retinal vascular diseases, ophthalmic vascular diseases, glaucomatous retinal neurodegeneration, or ischemic optic neuropathy.

Experiments were performed to evaluate the RIPK1 (receptor-interacting serine/threonine-protein kinase 1) inhibitory activity of the compounds of examples of the invention. As a result, the compounds of examples of the invention were confirmed to have RIPK1 inhibitory activity (see Experimental Example 1 Table 2).

Experiments were performed to evaluate the protective effect of the compounds of examples of the invention on the retinal nerve under oxygen-glucose deprivation condition. As a result, the compounds of the invention were confirmed to have better retinal nerve protective effect at the concentration of 20 µM than the compounds of Comparative Example 1 and Comparative Example 2 (see Experimental Example 2 Table 3).

In addition, experiments were performed to evaluate the protective effect of the compounds of examples of the invention on the retinal nerve under necroptosis inducing condition. As a result, the compounds of examples of the invention were confirmed to have retinal nerve protective effect at the concentration of 20 µM (see Experimental Example 3 Table 4).

Experiments were performed to evaluate the $IC_{50}$ concentration of the compound represented by formula 1 of the present invention against RIPK1 (receptor-interacting serine/threonine-protein kinase 1). As a result, the compound of the invention was confirmed to have low $IC_{50}$ concentration against RIPK1 (see Experimental Example 4 Table 5).

Experiments were performed with the 8-week-old dry macular degeneration rat model to evaluate the protective effect of the compound represented by formula 1 of the invention on retinal pigment epithelial cells. As a result, the compounds of example 39 (F001 and F002) were confirmed to have a significantly higher retinal pigment epithelial cell protective effect than the compounds of Comparative Examples 1 and 2 (see Experimental Example 5 Table 6, FIGS. 1, 2, and 3).

Experiments were performed with the 8-week-old dry macular degeneration rat model used in Experimental Example 5 to evaluate the protective effect of the compound represented by formula 1 of the invention on retinal layer thickness reduction. As a result, the compounds of example 39 (F001 and F002) were confirmed to have better protective effect on retinal layer thickness reduction than the compounds of Comparative Examples 1 and 2 (see Experimental Example 6, FIG. 4).

Further, experiments were performed with the 8-week-old dry macular degeneration rat model to evaluate the inhibitory effect of the compounds of the invention on retinal detachment. As a result, in the groups treated with the compounds of example 39 (F001 and F002), the retinal structure was maintained normally (see Experimental Example 7, FIGS. 5 and 6).

Experiments were performed with the 8-week-old dry macular degeneration rat model used in Experimental Example 7 to evaluate the inhibitory effect of the compounds of the invention on retinal degeneration. As a result, in the groups treated with the compounds of example 39 (F001 and F002), the retinal structure was maintained normally (see Experimental Example 8, FIG. 7).

To evaluate the retinal layer thickness protective effect of the compounds of the invention, experiments were performed with the dry macular degeneration rat model used in Experimental Example 7. As a result, the compounds of example 39 were confirmed to have retinal thickness protection effect of 70~80% (see Experimental Example 9, FIG. 8).

The drug efficacy of the compounds of the invention was investigated by retinal potential difference examination. ERG was measured in the retinal degeneration model using SI (Sodium Iodate). As a result, A wave was significantly reduced therein, which was decreased 50% by the normal level at 300 mcd. In particular, the retina protective effect of the instillated compound of example 39 (F004, 81%) was more significant than that of the orally-administered compound of Comparative Example 3 (HC (doxycycline), 31%) (Experimental Example 10 Table 7, FIGS. 9 and 10).

The retina protective effect of the compounds of example 39 (39-F003 and 39-F004) was respectively 81.9% and 91.2% by the normal control (100%), and the protective effect of those compounds of Comparative Examples (2-F001, 2-F002, 3-MH, and 3-HC) was 90.9%, 82.9%, 74.1%, and 66.9% by the normal control (100%).

Figure 11:
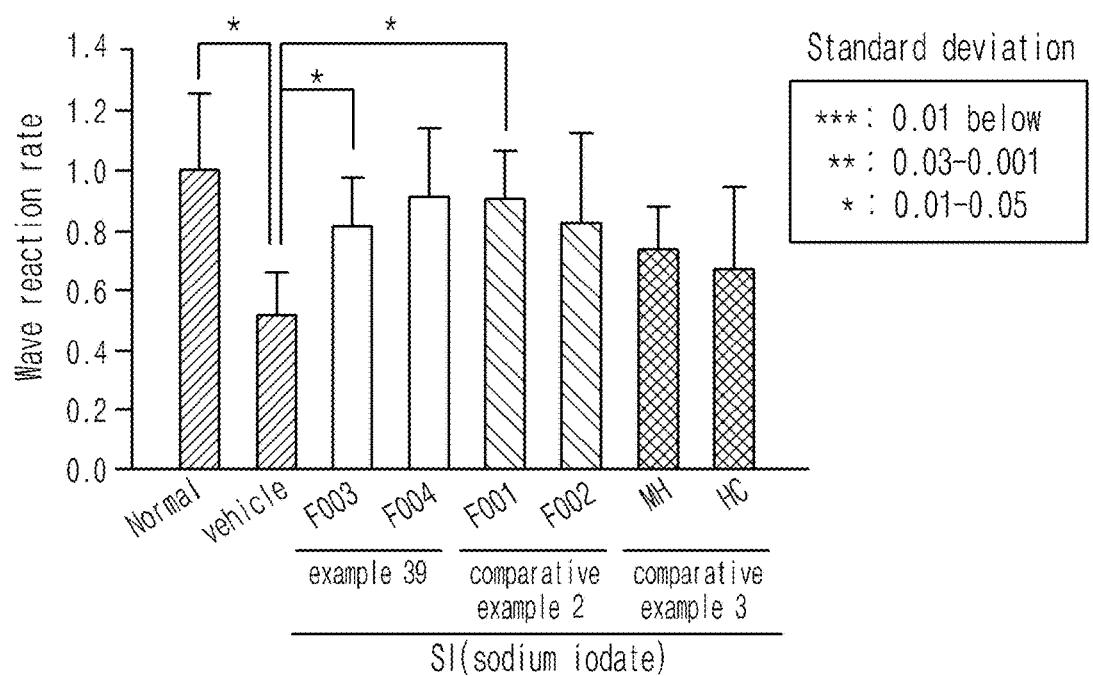
FIG. 11 is a graph illustrating the protective effect of the compounds of examples on the retinal photoreceptor cell degeneration in the dry macular degeneration rabbit model which was investigated by ERG.

More specifically, the compounds of example 39 (39-F003 (81.9%) and 39-F004 (91.2%)) displayed higher protective effect than those of the compounds of Comparative Example 3 (3-MH (74.1%) and 3-HC (66.9%)) (see Experimental Example 10, FIG. 11).

To evaluate the drug efficacy of the compounds of the invention, experiments were performed with the dry macular degeneration pig model using retinal fundus photographs. In the non-treated group (Veh), retinal pigment epithelium was degenerated, so that choroidal vessels and bright areas were observed. In the groups treated with the compounds of Comparative Examples (2-F001 (eye drop instillation) and 3-HC (oral-administration)), damaged areas (*) were observed. However, in the group treated with the compound of example 39 (39-F004, eye drop instillation) of the invention, normal retina was observed (see Experimental 11, FIGS. 12 and 13).

To evaluate the drug efficacy of the compounds of the invention by retinal potential difference examination, experiments were performed with the dry macular degeneration pig model used in Experimental Example 11. As a result, A wave was observed in the normal group, but A wave was decreased in those groups treated with the compounds of Comparative Examples (2-F001 and 3-HC). In the meantime, A wave was well preserved in the group treated with the compound of example 39 (39-F004), suggesting that the compound of the present invention had better retina protective effect than those compounds of Comparative Examples (2-F001 and 3-HC) (see Experimental Example 12 Table 8, FIGS. 14 and 15).

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Example 1> Preparation of (4-bromo-7-chlorothieno[2,3-c]pyridine-2-yl)(morpholino)methanone

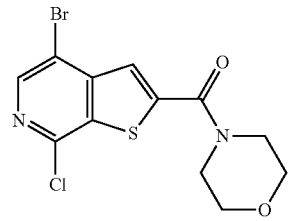 [SMILES: O=C(c1cc2c(Br)cnc(Cl)c2s1)N1CCOCC1]

4-bromo-7-chlorothieno[2,3-c]pyridine-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 11%.

1H NMR (300 MHz, DMSO-d6) δ 8.58 (s, 1H), 7.81 (s, 1H), 3.65 (s, 8H).

<Example 2> Preparation of (4-(4-fluorophenyl)thieno[2,3-c]pyridine-2-yl)(morpholino)methanone

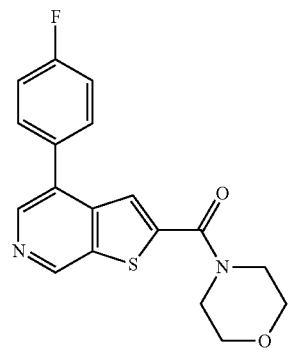

4-(4-fluorophenyl)thieno[2,3-c]pyridine-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 13%.

1H NMR (300 MHz, $CDCl_3$) δ 9.13 (s, 1H), 8.52 (s, 1H), 7.55-7.51 (m, 3H), 7.26-7.20 (m, 2H), 3.72 (s, 8H).

<Example 3> Preparation of (4-bromothieno[2,3-c]pyridine-2-yl)(morpholino)methanone

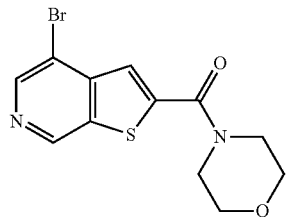 [SMILES: O=C(c1cc2c(Br)cncc2s1)N1CCOCC1]

4-bromothieno[2,3-c]pyridine-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 9%.

1H NMR (300 MHz, DMSO-d6) δ 9.30 (s, 1H), 8.67 (s, 1H), 8.67 (s, 1H), 7.70 (s, 1H), 3.65 (s, 8H).

<Example 4> Preparation of (4-(4-fluorophenyl)thieno[2,3-b]pyridine-2-yl)(morpholino)methanone

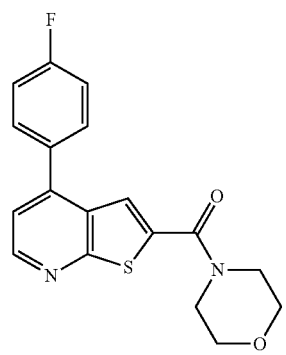 [SMILES: O=C(c1cc2c(-c3ccc(F)cc3)ccnc2s1)N1CCOCC1]

4-(4-fluorophenyl)thieno[2,3-b]pyridine-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 18%.

1H NMR (300 MHz, CDCl3) δ 8.64 (d, 1H), 7.57-7.53 (m, 3H), 7.30 (d, 1H), 7.22 (t, 2H), 3.72 (s, 8H).

<Example 5> Preparation of (7-chloro-4-(4-fluorophenyl)thieno[2,3-c]pyridine-2-yl)(morpholino)methanone

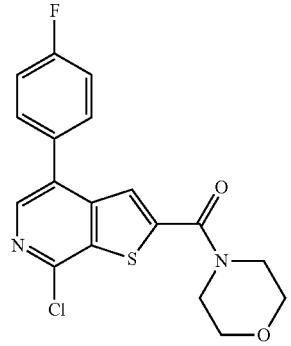

7-chloro-4-(4-fluorophenyl)thieno[2,3-c]pyridine-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 9%.

1H NMR (300 MHz, CDCl3) δ 8.30 (s, 1H), 7.57-7.47 (m, 3H), 7.25-7.19 (m, 2H), 3.72 (s, 8H).

<Example 6> Preparation of morpholino(naphtho[1,2-b]thiophene-2-yl)methanone

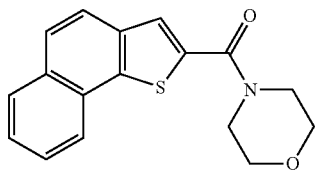 [SMILES: O=C(c1cc2ccc3ccccc3c2s1)N1CCOCC1]

Naphtho[1,2-b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 32%.

1H NMR (300 MHz, CDCl3) δ 8.12 (d. 1H), 7.93 (d, 1H), 7.76 (s, 1H), 7.62 (s, 1H), 7.60-7.53 (m, 2H), 3.85-3.78 (m, 8H).

<Example 7> Preparation of 4-((4-(4-fluorophenyl)benzo[b]thiophene-2-yl)methyl)morpholine

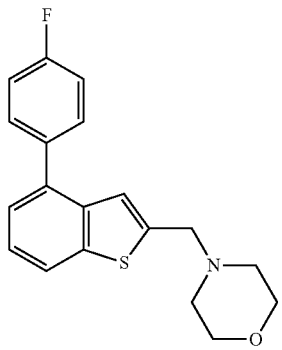 [SMILES: Fc1ccc(-c2cccc3sc(CN4CCOCC4)cc23)cc1]

2-(chloromethyl)-4-(4-fluorophenyl)benzo[b]thiophene (1 eq) was dissolved in toluene, to which morpholine (1.04 eq) and Na$_2$CO$_3$ (2 eq) were added. The mixture was stirred for overnight with reflux. The mixture was washed and extracted with EtOAc and water. The small amount of water remaining in the organic layer was dried over MgSO$_4$. The solvent was eliminated by vacuum distillation, followed by column chromatography for separation. As a result, a target compound was obtained with the yield of 35%.

1H NMR (300 MHz, CDCl3) δ 7.79 (d, 1H), 7.52-7.48 (m, 2H), 7.36-7.31 (m, 1H), 7.27-7.25 (m, 2H), 7.19-7.16 (m, 2H), 3.75-3.70 (m, 6H), 2.53-2.50 (m, 4H).

<Example 8> Preparation of 4-(4-(4-fluorophenyl)benzo[b]thiophene-2-carbonyl)morpholine-3-carboxylic acid

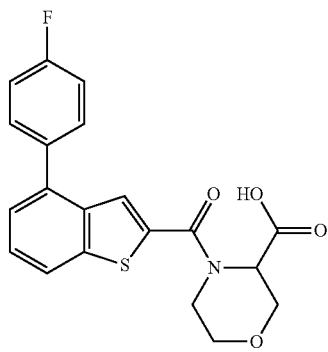 [SMILES: O=C(O)C1COCCN1C(=O)c1cc2c(-c3ccc(F)cc3)cccc2s1]

Methyl 4-(4-(4-fluorophenyl)benzo[b]thiophene-2-carbonyl)morpholine-3-carboxylate (1 eq) was dissolved in THF, to which 2 N sodium hydroxide (NaOH, 3 eq) was added, followed by stirring at 30° C. The reaction mixture was cooled down at room temperature. The reaction mixture was acidified, then washed and extracted with EtOAc. The small amount of water remaining in the organic layer was dried over anhydrous MgSO$_4$. The solvent was eliminated by vacuum distillation, followed by vacuum drying. As a result, a target compound was obtained with the yield of 59%.

1H NMR (300 MHz, DMSO-d$_6$) δ 8.00-7.85 (m, 2H), 7.59-7.27 (m, 6H), 4.32 (brs, 1H), 4.02 (brs, 1H), 3.61-3.36 (m, 4H).

<Example 9> Preparation of (4-(1H-indole-5-yl)benzo[b]thiophene-2-yl)(morpholino)methanone

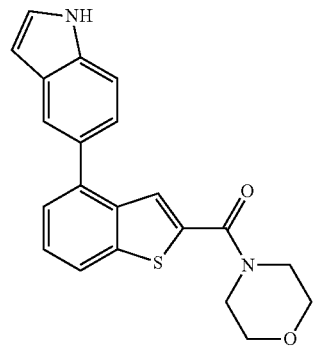 [SMILES: O=C(c1cc2c(-c3ccc4[nH]ccc4c3)cccc2s1)N1CCOCC1]

(4-bromobenzo[b]thiophene-2-yl)(morpholino)methanone (1 eq) was dissolved in dimethylene glycol ether (DME), to which Pd(PPh$_3$)$_4$ (tetrakis(triphenylphosphine) palladium (0), 0.02 eq), 1H-indole-5-ylboronic acid (1.1 eq), and 2 M sodium carbonate (2M Na$_2$CO$_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation or by crystallization using a proper solvent. As a result, a target compound was obtained with the yield of 48%.

1H NMR (300 MHz, CDCl3) δ 8.30 (brs, 1H), 7.82-7.80 (m, 2H), 7.66 (s, 1H), 7.52-7.43 (m, 3H), 7.37 (d, 1H), 7.30 (t, 1H), 6.63 (s, 1H), 3.72-3.70 (m, 8H).

<Example 10> Preparation of N-(4-(2-(morpholine-4-carbonyl)benzo[b]thiophene-4-yl)phenyl)acetamide

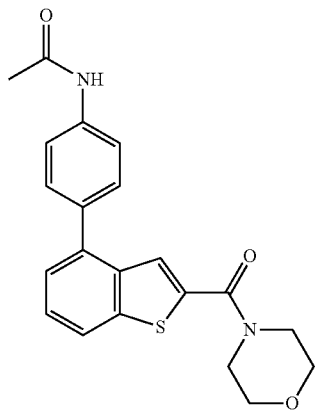 [SMILES: CC(=O)Nc1ccc(-c2cccc3sc(C(=O)N4CCOCC4)cc23)cc1]

(4-bromobenzo[b]thiophene-2-yl)(morpholine)methanone (1 eq) was dissolved in dimethylene glycol ether (DME), to which Pd(PPh$_3$)$_4$ (tetrakis(triphenylphosphine) palladium (0), 0.02 eq), 4-acetamidophenylboronic acid (1.1 eq), and 2 M sodium carbonate (2M Na$_2$CO$_3$) solution (5 eq) were added, followed by stirring at 50° C. for overnight. The reaction mixture was cooled down at room temperature,

<Example 11> Preparation of (5-hydroxy-1H-indol-2-yl)(morpholino)methanone

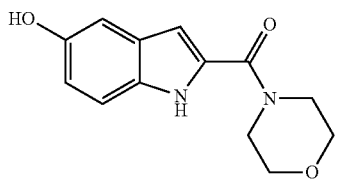 [SMILES: O=C(c1cc2cc(O)ccc2[nH]1)N1CCOCC1]

5-hydroxy-1H-indole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 43%.

1H NMR (300 MHz, DMSO-d6) δ 11.80 (s, 1H), 7.64 (s, 1H), 7.44 (d, 1H), 7.20 (d, 1H), 6.79 (s, 1H), 3.74-3.66 (m, 8H).

<Example 12> Preparation of (5-chloro-1H-indol-2-yl)(morpholino)methanone

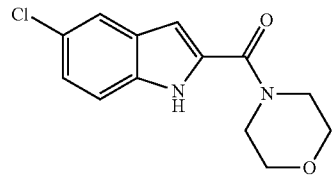 [SMILES: O=C(c1cc2cc(Cl)ccc2[nH]1)N1CCOCC1]

5-chloro-1H-indole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 61%.

1H NMR (300 MHz, DMSO-d6) δ 7.65 (d, 1H), 7.43 (d, 1H), 7.19 (dd, 1H), 6.79 (s, 1H), 3.74 (s, 4H), 3.66 (d, 4H).

<Example 13> Preparation of (5-methyl-1H-benzo[d]imidazole-2-yl)(morpholino)methanone

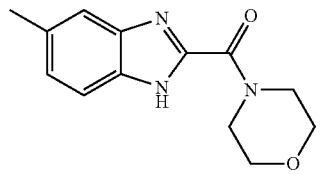 [SMILES: Cc1ccc2[nH]c(C(=O)N3CCOCC3)nc2c1]

5-methyl-1H-benzo[d]imidazole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 8%.

1H NMR (300 MHz, CDCl3) δ 7.68 (d. 1H), 7.40 (d, 1H), 7.31-7.13 (m, 2H), 3.83 (brs, 8H), 2.49 (d, 3H).

<Example 14> Preparation of (5-bromo-1H-benzo[d]imidazole-2-yl)(morpholino)methanone

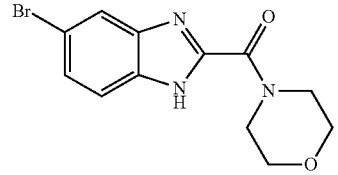

5-bromo-1H-benzo[d]imidazole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 29%.

1H NMR (300 MHz, CDCl3) δ 7.77-7.65 (m. 1H), 7.43-7.41 (m, 2H), 3.85-3.82 (m, 8H).

<Example 15> Preparation of benzofuran-2-yl(morpholino)methanone

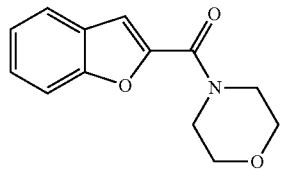 [SMILES: O=C(c1cc2ccccc2o1)N1CCOCC1]

Benzofuran-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 38%.

1H NMR (300 MHz, CDCl3) δ 7.66 (d. 1H), 7.52 (d, 1H), 7.41 (t, 1H), 7.29 (s, 1H), 7.31 (t, 1H), 3.88 (brs, 4), 3.79 (d, 4H).

<Example 16> Preparation of (5-bromobenzofuran-2-yl)(morpholino)methanone

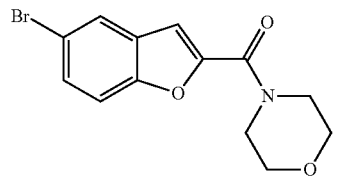

5-bromobenzofuran-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 46%.

1H NMR (300 MHz, CDCl3) δ 7.79 (d. 1H), 7.50 (dd, 1H), 7.40 (d, 1H), 7.27 (d, 1H), 3.86 (brs, 4H), 3.79 (brs, 4H).

<Example 17> Preparation of (4,6-dimethylbenzo[b]thiophene-2-yl)(morpholino)methanone

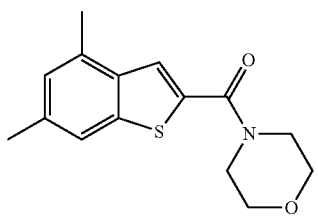 [SMILES: Cc1cc(C)c2cc(C(=O)N3CCOCC3)sc2c1]

4,6-dimethylbenzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 41%.

1H NMR (300 MHz, CDCl3) δ 7.53 (s, 1H), 7.46 (s, 1H), 7.00 (s, 1H), 3.79-3.74 (m, 8H), 2.56 (s, 3H), 2.43 (s, 3H).

<Example 18> Preparation of (6,7-dimethylbenzo[b]thiophene-2-yl)(morpholino)methanone

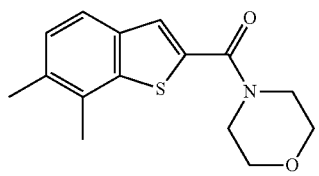 [SMILES: Cc1ccc2cc(C(=O)N3CCOCC3)sc2c1C]

6,7-dimethylbenzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 53%.

1H NMR (300 MHz, CDCl3) δ 7.56 (d, 1H), 7.45 (s, 1H), 7.22 (d, 1H), 3.81-3.74 (m, 8H), 2.47 (s, 3H), 2.42 (s, 3H).

<Example 19> Preparation of (6-methoxybenzo[b]thiophene-2-yl)(morpholino)methanone

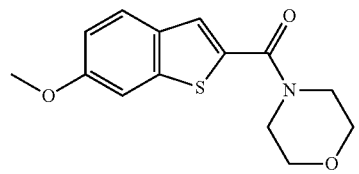 [SMILES: COc1ccc2cc(C(=O)N3CCOCC3)sc2c1]

6-methoxybenzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 33%.

1H NMR (300 MHz, DMSO-d6) δ 7.18 (d, 1H), 7.67 (s, 1H), 7.58 (s, 1H), 7.06 (d, 1H), 3.83 (s, 3H), 3.68-3.66 (m, 8H).

<Example 20> Preparation of N,N-diethyl-2-(morpholine-4-carbonyl)benzo[b]thiophene-4-carboxamide

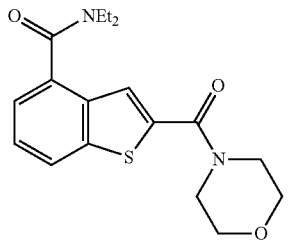

4-(diethylcarbamoyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 20%.

1H NMR (300 MHz, CDCl$_3$) δ 7.86 (d, 1H), 7.41 (t, 2H), 7.32 (d, 1H), 3.73 (s, 8H), 3.63 (d, 2H), 3.16 (s, 2H), 1.28 (t, 3H), 1.04 (d, 3H).

<Example 21> Preparation of (5-methyl-1H-indol-2-yl)(morpholino)methanone

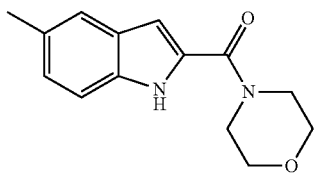 [SMILES: Cc1ccc2[nH]c(C(=O)N3CCOCC3)cc2c1]

5-methyl-1H-indole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 56%.

1H NMR (300 MHz, DMSO-d6) δ 7.35 (s, 1H), 7.28 (d, 1H), 7.02 (d, 1H), 6.70 (s, 1H), 3.73-3.64 (m, 8H), 2.36 (s, 3H).

<Example 22> Preparation of (5-methoxy-1H-indol-2-yl)(morpholino)methanone

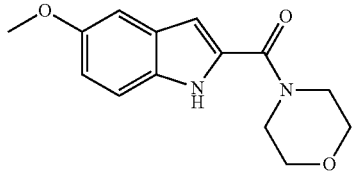 [SMILES: COc1ccc2[nH]c(C(=O)N3CCOCC3)cc2c1]

5-methoxy-1H-indole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 57%.

1H NMR (300 MHz, DMSO-d6) δ 7.32 (d, 1H), 7.05 (s, 1H), 6.85 (d, 1H), 6.71 (s, 1H), 3.74 (s, 1H), 3.64 (s, 8H).

<Example 23> Preparation of (1H-benzo[d]imidazol-2-yl)(morpholino)methanone

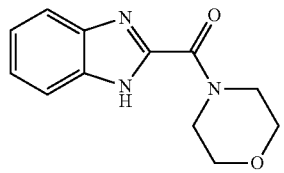 [SMILES: O=C(c1nc2ccccc2[nH]1)N1CCOCC1]

1H-benzo[d]imidazole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 22%. 1H NMR (300 MHz, CDCl3) δ 7.81 (d. 1H), 7.52 (d, 1H), 7.35 (t, 2H), 3.86-2.83 (m, 8H).

<Example 24> Preparation of (5-methoxy-1H-benzo[d]imidazol-2-yl)(morpholino)methanone

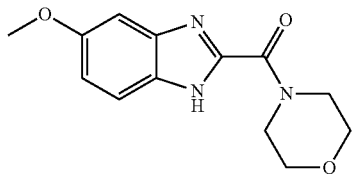 [SMILES: COc1ccc2[nH]c(C(=O)N3CCOCC3)nc2c1]

5-methoxy-1H-benzo[d]imidazole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 16%.

1H NMR (300 MHz, CDCl3) δ 7.67 (d. 1H), 6.97-6.93 (m, 2H), 3.87 (s, 3H), 3.83 (brs, 8H).

<Example 25> Preparation of (1-methyl-1H-indole-2-yl)(morpholino)methanone

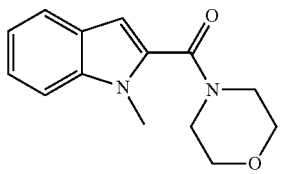 [SMILES: Cn1c(C(=O)N2CCOCC2)cc2ccccc21]

1-methyl-1H-indole-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 29%.

1H NMR (300 MHz, DMSO-d6) δ 7.59 (d, 2H), 7.50 (d, 2H), 7.23 (t, 1H), 7.07 (t, 1H), 3.74 (s, 1H), 3.62 (s, 8H).

<Example 26> Preparation of (5-methoxybenzofuran-2-yl)(morpholino)methanone

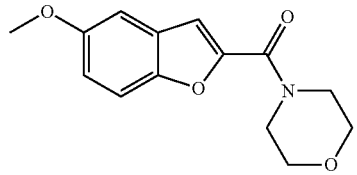 [SMILES: COc1ccc2oc(C(=O)N3CCOCC3)cc2c1]

5-methoxybenzofuran-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 50%.

1H NMR (300 MHz, CDCl3) δ 7.40 (d. 1H), 7.29 (s, 1H), 7.06 (d, 1H), 7.01 (dd, 1H), 3.87 (brs, 4H), 3.85 (s, 3H), 3.79-3.76 (m, 4H).

<Example 27> Preparation of (6-methylbenzofuran-2-yl)(morpholino)methanone

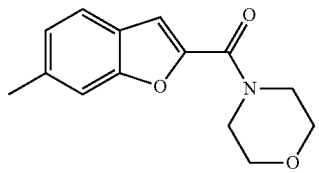 [SMILES: Cc1ccc2cc(C(=O)N3CCOCC3)oc2c1]

6-methylbenzofuran-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 58%.

1H NMR (300 MHz, CDCl3) δ 7.52 (d, 1H), 7.32 (s, 1H), 7.30 (s, 1H), 7.12 (d, 1H), 3.88 (brs, 4H), 3.79-3.78 (m, 4H), 2.49 (s, 3H).

<Example 28> Preparation of (5-aminobenzo[b]thiophene-2-yl)(morpholino)methanone

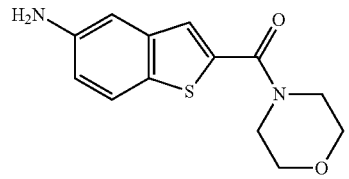 [SMILES: Nc1ccc2sc(C(=O)N3CCOCC3)cc2c1]

5-aminobenzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 38%.

1H NMR (300 MHz, DMSO-d6) δ 7.58 (d, 1H), 7.42 (s, 1H), 6.96 (s, 1H), 6.79 (d, 1H), 5.15 (s, 2H), 3.62 (s, 8H).

<Example 29> Preparation of (7-bromobenzo[b]thiophene-2-yl)(morpholino)methanone

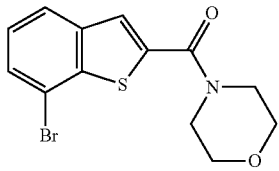 [SMILES: O=C(c1cc2cccc(Br)c2s1)N1CCOCC1]

7-bromobenzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 48%.

1H NMR (300 MHz, DMSO-d6) δ 7.95 (d, 1H), 7.90 (s, 1H), 7.70 (d, 1H), 3.66-3.65 (m, 8H).

<Example 30> Preparation of (4-(2-fluorophenyl)benzo[b]thiophene-2-yl)(morpholino)methanone

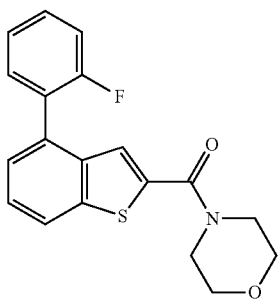 [SMILES: O=C(c1cc2c(-c3ccccc3F)cccc2s1)N1CCOCC1]

4-(2-fluorophenyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 33%.

1H NMR (300 MHz, CDCl3) δ 7.89-7.77 (m, 1H), 7.60-7.25 (m, 4H), 7.28-7.18 (m, 2H), 3.79-3.72 (m, 8H).

<Example 31> Preparation of (4-(biphenyl-4-yl)benzo[b]thiophene-2-yl)(morpholino)methanone

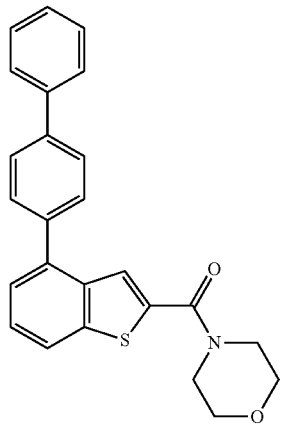 [SMILES: O=C(c1cc2c(-c3ccc(-c4ccccc4)cc3)cccc2s1)N1CCOCC1]

4-(biphenyl-4-yl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 18%.

1H NMR (300 MHz, DMSO-d6) δ 8.08 (d, 2H), 7.85 (d, 2H), 7.77 (d, 2H), 7.71 (d, 2H), 7.66 (s, 1H), 7.59-7.48 (m, 3H), 7.42-7.38 (m, 1H), 3.64-3.62 (m, 8H).

<Example 32> Preparation of morpholino(4-p-tolyl-benzo[b]thiophene-2-yl)methanone

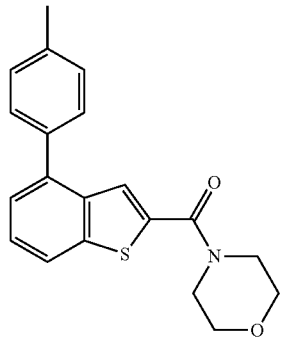 [SMILES: Cc1ccc(-c2cccc3sc(C(=O)N4CCOCC4)cc23)cc1]

(4-bromobenzo[b]thiophene-2-yl)(morpholino)methanone (1 eq) was dissolved in dimethylene glycol ether (DME), to which $Pd(PPh_3)_4$ (tetrakis(triphenylphosphine) palladium (0), 0.02 eq), p-tolylboronic acid (1.1 eq), and 2 M sodium carbonate (2M $Na_2CO_3$) solution (5 eq) were added, followed by stirring at 50° C. for overnight. The reaction mixture was cooled down at room temperature, which was then passed through celite for filtration. The filtrate was washed and extracted with water and EtOAc.

The small amount of water remaining in the organic layer was dried over anhydrous MgSO4. The solvent was eliminated by vacuum distillation, followed by column separation. As a result, a target compound was obtained with the yield of 56%.

1H NMR (300 MHz, CDCl3) δ 7.80 (t, 1H), 7.60 (s, 1H), 7.48-7.43 (m, 2H), 7.35 (d, 1H), 7.31-7.23 (m, 2H), 3.79-3.72 (m, 8H), 2.44 (s, 3H).

<Example 33> Preparation of 4-(2-(morpholine-4-carbonyl)benzo[b]thiophene-4-yl)benzoic acid

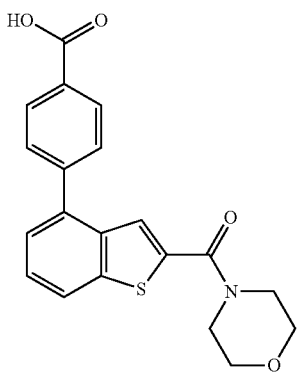 [SMILES: O=C(O)c1ccc(-c2cccc3sc(C(=O)N4CCOCC4)cc23)cc1]

(4-bromobenzo[b]thiophene-2-yl)(morpholino)methanone (1 eq) was dissolved in dimethylene glycol ether (DME), to which Pd(PPh3)4 (tetrakis(triphenylphosphine) palladium (0), 0.02 eq), 4-boronobenzoic acid (1.1 eq), and 2 M sodium carbonate (2M Na2CO3) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 57%.

1H NMR (300 MHz, DMSO-d6) δ 8.10-7.93 (m, 3H), 7.57 (s, 1H), 7.53-7.39 (m, 4H), 3.60-3.58 (m, 8H).

<Example 34> Preparation of (4-(4-methoxyphenyl)benzo[b]thiophene-2-yl)(morpholino)methanone

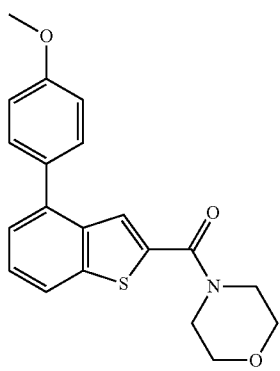 [SMILES: COc1ccc(-c2cccc3sc(C(=O)N4CCOCC4)cc23)cc1]

(4-bromobenzo[b]thiophene-2-yl)(morpholino)methanone (1 eq) was dissolved in dimethylene glycol ether (DME), to which Pd(PPh3)4 (tetrakis(triphenylphosphine) palladium (0), 0.02 eq), 4-methoxyphenylboronic acid (1.1 eq), and 2 M sodium carbonate (2M Na2CO3) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 50%.

1H NMR (300 MHz, CDCl3) δ 7.81 (d, 1H). 7.60 (s, 1H), 7.48 (m, 3H), 7.35 (d, 1H), 7.02 (d, 2H), 3.88 (s, 3H), 3.74-3.72 (m, 8H).

<Example 35> Preparation of (4-(4-fluorophenyl)benzo[b]thiophene-2-yl)(pyrrolidine-1-yl)methanone 4-(4-fluorophenyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO4. The solvent was eliminated by vacuum distillation, followed by vacuum drying. Then, a target compound was obtained by column separation with the yield of 23%.

1H NMR (300 MHz, CDCl3) δ 7.84 (d, 1H), 7.74 (s, 1H), 7.53-7.43 (m, 3H), 7.32 (d, 1H), 7.17 (t, 2H), 3.70 (t, 4H), 1.97 (s, 4H).

\<Example 36\> Preparation of (4-(3-fluorophenyl) benzo[b]thiophene-2-yl)(morpholino)methanone

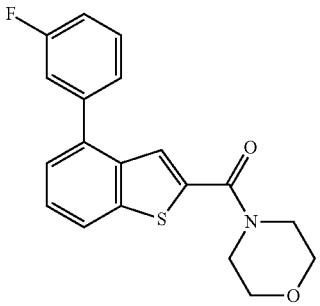 [SMILES: O=C(c1cc2c(-c3cccc(F)c3)cccc2s1)N1CCOCC1]

(4-bromobenzo[b]thiophene-2-yl)(morpholino)methanone (1 eq) was dissolved in dimethylene glycol ether (DME), to which Pd(PPh₃)₄ (tetrakis(triphenylphosphine)palladium (0), 0.02 eq), 3-fluorophenylboronic acid (1.1 eq), and 2 M sodium carbonate (2M $Na_2CO_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 53%.

1H NMR (300 MHz, CDCl3) δ 7.87 (d, 1H), 7.57 (s, 1H), 7.50-7.30 (m, 4H), 7.22-7.10 (m, 2H), 3.74-3.73 (m, 8H).

\<Example 37\> Preparation of (4-aminopiperidine-1-yl) (4-(4-fluorophenyl)benzo[b]thiophene-2-yl)methanone hydrochloride

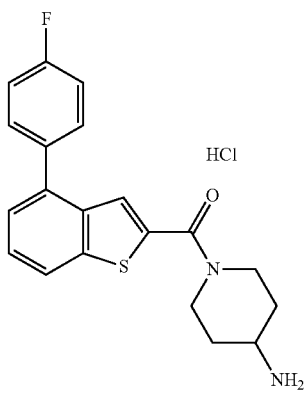 [SMILES: NC1CCN(C(=O)c2cc3c(-c4ccc(F)cc4)cccc3s2)CC1 ; Cl]

4-(4-fluorophenyl)benzo[b]thiophene-2-carboxylic acid (1 eq) was dissolved in DMF, to which piperidine-4-amine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 51%.

1H NMR (300 MHz, DMSO-d6) δ 8.08 (d, 1H), 7.68-7.63 (m, 2H), 7.58-7.51 (m, 2H), 7.45-7.33 (m, 3H), 4.26 (brs, 2H), 3.30 (brs, 1H), 3.06-2.96 (m, 2H), 2.72-2.71 (m, 2H), 2.01-1.98 (m, 2H), 1.50-1.47 (m, 2H).

\<Example 38\> Preparation of (4-(4-fluorophenyl) benzo[b]thiophene-2-yl)(piperazine-1-yl)methanone hydrochloride

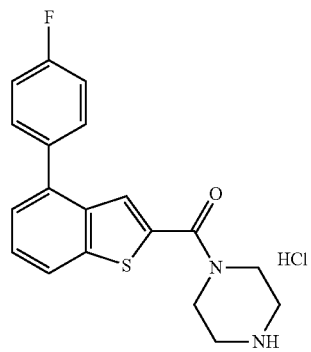 [SMILES: O=C(c1cc2c(-c3ccc(F)cc3)cccc2s1)N1CCNCC1 ; Cl]

4-(4-fluorophenyl)benzo[b]thiophene-2-carboxylic acid (1 eq) was dissolved in DMF, to which piperazine hydrochloride (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 51%.

1H NMR (300 MHz, DMSO-d6) δ 9.03 (brs, 1H), 8.07 (d, 1H), 7.67-7.57 (m, 2H), 7.54-7.51 (m, 1H), 7.44-7.32 (m, 2H), 3.83 (s, 2H), 3.38 (s, 2H), 3.15 (s, 2H), 2.48 (s, 2H).

\<Example 39\> Preparation of (4-(4-fluorophenyl) benzo[b]thiophene-2-yl)(morpholino)methanone

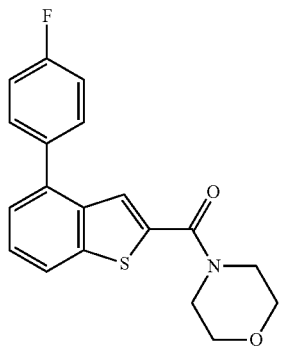 [SMILES: O=C(c1cc2c(-c3ccc(F)cc3)cccc2s1)N1CCOCC1]

4-(4-fluorophenyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 89%.

1H NMR (300 MHz, DMSO-d6) δ 8.08 (d, 1H), 7.67-7.63 (m, 2H), 7.57-7.52 (m, 2H), 7.45 (d, 1H), 7.40-7.34 (m, 2H), 3.64-3.62 (m, 8H).

<Example 40> Preparation of (5-(4-fluorophenyl) benzo[b]thiophene-2-yl)(morpholino)methanone

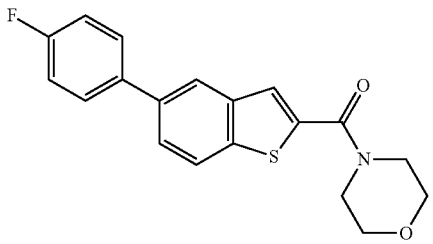 [SMILES: O=C(c1cc2cc(-c3ccc(F)cc3)ccc2s1)N1CCOCC1]

(5-bromobenzo[b]thiophene-2-yl)(morpholino)methanone (1 eq) was dissolved in dimethylene glycol ether (DME), to which Pd(PPh₃)₄ (tetrakis(triphenylphosphine) palladium (0), 0.02 eq), 4-fluorophenylboronic acid (1.1 eq), and 2 M sodium carbonate (2M Na₂CO₃) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 52%.

1H NMR (300 MHz, CDCl3) δ 7.94 (s, 1H), 7.91 (d, 1H), 7.61-7.56 (m, 3H), 7.52 (s, 1H), 7.18-7.12 (m, 2H), 3.79-3.70 (m, 8H).

<Example 41> Preparation of (4-(biphenyl-3-yl) benzo[b]thiophene-2-yl)(morpholino)methanone

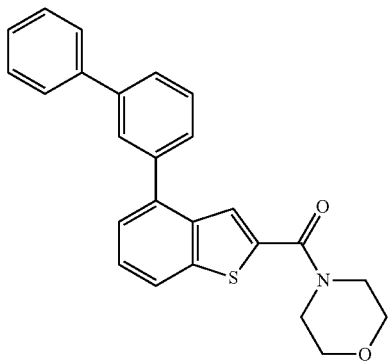 [SMILES: O=C(c1cc2c(-c3cccc(-c4ccccc4)c3)cccc2s1)N1CCOCC1]

4-(biphenyl-3-yl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 21%.

1H NMR (300 MHz, CDCl3) δ 7.86 (d, 1H), 7.76 (s, 1H), 7.62 (t, 5H), 7.57-7.37 (m, 6H), 3.74 (t, 8H).

<Example 42> Preparation of (4-(3-aminophenyl) benzo[b]thiophene-2-yl)(morpholino)methanone

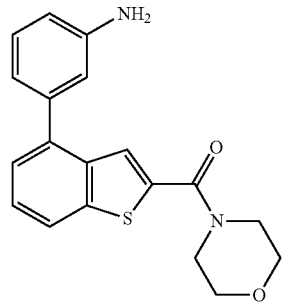 [SMILES: Nc1cccc(-c2cccc3sc(C(=O)N4CCOCC4)cc23)c1]

4-(3-aminophenyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 10%.

1H NMR (300 MHz, DMSO-d6) δ 8.01 (d, 1H), 7.60 (s, 1H), 7.51 (t, 1H), 7.38 (d, 1H), 7.15 (t, 1H), 6.76-6.62 (m, 3H), 3.63 (m, 8H).

<Example 43> Preparation of 4-(2-(morpholine-4-carbonyl)benzo[b]thiophene-4-yl)benzamide

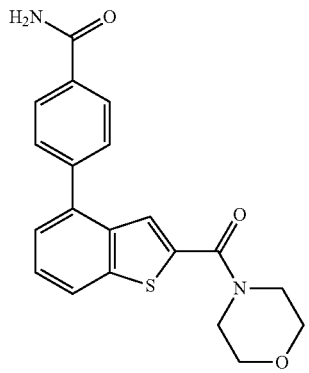 [SMILES: NC(=O)c1ccc(-c2cccc3sc(C(=O)N4CCOCC4)cc23)cc1]

(4-bromobenzo[b]thiophene-2-yl)(morpholino)methanone (1 eq) was dissolved in dimethylene glycol ether (DME), to which Pd(PPh₃)₄ (tetrakis(triphenylphosphine) palladium (0), 0.02 eq), 4-carbamoylphenylboronic acid (1.1 eq), and 2 M sodium carbonate (2M Na₂CO₃) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 50%.

1H NMR (300 MHz, DMSO-d6) δ 8.11-8.08 (m, 2H), 8.05 (d, 2H), 7.70 (d, 2H), 7.60 (s, 1H), 7.57 (d, 1H), 7.50-7.46 (m, 2H), 3.64-3.62 (m, 8H).

<Example 44> Preparation of (4-(4-hydroxyphenyl) benzo[b]thiophene-2-yl)(morpholino)methanone

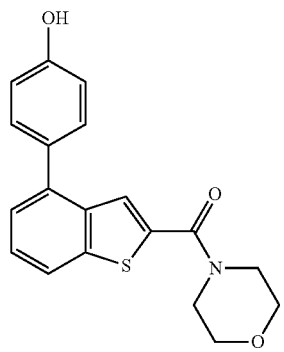

(4-bromobenzo[b]thiophene-2-yl)(morpholino)methanone (1 eq) was dissolved in dimethylene glycol ether (DME), to which Pd(PPh₃)₄ (tetrakis(triphenylphosphine) palladium (0), 0.02 eq), 4-hydroxyphenylboronic acid (1.1 eq), and 2 M sodium carbonate (2M Na₂CO₃) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 35%.

1H NMR (300 MHz, CDCl3) δ 7.81 (d, 1H), 7.60 (s, 1H), 7.46-7.29 (m, 4H), 6.95 (d, 2H), 3.73-3.72 (m, 8H).

<Example 45> Preparation of morpholino(4-(4-(trifluoromethoxy)phenyl)benzo[b]thiophene-2-yl) methanone

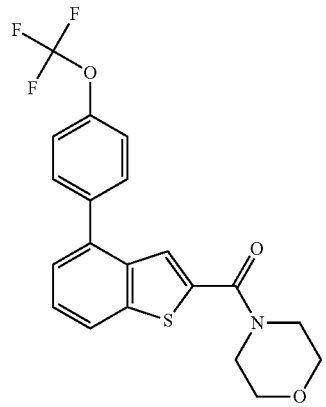 [SMILES: O=C(c1cc2c(-c3ccc(OC(F)(F)F)cc3)cccc2s1)N1CCOCC1]

(4-bromobenzo[b]thiophene-2-yl)(morpholino)methanone (1 eq) was dissolved in dimethylene glycol ether (DME), to which Pd(PPh₃)₄ (tetrakis(triphenylphosphine) palladium (0), 0.02 eq), 4-(trifluoromethoxy)phenylboronic acid (1.1 eq), and 2 M sodium carbonate (2M Na₂CO₃) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 46%.

1H NMR (300 MHz, CDCl3) δ 7.86 (d, 1H), 7.57-7.54 (m, 3H), 7.48 (t, 1H), 7.37-7.32 (m, 3H), 3.73-3.72 (m, 8H).

<Example 46> Preparation of (4-(4-fluorophenyl) benzo[b]thiophene-2-yl) (oxazolidine-3-yl)methanone

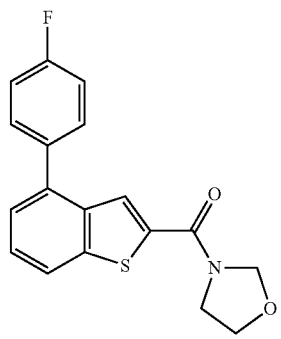 [SMILES: O=C(c1cc2c(-c3ccc(F)cc3)cccc2s1)N1CCOC1]

4-(4-fluorophenyl)benzo[b]thiophene-2-carboxylic acid (1 eq) was dissolved in DMF, to which oxazolidine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 37%.

1H NMR (300 MHz, CDCl3) δ 7.84-7.80 (m, 1H), 7.65 (s, 1H), 7.51 (m, 3H), 7.33 (d, 1H), 7.16 (t, 2H), 3.86 (brs, 2H), 3.71 (t, 2H), 3.24 (brs, 2H).

<Example 47> Preparation of (4-(4-fluorophenyl) benzo[b]thiophene-2-yl) (piperidine-1-yl)methanone

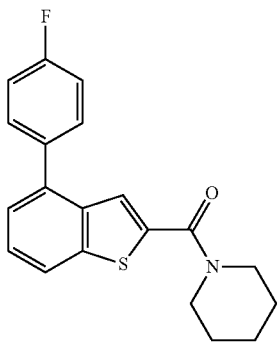 [SMILES: O=C(c1cc2c(-c3ccc(F)cc3)cccc2s1)N1CCCCC1]

4-(4-fluorophenyl)benzo[b]thiophene-2-carboxylic acid (1 eq) was dissolved in DMF, to which piperidine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 23%.

1H NMR (300 MHz, DMSO-d6) δ 7.84 (d, 1H), 7.53-7.42 (m, 4H), 7.34-7.32 (m, 1H), 7.20-7.14 (m, 2H), 3.65 (s, 4H), 1.68 (m, 6H).

<Example 48> Preparation of (4-(4-fluorophenyl) benzo[b]thiophene-2-yl)(4-hydroxypiperidine-1-yl) methanone

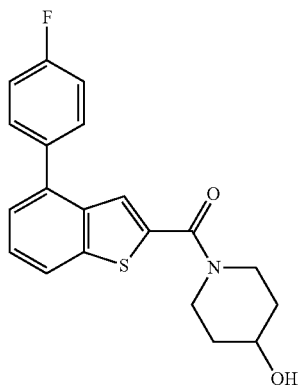 [SMILES: O=C(c1cc2c(-c3ccc(F)cc3)cccc2s1)N1CCC(O)CC1]

4-(4-fluorophenyl)benzo[b]thiophene-2-carboxylic acid (1 eq) was dissolved in DMF, to which piperidine-4-ol (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 56%.

1H NMR (300 MHz, CDCl3) δ 7.84 (d, 1H), 7.52-7.42 (m, 4H), 7.35 (d, 1H), 7.19-7.14 (m, 2H), 4.01-4.00 (m, 3H), 3.46-3.37 (m, 2H), 1.91 (brs, 2H), 1.57-1.51 (m, 2H).

<Example 49> Preparation of (4-(4-fluorophenyl) benzo[b]thiophene-2-yl)(4-methylpiperazine-1-yl) methanone hydrochloride

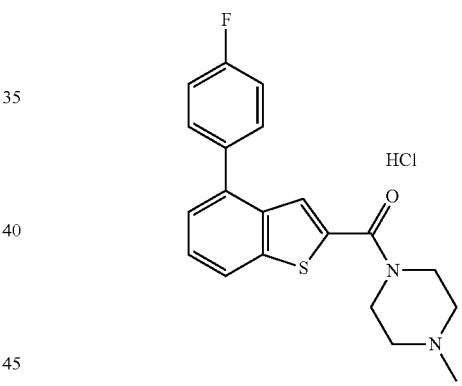

4-(4-fluorophenyl)benzo[b]thiophene-2-carboxylic acid (1 eq) was dissolved in DMF, to which 1-methylpiperazine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 45%.

1H NMR (300 MHz, DMSO-d6) δ 8.08 (d, 1H), 7.68-7.53 (m, 4H), 7.45-7.33 (m, 3H), 3.31 (s, 8H), 2.75 (s, 3H).

<Example 50> Preparation of (4-(4-(methylthio)phenyl)benzo[b]thiophene-2-yl)(morpholino)methanone

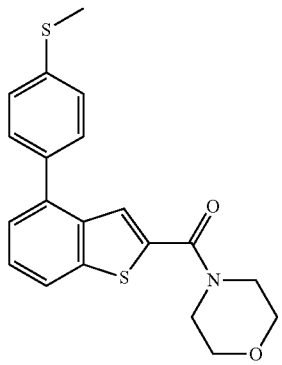 [SMILES: CSc1ccc(-c2cccc3sc(C(=O)N4CCOCC4)cc23)cc1]

(4-bromobenzo[b]thiophene-2-yl)(morpholino)methanone (1 eq) was dissolved in dimethylene glycol ether (DME), to which Pd(PPh$_3$)$_4$ (tetrakis(triphenylphosphine) palladium (0), 0.02 eq), 4-(methylthio)phenylboronic acid (1.1 eq), and 2 M sodium carbonate (2M Na$_2$CO$_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 51%.

1H NMR (300 MHz, CDCl3) δ 7.83 (d, 1H), 7.60-7.58 (m, 1), 7.49-7.44 (m, 3H), 7.38 (s, 2), 7.35 (s, 1H), 3.79-3.72 (m, 8H), 2.55 (s, 3H).

<Example 51> Preparation of (4-(4-fluorophenyl)benzo[b]thiophene-2-yl)(thiomorpholino)methanone

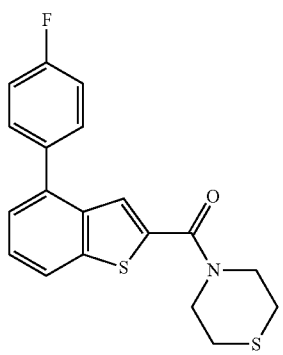 [SMILES: O=C(c1cc2c(-c3ccc(F)cc3)cccc2s1)N1CCSCC1]

4-(4-fluorophenyl)benzo[b]thiophene-2-carboxylic acid (1 eq) was dissolved in DMF, to which thiomorpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 26%.

1H NMR (300 MHz, DMSO-d6) δ 8.06 (d, 1H), 7.67-7.62 (m, 2H), 7.56-7.51 (m, 2H), 7.44-7.33 (m, 4H), 3.87-3.84 (m, 4H), 2.67-2.65 (m, 4H).

<Example 52> Preparation of (4-(4-fluorophenyl)benzo[b]thiophene-2-yl) (1,4-oxazepane-4-yl)methanone

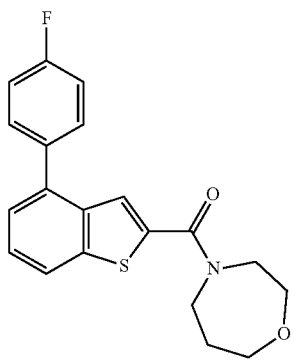 [SMILES: O=C(c1cc2c(-c3ccc(F)cc3)cccc2s1)N1CCCOCC1]

4-(4-fluorophenyl)benzo[b]thiophene-2-carboxylic acid (1 eq) was dissolved in DMF, to which 1,4-oxazepane (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 36%.

1H NMR (300 MHz, CDCl3) δ 7.85 (d, 1H), 7.56-7.43 (m, 4H), 7.35-7.33 (m, 1H), 7.20-7.14 (m, 2H), 3.89-3.77 (m, 10H).

<Example 53> Preparation of (7-chloro-4-(4-fluorophenyl)benzo[b]thiophene-2-yl)(morpholino)methanone

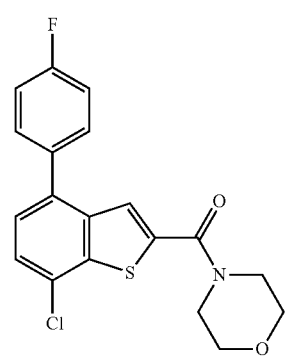 [SMILES: O=C(c1cc2c(-c3ccc(F)cc3)ccc(Cl)c2s1)N1CCOCC1]

7-chloro-4-(4-fluorophenyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 25%.

1H NMR (300 MHz, CDCl3) δ 7.56 (s, 1H), 7.48 (t, 2H), 7.45 (d, 1H), 7.31 (d, 1H), 7.18 (t, 2H), 3.73 (s, 8H).

<Example 54> Preparation of (4-(4-bromophenyl)benzo[b]thiophene-2-yl)(morpholino)methanone

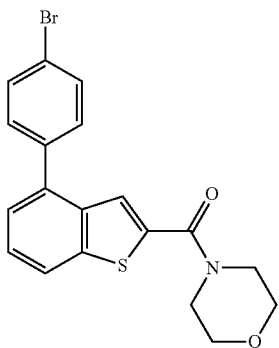

(4-bromobenzo[b]thiophene-2-yl)(morpholino)methanone (1 eq) was dissolved in dimethylene glycol ether (DME), to which Pd(PPh₃)₄ (tetrakis(triphenylphosphine) palladium (0), 0.02 eq), 4-bromophenylboronic acid (1.1 eq), and 2 M sodium carbonate (2M Na₂CO₃) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 27%.

1H NMR (300 MHz, CDCl3) δ 7.85 (d, 1H), 7.62 (d, 2H), 7.53 (s, 1H), 7.47 (t, 1H), 7.41 (d, 2H), 7.35 (d, 1H), 3.73 (s, 8H).

<Example 55> Preparation of (4-(6-methoxypyridine-3-yl)benzo[b]thiophene-2-yl)(morpholino)methanone

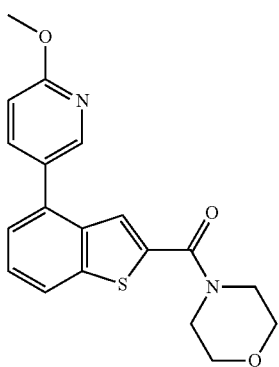 [SMILES: COc1ccc(-c2cccc3sc(C(=O)N4CCOCC4)cc23)cn1]

(4-bromobenzo[b]thiophene-2-yl)(morpholino)methanone (1 eq) was dissolved in dimethylene glycol ether (DME), to which Pd(PPh₃)₄ (tetrakis(triphenylphosphine) palladium (0), 0.02 eq), 6-methoxypyridine-3-ylboronic acid (1.1 eq), and 2 M sodium carbonate (2M Na₂CO₃) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 31%.

1H NMR (300 MHz, CDCl3) δ 8.33 (s. 1H), 7.85 (d, 1H), 7.75 (dd, 1H), 7.53 (s, 1H), 7.48 (t, 1H), 7.34 (d, 1H), 6.88 (d, 1H), 4.01 (s, 3H), 3.73 (d, 8H).

<Example 56> Preparation of (4-(3-fluorobenzyl)benzo[b]thiophene-2-yl)(morpholino)methanone

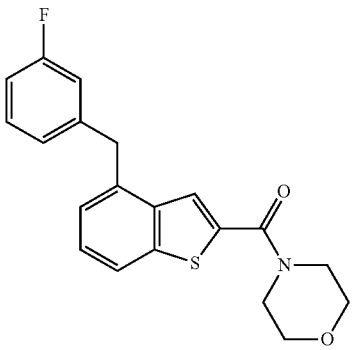 [SMILES: O=C(c1cc2c(Cc3cccc(F)c3)cccc2s1)N1CCOCC1]

4-(3-fluorobenzyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 31%.

1H NMR (300 MHz, CDCl3) δ 7.80 (d, 1H), 7.42 (q, 2H), 7.26 (t, 2H), 7.00 (d, 1H), 6.91 (q, 2H), 4.33 (s, 2H), 3.72 (s, 8H).

<Example 57> Preparation of (4-(2,4-difluorobenzyl)benzo[b]thiophene-2-yl)(morpholino)methanone

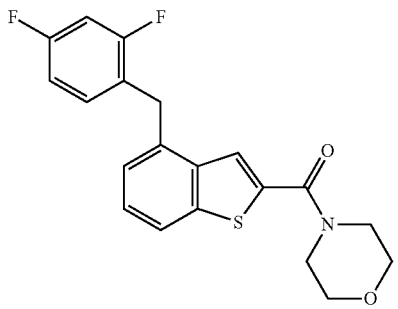 [SMILES: O=C(c1cc2c(Cc3ccc(F)cc3F)cccc2s1)N1CCOCC1]

4-(2,4-difluorobenzyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 17%.

1H NMR (300 MHz, CDCl3) δ 7.75 (d, 1H), 7.52 (s, 1H), 7.35 (t, 1H), 7.17 (d, 1H), 6.99 (t, 1H), 6.85-6.73 (m, 2H), 4.26 (s, 2H), 3.73 (s, 8H).

<Example 58> Preparation of (4-(2,4-difluorophenylamino)benzo[b]thiophene-2-yl)(morpholino)methanone

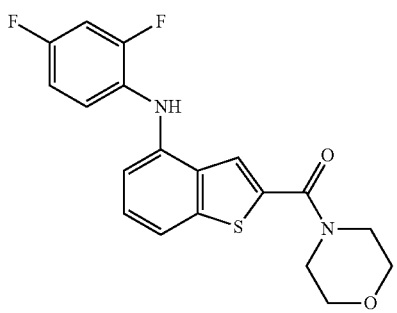 [SMILES: O=C(c1cc2c(Nc3ccc(F)cc3F)cccc2s1)N1CCOCC1]

4-(2,4-difluorophenylamino)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 22%.

1H NMR (300 MHz, CDCl3) δ 7.50 (d, 2H), 7.31 (t, 1H), 7.15-7.07 (m, 1H), 7.04 (d, 1H), 6.96-6.90 (td, 1H), 6.80 (t, 1H), 5.87 (s, 1H), 3.75 (d, 8H). 22%

<Example 59> Preparation of (4-(4-fluorophenoxy)benzo[b]thiophene-2-yl)(morpholino)methanone

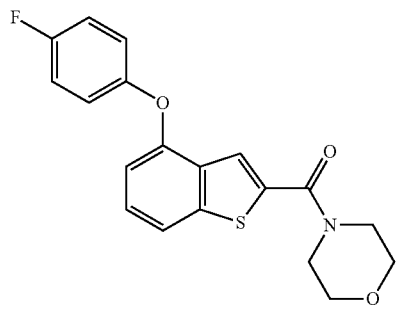 [SMILES: O=C(c1cc2c(Oc3ccc(F)cc3)cccc2s1)N1CCOCC1]

4-(4-fluorophenoxy)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 52%.

1H NMR (300 MHz, CDCl3) δ 7.57 (d, 2H), 7.30 (t, 1H), 7.06-7.03 (m, 4H), 6.74 (d, 1H), 3.79-3.73 (m, 8H).

<Example 60> Preparation of (4-(4-fluorophenethyl)benzo[b]thiophene-2-yl)(morpholino)methanone

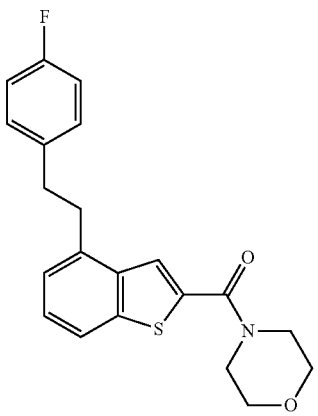 [SMILES: O=C(c1cc2c(CCc3ccc(F)cc3)cccc2s1)N1CCOCC1]

4-(4-fluorophenethyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 9%.

1H NMR (300 MHz, CDCl3) δ 7.57 (s, 1H), 7.41 (d, 1H), 7.34-7.10 (m, 4H), 7.01 (t, 1H), 6.74 (d, 1H), 4.30 (t, 2H), 3.77 (d, 3H), 3.16 (t, 2H).

<Example 61> Preparation of (4-(4-fluorobenzyloxy)benzo[b]thiophene-2-yl)(morpholino)methanone

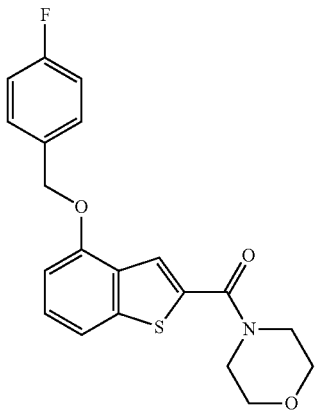 [SMILES: O=C(c1cc2c(OCc3ccc(F)cc3)cccc2s1)N1CCOCC1]

4-(4-fluorobenzyloxy)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 60%.

1H NMR (300 MHz, CDCl₃) δ 7.69 (s, 1H), 7.45 (m, 3H), 7.34 (t, 1H), 7.11 (m, 2H), 6.85 (d, 1H), 5.19 (s, 2H), 3.80 (m, 8H).

<Example 62> Preparation of (4-(4-fluorobenzylsulfonyl)benzo[b]thiophene-2-yl)(morpholino)methanone

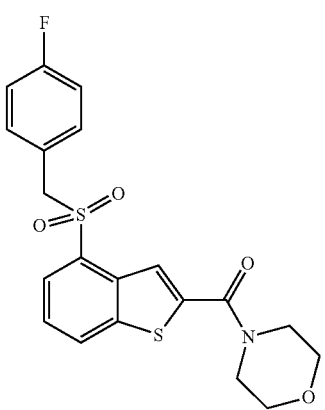 [SMILES: O=C(c1cc2c(S(=O)(=O)Cc3ccc(F)cc3)cccc2s1)N1CCOCC1]

4-(4-fluorobenzylsulfonyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO₄. The solvent was eliminated by vacuum distillation, followed by vacuum drying. Then, a target compound was obtained by column separation with the yield of 60.5%.

1H NMR (300 MHz, CDCl₃) δ 8.14 (d, 1H), 7.84 (s, 1H), 7.79 (d, 1H), 7.48 (t, 1H), 6.93 (m, 4H), 4.37 (s, 2H), 3.76 (s, 6H).

<Example 63> Preparation of (4-(2,4-difluorophenyl)benzo[b]thiophene-2-yl)(morpholino)methanone

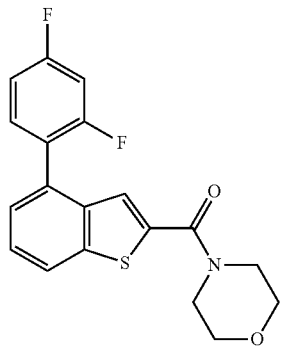 [SMILES: O=C(c1cc2c(-c3ccc(F)cc3F)cccc2s1)N1CCOCC1]

(4-bromobenzo[b]thiophene-2-yl)(morpholino)methanone (1 eq) was dissolved in dimethylene glycol ether (DME), to which Pd(PPh₃)₄ (tetrakis(triphenylphosphine) palladium (0), 0.02 eq), 2,4-difluorophenylboronic acid (1.1 eq), and 2 M sodium carbonate (2M Na₂CO₃) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 51%.

1H NMR (300 MHz, CDCl3) δ 7.89 (d, 1H), 7.79 (d, 1H), 7.60-7.55 (m, 1H), 7.50-7.23 (m, 4H), 3.79-3.72 (m, 8H).

<Example 64> Preparation of methyl 4-(2-(morpholine-4-carbonyl)benzo[b]thiophene-4-yl)benzene sulfinate

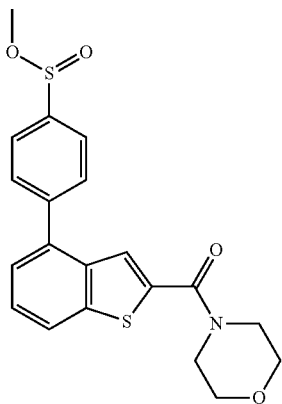 [SMILES: COS(=O)c1ccc(-c2cccc3sc(C(=O)N4CCOCC4)cc23)cc1]

(4-bromobenzo[b]thiophene-2-yl)(morpholino)methanone (1 eq) was dissolved in dimethylene glycol ether (DME), to which Pd(PPh$_3$)$_4$ (tetrakis(triphenylphosphine) palladium (0), 0.02 eq), 4-(methoxysulfinyl)phenylboronic acid (1.1 eq), and 2 M sodium carbonate (2M Na$_2$CO$_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 66%.

1H NMR (300 MHz, CDCl3) δ 8.07 (d, 2H), 7.91 (d, 1H), 7.74 (d, 2H), 7.53-7.75 (m, 2H), 7.40 (d, 1H), 3.73 (brs, 8H), 3.14 (s, 3H).

<Example 65> Preparation of (7-(4-fluorophenyl)benzo[b]thiophene-2-yl)(morpholino)methanone

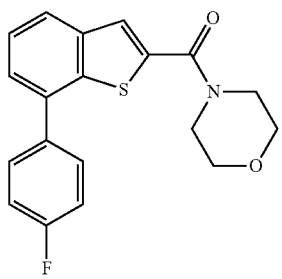 [SMILES: O=C(c1cc2cccc(-c3ccc(F)cc3)c2s1)N1CCOCC1]

7-(4-fluorophenyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 36%.

1H NMR (300 MHz, DMSO-d6) δ 7.93 (d, 1H), 7.82 (s, 1H), 7.76-7.19 (m, 2H), 7.54 (t, 1H), 7.48 (d, 1H), 7.40-7.34 (m, 2H), 3.65-3.63 (m, 8H).

<Example 66> Preparation of (4-(6-fluoropyridine-3-yl)benzo[b]thiophene-2-yl)(morpholino)methanone hydrochloride

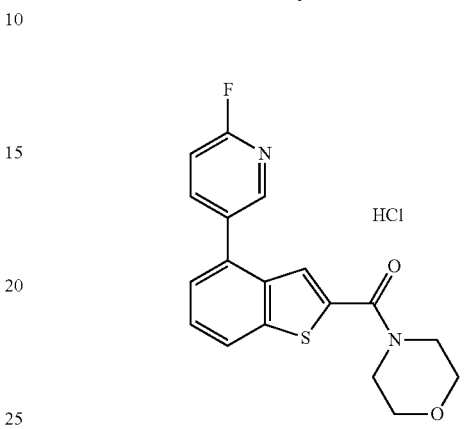

(4-bromobenzo[b]thiophene-2-yl)(morpholino)methanone (1 eq) was dissolved in dimethylene glycol ether (DME), to which Pd(PPh$_3$)$_4$ (tetrakis(triphenylphosphine) palladium (0), 0.02 eq), 6-fluoropyridine-3-ylboronic acid hydrochloride (1.1 eq), and 2 M sodium carbonate (2M Na$_2$CO$_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 54%.

8.39 (s, 1H), 7.99-7.89 (m, 2H), 7.53-7.47 (m, 2H), 7.37 (d, 1H), 7.10 (d, 1H), 3.73 (s, 8H).

<Example 67> Preparation of (4-(4-fluorobenzyl)benzo[b]thiophene-2-yl)(morpholino)methanone

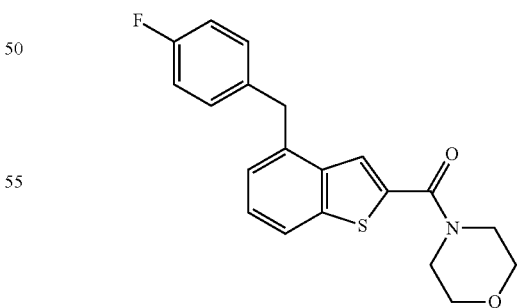

4-(4-fluorobenzyl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 51%.

1H NMR (300 MHz, CDCl3) δ 7.74 (d, 1H), 7.42 (s, 1H), 7.35 (t, 1H), 7.18-7.10 (m, 4H), 6.95 (t, 1H), 4.27 (s, 2H), 3.68 (s, 8H).

<Example 68> Preparation of (4-(4-fluorophenylamino)benzo[b]thiophene-2-yl)(morpholino)methanone

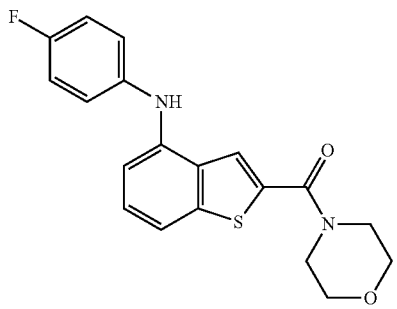 [SMILES: O=C(c1cc2c(Nc3ccc(F)cc3)cccc2s1)N1CCOCC1]

4-(4-fluorophenylamino)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 26%.

1H NMR (300 MHz, CDCl3) δ 7.48 (s, 1H), 7.43 (d, 1H), 7.29 (d, 1H), 7.01 (dd, 4H), 5.94 (s, 1H), 3.74 (d, 8H).

<Example 69> Preparation of (4-((4-fluorophenyl)(methyl)amino)benzo[b]thiophene-2-yl)(morpholino)methanone

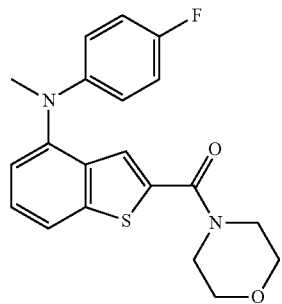 [SMILES: CN(c1ccc(F)cc1)c1cccc2sc(C(=O)N3CCOCC3)cc12]

(4-(4-fluorophenylamino)benzo[b]thiophene-2-yl)(morpholino)methanone (1 eq) was dissolved in THF, to which sodium hydride (NaH, 1.1 eq) was added at 0° C., followed by stirring. Methyl iodide (MeI, 1.1 eq) was added to the reaction mixture, followed by stirring at room temperature for overnight. The reaction mixture was washed and extracted with water and EtOAc. The small amount of water remaining in the organic layer was dried over anhydrous MgSO4. The solvent was eliminated by vacuum distillation, followed by column separation. As a result, a target compound was obtained with the yield of 69%.

1H NMR (300 MHz, CDCl3) δ 7.61 (d, 1H), 7.41 (t, 1H), 7.14 (d, 1H), 6.99 (s, 1H), 6.91 (t, 2H), 6.77 (q, 2H), 3.62 (s, 8H), 3.39 (s, 3H).

<Example 70> Preparation of 4-fluoro-N-(2-(morpholine-4-carbonyl)benzo[b]thiophene-4-yl)benzenesulfonamide

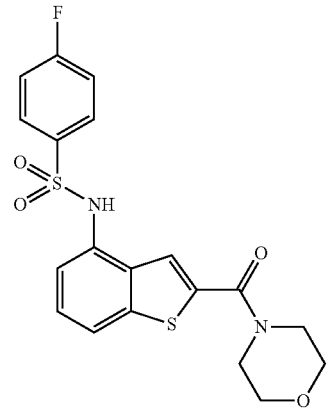 [SMILES: O=C(c1cc2c(NS(=O)(=O)c3ccc(F)cc3)cccc2s1)N1CCOCC1]

4-(4-fluorophenylsulfonamide)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 19%.

1H NMR (300 MHz, CDCl3) δ 8.00 (s. 1H), 7.71 (s, 1H), 7.66-7.60 (m, 3H), 7.29 (d, 1H), 7.17 (d, 1H), 6.93 (t, 2H), 3.74 (brs, 8H).

<Example 71> Preparation of (4-(4-fluorobenzylthio)benzo[b]thiophene-2-yl)(morpholino)methanone

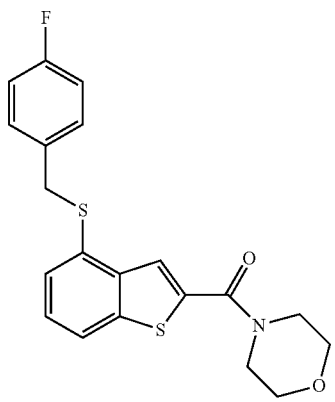 [SMILES: O=C(c1cc2c(SCc3ccc(F)cc3)cccc2s1)N1CCOCC1]

4-(4-fluorobenzylthio)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous $MgSO_4$. The solvent was eliminated by vacuum distillation, followed by vacuum drying. Then, a target compound was obtained by column separation with the yield of 58.8%.

1H NMR (300 MHz, $CDCl_3$) δ 7.75 (d, 1H), 7.63 (s, 1H), 7.33 (d, 2H), 7.16 (t, 2H), 6.93 (t, 2H), 4.12 (s, 2H), 3.77 (d, 8H).

<Example 72> Preparation of 1-methyl-5-(2-(morpholine-4-carbonyl)benzo[b]thiophene-4-yl)-1H-pyrrole-2-carbonitrile

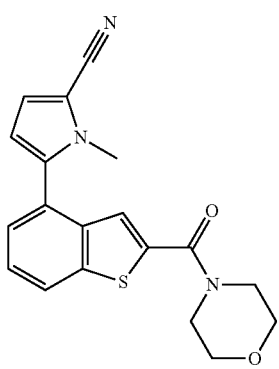 [SMILES: Cn1c(C#N)ccc1-c1cccc2sc(C(=O)N3CCOCC3)cc12]

(4-bromobenzo[b]thiophene-2-yl)(morpholino)methanone (1 eq) was dissolved in dimethylene glycol ether (DME), to which $Pd(PPh_3)_4$ (tetrakis(triphenylphosphine) palladium (0), 0.02 eq), 5-cyano-1-methyl-1H-pyrrole-2-ylboronic acid (1.1 eq), and 2 M sodium carbonate (2M $Na_2CO_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 39%.

1H NMR (300 MHz, CDCl3) δ 7.93 (d, 1H), 7.49 (t, 1H), 7.36-7.31 (m, 2H), 6.93 (d, 1H), 6.31 (d, 1H), 3.74-3.63 (m, 11H).

<Example 73> Preparation of (4-(1-methyl-1H-pyrazol-4-yl)benzo[b]thiophene-2-yl)(morpholino)methanone

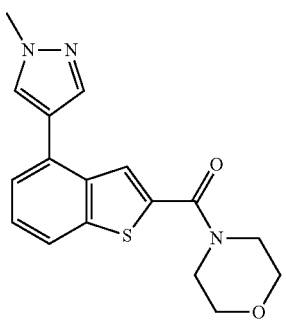 [SMILES: Cn1cc(-c2cccc3sc(C(=O)N4CCOCC4)cc23)cn1]

(4-bromobenzo[b]thiophene-2-yl)(morpholino)methanone (1 eq) was dissolved in dimethylene glycol ether (DME), to which $Pd(PPh_3)_4$ (tetrakis(triphenylphosphine) palladium (0), 0.02 eq), 1-methyl-1H-pyrazol-4-ylboronic acid (1.1 eq), and 2 M sodium carbonate (2M $Na_2CO_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 45%.

1H NMR (300 MHz, CDCl3) δ 7.93 (d, 1H), 7.61 (d, 1H), 7.49 (t, 1H), 7.36-7.35 (m, 2H), 6.39 (d, 1H), 3.78-3.73 (m, 11H).

<Example 74> Preparation of morpholino(4-(thiophene-2-yl)benzo[b]thiophene-2-yl)methanone

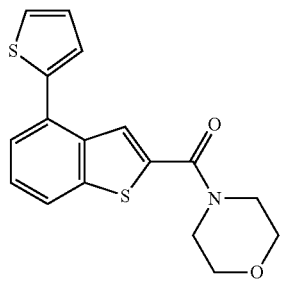 [SMILES: O=C(c1cc2c(-c3cccs3)cccc2s1)N1CCOCC1]

4-(thiophene-2-yl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 53%.

1H NMR (300 MHz, CDCl3) δ 7.88 (s, 1H), 7.82 (d, 1H), 7.49 (t, 1H), 7.42 (d, 2H), 7.31 (s, 1H), 7.17 (t, 1H), 3.76 (d, 8H).

<Example 75> Preparation of (4-(furan-3-yl)benzo[b]thiophene-2-yl)(morpholino)methanone

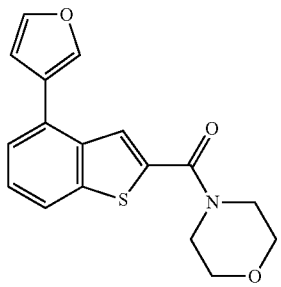 [SMILES: O=C(c1cc2c(-c3ccoc3)cccc2s1)N1CCOCC1]

4-(furan-3-yl)benzo[b]thiophene-2-carboxylic acid (1 eq) was dissolved in DMF, to which morpholine (1.01 eq), 1-ethyl-3-(3-dimethylaminopropyl)carbodiimide (EDC, 1.1 eq), 1-hydroxybenzotriazole (HOBT, 1.1 eq), and TEA (3 eq) were added stepwise, followed by stirring at room temperature for overnight. The reaction was terminated with a small amount of water, followed by extraction using water and EtOAc. The small amount of water remaining in the organic layer was dried over anhydrous MgSO$_4$. The solvent was eliminated by vacuum distillation, followed by vacuum drying. Then, a target compound was obtained by column separation with the yield of 71%.

1H NMR (300 MHz, CDCl3) δ 7.79 (d, 1H), 7.71 (d, 2H), 7.57 (s, 1H), 7.42 (d, 2H), 6.72 (s, 1H), 3.76 (d, 8H).

<Example 76> Preparation of morpholino(4-(thiophene-3-yl)benzo[b]thiophene-2-yl)methanone

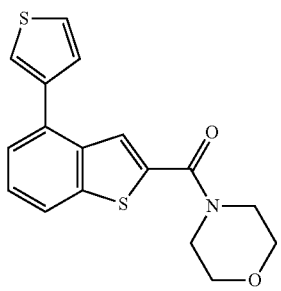 [SMILES: O=C(c1cc2c(-c3ccsc3)cccc2s1)N1CCOCC1]

(4-bromobenzo[b]thiophene-2-yl)(morpholino)methanone (1 eq) was dissolved in dimethylene glycol ether (DME), to which Pd(PPh$_3$)$_4$ (tetrakis(triphenylphosphine) palladium (0), 0.02 eq), thiophene-3-ylboronic acid (1.1 eq), and 2 M sodium carbonate (2M Na$_2$CO$_3$) solution (5 eq) were added, followed by stirring at 50° C. for overnight. The reaction mixture was cooled down at room temperature, which was then passed through celite for filtration. The filtrate was washed and extracted with water and EtOAc. The small amount of water remaining in the organic layer was dried over anhydrous MgSO4. The solvent was eliminated by vacuum distillation, followed by column separation. As a result, a target compound was obtained with the yield of 83%.

1H NMR (300 MHz, CDCl3) δ 7.88 (s, 1H), 7.82 (d, 1H), 7.49 (t, 1H), 7.42 (d, 2H), 7.31 (s, 1H), 7.17 (t, 1H), 3.76 (d, 8H).

<Comparative Example 1> Preparation of 5-((1H-indole-3-yl)methyl)-3-methyl-2-thioxothioxoimidazolidine-4-one (Nec-1)

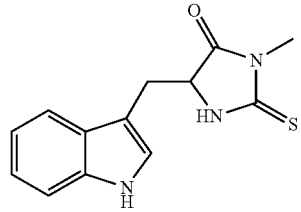 [SMILES: CN1C(=O)C(Cc2c[nH]c3ccccc23)NC1=S]

The compound of Comparative Example 1 used herein was purchased from KDR Biotech.

<Comparative Example 2> Preparation of 5-((7-chloro-1H-indole-3-yl)methyl)-3-methylimidazolidine-2,4-dione (Nec-1s)

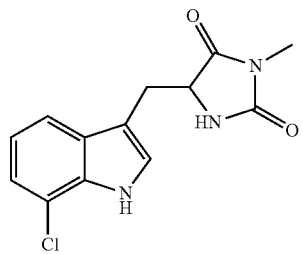 [SMILES: CN1C(=O)NC(Cc2c[nH]c3c(Cl)cccc23)C1=O]

The compound of Comparative Example 2 used herein was purchased from Biovision.

<Comparative Example 3> Preparation of doxycycline

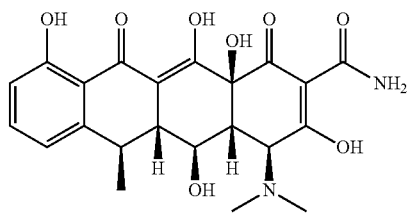 [SMILES: C[C@H]1c2cccc(O)c2C(=O)C2=C(O)[C@]3(O)C(=O)C(C(N)=O)=C(O)[C@@H](N(C)C)[C@@H]3[C@@H](O)[C@@H]21]

The compound of Comparative Example 3 used herein was purchased from Drug Store 24 h.

The chemical formulae of the compounds prepared in Examples 1~76 are shown in Table 1.
TABLE 1
| Example | Chemical Formula |
|---|---|
| 1 | 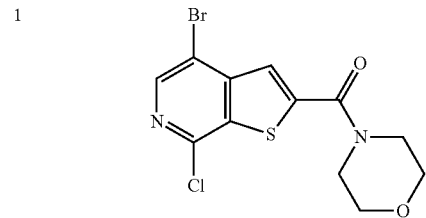 |
| 2 | 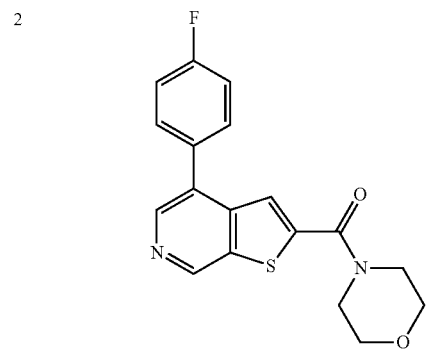 |
| 3 | 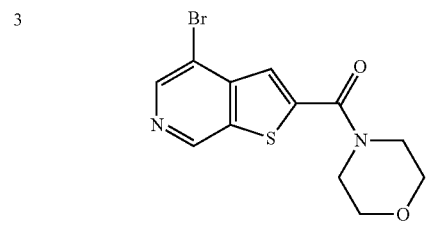 |
| 4 | 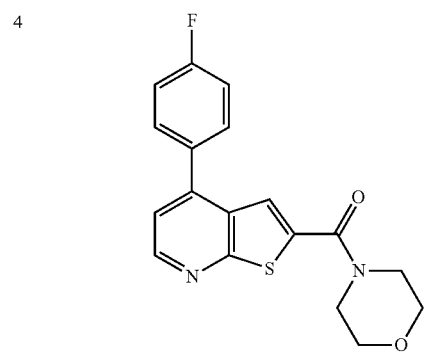 |
| 5 | 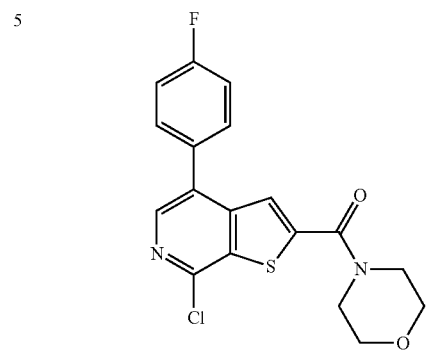 |
TABLE 1-continued
| Example | Chemical Formula |
|---|---|
| 6 |  |
| 7 |  |
| 8 |  |
| 9 |  |

TABLE 1-continued

| Example | Chemical Formula |
|---------|------------------|
| 10 | (4-acetamidophenyl)-substituted benzothiophene-2-carbonyl morpholine |
| 11 | 5-hydroxy-1H-indole-2-carbonyl morpholine |
| 12 | 5-chloro-1H-indole-2-carbonyl morpholine |
| 13 | 5-methyl-1H-benzimidazole-2-carbonyl morpholine |
| 14 | 5-bromo-1H-benzimidazole-2-carbonyl morpholine |
| 15 | benzofuran-2-carbonyl morpholine |
| 16 | 5-bromobenzofuran-2-carbonyl morpholine |

TABLE 1-continued

| Example | Chemical Formula |
|---------|------------------|
| 17 | 4,6-dimethylbenzothiophene-2-carbonyl morpholine |
| 18 | 6,7-dimethylbenzothiophene-2-carbonyl morpholine |
| 19 | 6-methoxybenzothiophene-2-carbonyl morpholine |
| 20 | 4-(N,N-diethylcarbamoyl)benzothiophene-2-carbonyl morpholine |
| 21 | 5-methyl-1H-indole-2-carbonyl morpholine |
| 22 | 5-methoxy-1H-indole-2-carbonyl morpholine |
| 23 | 1H-benzimidazole-2-carbonyl morpholine |
| 24 | 5-methoxy-1H-benzimidazole-2-carbonyl morpholine |

TABLE 1-continued

| Example | Chemical Formula |
|---|---|
| 25 | 1-methylindole-2-carbonyl-morpholine |
| 26 | 5-methoxybenzofuran-2-carbonyl-morpholine |
| 27 | 6-methylbenzofuran-2-carbonyl-morpholine |
| 28 | 5-amino-benzothiophene-2-carbonyl-morpholine |
| 29 | 7-bromo-benzothiophene-2-carbonyl-morpholine |
| 30 | 4-(2-fluorophenyl)-benzothiophene-2-carbonyl-morpholine |
| 31 | 4-(biphenyl-4-yl)-benzothiophene-2-carbonyl-morpholine |
| 32 | 4-(4-methylphenyl)-benzothiophene-2-carbonyl-morpholine |
| 33 | 4-(4-carboxyphenyl)-benzothiophene-2-carbonyl-morpholine |
| 34 | 4-(4-methoxyphenyl)-benzothiophene-2-carbonyl-morpholine |

TABLE 1-continued
| Example | Chemical Formula |
|---------|------------------|
| 35 | 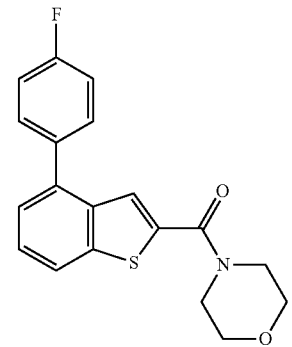 [SMILES: O=C(c1cc2c(-c3ccc(F)cc3)cccc2s1)N1CCOCC1] |
| 36 | |
| 37 | |
| 38 | |
| 39 | 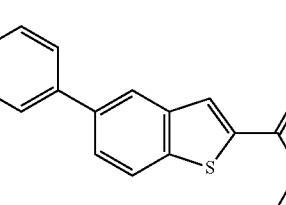 |
| 40 | |
| 41 | |
| 42 | |

TABLE 1-continued
| Example | Chemical Formula |
|---------|------------------|
| 43 | 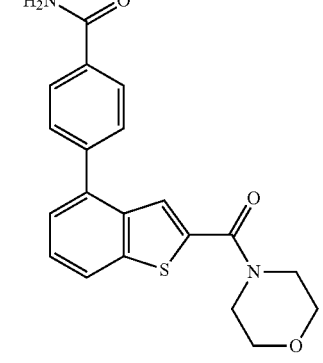 |
| 44 | |
| 45 | |
| 46 | |
TABLE 1-continued
| Example | Chemical Formula |
|---------|------------------|
| 47 | 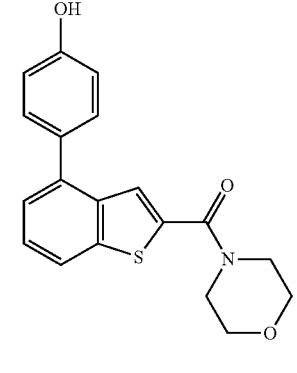 [SMILES: O=C(c1cc2c(-c3ccc(O)cc3)cccc2s1)N1CCOCC1] |
| 48 | |
| 49 | |
| 50 | |

TABLE 1-continued
| Example | Chemical Formula |
|---|---|
| 51 | 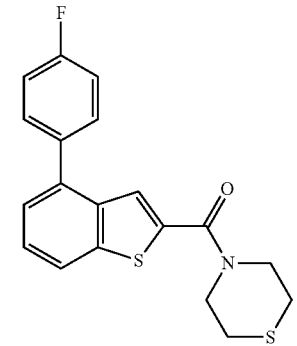 [SMILES: O=C(c1cc2c(-c3ccc(F)cc3)cccc2s1)N1CCSCC1] |
| 52 | 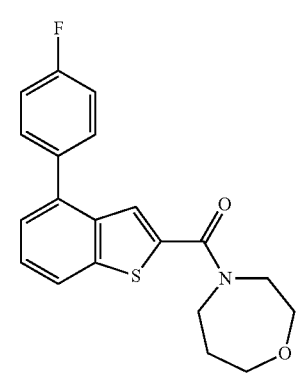 [SMILES: O=C(c1cc2c(-c3ccc(F)cc3)cccc2s1)N1CCCOCC1] |
| 53 | 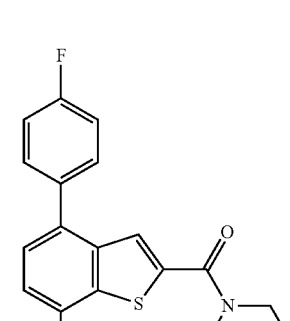 |
| 54 | 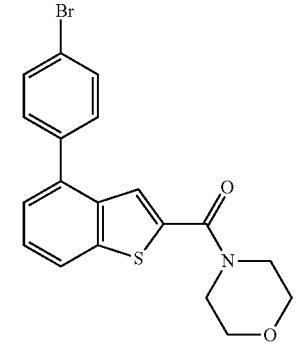 [SMILES: O=C(c1cc2c(-c3ccc(Br)cc3)cccc2s1)N1CCOCC1] |
| 55 | 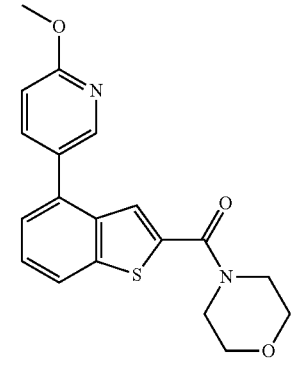 [SMILES: COc1ccc(-c2cccc3sc(C(=O)N4CCOCC4)cc23)cn1] |
| 56 | 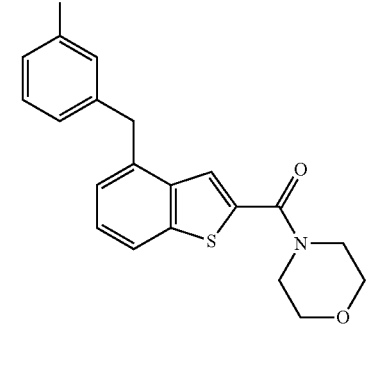 |
| 57 | 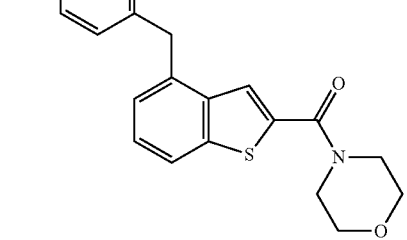 |
| 58 | 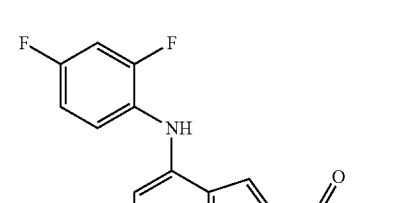 |

TABLE 1-continued

| Example | Chemical Formula |
|---|---|
| 59 | (4-fluorophenoxy-benzothiophene-morpholine carbonyl) |
| 60 | (4-fluorophenethyl-benzothiophene-morpholine carbonyl) |
| 61 | (4-fluorobenzyloxy-benzothiophene-morpholine carbonyl) |
| 62 | (4-fluorobenzylsulfonyl-benzothiophene-morpholine carbonyl) |
| 63 | (2,4-difluorophenyl-benzothiophene-morpholine carbonyl) |
| 64 | (4-methanesulfonylphenyl-benzothiophene-morpholine carbonyl) |
| 65 | (4-fluorophenyl-benzothiophene-morpholine carbonyl) |
| 66 | (6-fluoropyridin-3-yl-benzothiophene-morpholine carbonyl) HCl |

TABLE 1-continued

| Example | Chemical Formula |
|---------|------------------|
| 67 | 4-(4-fluorobenzyl)benzothiophene-2-yl morpholinyl ketone |
| 68 | 4-((4-fluorophenyl)amino)benzothiophene-2-yl morpholinyl ketone |
| 69 | 4-(N-methyl-N-(4-fluorophenyl)amino)benzothiophene-2-yl morpholinyl ketone |
| 70 | 4-((4-fluorophenyl)sulfonamido)benzothiophene-2-yl morpholinyl ketone |
| 71 | 4-((4-fluorobenzyl)thio)benzothiophene-2-yl morpholinyl ketone |
| 72 | 4-(1-methyl-5-cyanopyrrol-2-yl)benzothiophene-2-yl morpholinyl ketone |
| 73 | 4-(1-methylpyrazol-4-yl)benzothiophene-2-yl morpholinyl ketone |
| 74 | 4-(thiophen-2-yl)benzothiophene-2-yl morpholinyl ketone |

TABLE 1-continued

| Example | Chemical Formula |
|---|---|
| 75 | 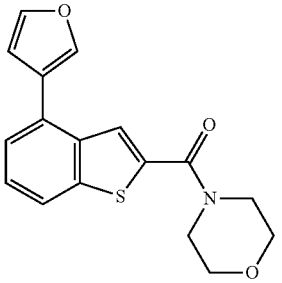 [SMILES: O=C(c1cc2c(-c3ccoc3)cccc2s1)N1CCOCC1] |
| 76 | 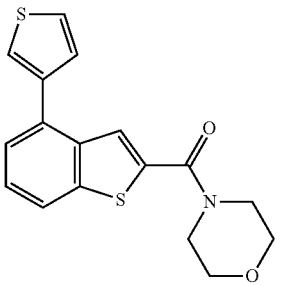 [SMILES: O=C(c1cc2c(-c3ccsc3)cccc2s1)N1CCOCC1] |

<Experimental Example 1> Evaluation of RIPK1 (Receptor-Interacting Serine/Threonine-Protein Kinase 1) Inhibitory Activity The following experiment was performed to evaluate RIPK1 (receptor-interacting serine/threonine-protein kinase 1) inhibitory activity of the compounds of examples of the invention.

RIPK1 enzyme immuno-precipitated in HEK293 (Human Embryonic Kidney 293) cell lysate was used as kinase. The experiment was performed according to the method described in Cell. 12; 137(6):1112-23(2009). RIPK1 protein was over-expressed in HEK293 cell line, to which lysis buffer (50 mM Tris-Cl [pH 8.0], 150 mM NaCl, 1 mM EDTA, 1% NP-40, 0.4 mM phenylmethylsulfonyl fluoride (PMSF)) was added for cell lysis. Centrifugation was performed at 13,000 rpm for 10 minutes to separate the supernatant. RIPK1 monoclonal antibody (610459, BD Bioscience) and A/G agarose beads (sc-2003, Santa Cruz Biotechnology) were added thereto, followed by immuno-precipitation in a 4° C. rotator for 12 hours.

The immune complex was washed with lysis buffer twice and then washed with kinase assay buffer (20 mM HEPES [pH7.6], 2 mM DTT, 1 mM NaF, 1 mM Na$_3$Vo$_4$, 20 mM β-glycerophosphate, 20 mM PNPP, 20 mM MgCl$_2$, 20 mM MnCl$_2$, 1 mM Benzamidie, and 1 mM EDTA) lastly. Kinase assay buffer and the compound were added to the RIPK1 immuno-precipitate, followed by reaction in a 24° C. constant-temperature water bath for 15 minutes. Additional reaction was induced for 30 minutes at 30° C. after 100 μM of ATP and 10 μCi[$^{32}$P] γ-ATP were added thereto. The reaction mixture was washed with kinase assay buffer once, to which protein loading buffer was added, followed by heating at 100° C. for 3 minutes. The reaction mixture was then loaded on 8% SDS-PAGE gel. Radioactive image of the phosphorylated RIPK1 was detected with FLA-7000 (GE healthcare). The image Quant TL program was used for the quantification. The results are shown in Table 2 below.

TABLE 2

| Example | RIPK1 activity (%) 100 μM |
|---|---|
| 1 | 52.5 ± 7.8 |
| 2 | 45.0 ± 12.7 |
| 3 | 52.0 ± 2.8 |
| 4 | 3.0 ± 1.4 |
| 5 | 85.1 ± 24.7 |
| 6 | 48.5 ± 23.3 |
| 7 | 87.1 ± 17.7 |
| 8 | 88.5 ± 16.3 |
| 9 | 76.0 ± 33.9 |
| 10 | 62.5 ± 16.8 |
| 11 | 70.7 ± 28.5 |
| 12 | 60.0 |
| 13 | 83.4 ± 16.1 |
| 14 | 62.0 ± 6.2 |
| 15 | 85.6 ± 26.7 |
| 16 | 88.0 ± 24.7 |
| 17 | 62.5 ± 16.8 |
| 18 | 76.5 ± 12.0 |
| 19 | 81.0 ± 26.9 |
| 20 | 77.0 ± 12.5 |
| 21 | 81.0 ± 17.0 |
| 22 | 43.5 ± 10.6 |
| 23 | 69.0 ± 24.5 |
| 24 | 52.0 ± 17.1 |
| 25 | 43.0 |
| 26 | 81.4 ± 29.3 |
| 27 | 86.0 ± 17.0 |
| 28 | 73.0 ± 38.2 |
| 29 | 82.5 ± 24.7 |
| 30 | 0.4 ± 0.1 |
| 31 | 85.2 ± 3.5 |
| 32 | 6.5 ± 4.9 |
| 33 | 90.0 ± 2.8 |
| 34 | 16.5 ± 7.8 |
| 35 | 3.5 ± 2.1 |
| 36 | 4.0 ± 2.8 |
| 37 | 25.5 ± 14.8 |
| 38 | 62.0 ± 12.0 |
| 39 | 3.7 ± 2.6 |
| 40 | 57.5 ± 12.0 |
| 41 | 84.7 ± 6.4 |
| 42 | 35.5 ± 3.9 |
| 43 | 58.5 ± 17.7 |
| 44 | 21.0 ± 17.0 |
| 45 | 86.7 ± 34.6 |
| 46 | 11.0 ± 5.7 |
| 47 | 20.0 ± 14.1 |
| 48 | 25.5 ± 0.7 |
| 49 | 27.0 ± 5.7 |
| 50 | 47.5 ± 2.1 |
| 51 | 2.5 ± 0.7 |
| 52 | 5.5 ± 4.9 |
| 53 | 70.0 ± 4.2 |
| 54 | 54.5 ± 37.5 |
| 55 | 43.0 ± 7.1 |
| 56 | 54.5 ± 37.5 |
| 57 | 20.0 ± 14.1 |
| 58 | 78.5 ± 30.4 |
| 59 | 21.0 ± 7.1 |
| 60 | 22.0 ± 15.6 |
| 61 | 22.5 ± 12.0 |
| 62 | 82.5 ± 5.0 |
| 63 | 1.5 ± 0.7 |
| 64 | 83.6 ± 12.7 |
| 65 | 67.0 ± 0.0 |
| 66 | 11.5 ± 4.9 |
| 67 | 49.5 ± 3.5 |
| 68 | 33.5 ± 12.0 |
| 69 | 22.5 ± 16.3 |
| 70 | 65.0 ± 32.5 |
| 71 | 87.0 ± 4.2 |
| 72 | 7.0 ± 8.5 |
| 73 | 22.0 ± 19.8 |
| 74 | 4.0 ± 0.0 |

TABLE 2-continued

| Example | RIPK1 activity (%) 100 μM |
|---|---|
| 75 | 3.5 ± 3.5 |
| 76 | 1.5 ± 0.7 |

As shown in Table 2, the compounds of examples of the present invention were confirmed to have RIPK1 inhibitory activity. Particularly, the compounds of examples 2, 4, 6, 22, 25, 30, 32, 34, 35, 36, 37, 39, 42, 44, 46, 47, 48, 49, 50, 51, 52, 55, 57, 59, 60, 61, 63, 66, 67, 68, 69, 72, 73, 74, 75, and 76 of the invention were confirmed to inhibit RIPK1 at least 50%. More particularly, those compounds of examples 4, 30, 32, 34, 35, 36, 39, 46, 47, 51, 52, 57, 63, 66, 72, 74, 75, and 76 inhibited RIPK1 by 80% or more, indicating that the compounds had a very excellent inhibitory activity.

The compound represented by formula 1 of the invention is excellent in inhibiting RIPK1 (receptor-interacting serine/threonine-protein kinase 1) causing retinal disease. Therefore, the pharmaceutical composition comprising the compound above as an active ingredient can be advantageously used as a pharmaceutical composition for the prevention or treatment of retinal disease.

<Experimental Example 2> Evaluation of Retinal Nerve Protection Effect Under Oxygen-Glucose Deprivation (OGD) Condition The following experiment was performed to evaluate the protective effect of the compounds of examples of the invention on the retinal nerve under oxygen-glucose deprivation condition.

The retinal ganglion cell line RGC-5 (rat ganglion cell) was cultured in DMEM (Dulbecco's modified Eagle's medium) supplemented with 10% FBS (fetal bovine serum) and 1% penicillin/streptomycin. The cells were distributed in a 96-well plate at the density of $8 \times 10^3$ cells/well, followed by culture in a 37° C., $CO_2$ incubator for 12 hours. The cells were washed with PBS once and the medium was replaced with glucose free DMEM. The cells were treated with either DMSO (0.1%) alone (control) or with the compounds of examples (20 μM) shown in Table 3, followed by culture in an anaerobic incubator (10% $H_2$, 5% $CO_2$, 85% $N_2$, 37° C., chamber (ThermoForma, USA)) for 15 hours to induce cell death.

The level of cell death was measured by LDH (lactate dehydrogenase, Roche) assay. The LDH assay is a method for measuring the activity of LDH released from the damaged cells into the culture medium. $NAD^+$ was reduced to NADH and $H^+$ by LDH, and the bond of tetrazolium salt INT ring was cleaved by diaphorase to form formazan. Absorbance of the formazan was measured at 490 nm by using Victor 3 (PerkinElmer). The absorbance reflects the amount of dead cells.

The level of the control LDH under oxygen-glucose deprivation condition was regarded as 100%, and the level of LDH in the cell group cultured in normal medium (10% FBS, DMEM) for the same time was regarded as 0%. Based on that, the levels of LDH of the cell groups treated with the compounds of the invention under oxygen-glucose deprivation condition were converted into the relative ratio of cell death. The compounds of examples of the invention were treated to wells, each compound for three wells, and then each experiment was performed in triplicate. The mean values are presented in Table 3.

TABLE 3

| Example | Death of retinal nerve cell (%) |
|---|---|
| 1 | 37.4 ± 1.3 |
| 2 | 47.4 ± 10.7 |
| 3 | 40.1 ± 18.6 |
| 4 | 57.8 ± 8.9 |
| 5 | 62.1 ± 3.7 |
| 6 | 30.7 ± 1.06 |
| 7 | 90.0 ± 3.3 |
| 8 | 52.3 ± 11.1 |
| 9 | 64.6 ± 9.5 |
| 10 | 49.0 ± 7.0 |
| 11 | 41.1 ± 3.1 |
| 12 | 35.7 ± 0.1 |
| 13 | 69.6 ± 2.0 |
| 14 | 82.1 ± 11.2 |
| 15 | 42.7 ± 2.0 |
| 16 | 19.3 ± 1.4 |
| 17 | 38.5 ± 5.5 |
| 18 | 37.0 ± 1.7 |
| 19 | 70.9 ± 9.7 |
| 20 | 43.6 ± 8.5 |
| 21 | 64.7 ± 7.1 |
| 22 | 78.6 ± 13.8 |
| 23 | 45.6 ± 3.6 |
| 24 | 76.4 ± 13.4 |
| 25 | 37.0 ± 1.2 |
| 26 | 48.6 ± 6.5 |
| 27 | 53.7 ± 9.1 |
| 28 | 60.0 ± 8.2 |
| 29 | 51.4 ± 10.9 |
| 30 | 51.0 ± 5.9 |
| 31 | 81.2 ± 8.3 |
| 32 | 64.6 ± 7.4 |
| 33 | 51.5 ± 7.0 |
| 34 | 55.4 ± 18.1 |
| 35 | 90.0 ± 3.3 |
| 36 | 58.0 ± 3.8 |
| 37 | 87.0 ± 13.2 |
| 38 | 59.9 ± 0.2 |
| 39 | 46.2 ± 0.8 |
| 40 | 68.2 ± 11.2 |
| 41 | 58.3 ± 6.5 |
| 42 | 57.2 ± 11.2 |
| 43 | 62.3 ± 1.7 |
| 44 | 81.1 ± 6.5 |
| 45 | 89.4 ± 14.0 |
| 46 | 55.4 ± 12.8 |
| 47 | 59.1 ± 1.6 |
| 48 | 47.7 ± 13.2 |
| 49 | 43.8 ± 13.7 |
| 50 | 57.2 ± 8.1 |
| 51 | 44.7 ± 6.3 |
| 52 | 52.8 ± 4.4 |
| 53 | 59.9 ± 9.7 |
| 54 | 74.3 ± 5.1 |
| 55 | 47.2 ± 12.4 |
| 56 | 81.0 ± 16.1 |
| 57 | 89.1 ± 16.9 |
| 58 | 89.4 ± 6.4 |
| 59 | 59.5 ± 14.7 |
| 60 | 89.8 ± 10.7 |
| 61 | 53.5 ± 14.5 |
| 62 | 59.3 ± 16.3 |
| 63 | 48.3 ± 13.7 |
| 64 | 63.0 ± 17.8 |
| 65 | 79.6 ± 5.5 |
| 66 | 45.2 ± 10.5 |
| 67 | 59.3 ± 14.9 |
| 68 | 58.3 ± 11.9 |
| 69 | 69.4 ± 10.9 |
| 70 | 48.7 ± 10.3 |
| 71 | 89.1 ± 14.9 |
| 72 | 58.5 ± 16.1 |
| 73 | 62.3 ± 10.1 |
| 74 | 51.4 ± 10.3 |
| 75 | 41.7 ± 7.0 |
| 76 | 43.6 ± 6.6 |

TABLE 3-continued

| Example | Death of retinal nerve cell (%) |
|---|---|
| Comparative Example 1 | 89.5 ± 10.5 |
| Comparative Example 2 | 73.5 ± 10.3 |

As shown in Table 3, the compounds of examples of the invention showed better retinal nerve protection effect under oxygen glucose deprivation condition at the concentration of 20 μM than the compounds of Comparative Examples 1 and 2. In particular, the compounds of examples 1, 2, 3, and 76 demonstrated as low death rate of the retinal nerve cells as less than 50%. That is, those compounds induced cell death less than the compounds of Comparative Examples 1 (89.5%) and 2 (73.5%). So, the compounds of the invention were confirmed to have excellent retinal nerve cell protection effect.

Therefore, it was confirmed that the compound represented by formula 1 of the present invention had excellent retinal nerve cell protection effect under oxygen-glucose deprivation condition, so that the pharmaceutical composition comprising the compound above as an active ingredient can be effectively used as a pharmaceutical composition for the prevention or treatment of retinal disease.

<Experimental Example 3> Evaluation of Retinal Neuron Protection Effect Under Necroptosis Inducing (TCZ; TNFα+Cycloheximide+zVAD) Condition The following experiment was performed to evaluate the retinal neuron protection effect of the compounds of the invention under necroptosis inducing condition.

The retinal ganglion cell line RGC-5 (rat ganglion cell-5) was cultured in DMEM (Dulbecco's modified Eagle's medium) supplemented with 10% FBS (fetal bovine serum) and 1% penicillin/streptomycin. The cells were distributed in a 96-well plate at the density of $8 \times 10^3$ cells/well, followed by culture in a 37° C., $CO_2$ incubator for 12 hours. The medium supplemented with TNFα (10 ng/ml), cycloheximide (10 μg/ml), and zVAD (10 μM) (TCZ) was treated with DMSO (0.1%) alone (control) or with the compounds of the invention (20 μM), followed by additional culture in a 37° C., $CO_2$ incubator for 15 hours to induce cell death.

The level of cell death was measured by LDH (lactate dehydrogenase, Roche) assay. The level of the control LDH under TCZ condition was regarded as 100%, and the level of LDH in the cell group cultured in normal medium (10% FBS, DMEM) for the same time was used for the measurement of the relative rate of cell death. The compounds of examples of the invention were treated to wells, each compound for three wells, and then each experiment was performed in triplicate. The mean values are presented in Table 4.

TABLE 4

| Example | Death of retinal nerve cell (%) |
|---|---|
| 1 | 79.3 ± 3.2 |
| 2 | — |
| 3 | 79.6 ± 3.2 |
| 4 | — |
| 5 | 57.6 ± 19.2 |
| 6 | 36.9 ± 8.4 |
| 7 | 63.2 ± 3.9 |
| 8 | — |
| 9 | — |
| 10 | — |
| 11 | 26.7 ± 1.0 |
| 12 | 50.5 ± 7.4 |
| 13 | 71.2 ± 7.0 |
| 14 | 81.1 ± 15.2 |
| 15 | 72.6 ± 6.8 |
| 16 | 59.4 ± 11.3 |
| 17 | 47.3 ± 10.7 |
| 18 | 74.6 ± 8.2 |
| 19 | 71.6 ± 9.1 |
| 20 | — |
| 21 | 89.9 ± 19.4 |
| 22 | 69.5 ± 7.4 |
| 23 | 69.2 ± 4.2 |
| 24 | 66.6 ± 9.9 |
| 25 | 64.8 ± 11.2 |
| 26 | 75.9 ± 15.1 |
| 27 | 86.1 ± 1.3 |
| 28 | 84.3 ± 1.7 |
| 29 | 78.4 ± 6.5 |
| 30 | — |
| 31 | — |
| 32 | — |
| 33 | — |
| 34 | — |
| 35 | 89.2 ± 8.2 |
| 36 | — |
| 37 | — |
| 38 | 72.4 ± 7.5 |
| 39 | 74.9 ± 9.1 |
| 40 | — |
| 41 | — |
| 42 | — |
| 43 | — |
| 44 | — |
| 45 | — |
| 46 | — |
| 47 | 89.1 ± 1.2 |
| 48 | — |
| 49 | — |
| 50 | — |
| 51 | — |
| 52 | 80.8 ± 2.8 |
| 53 | — |
| 54 | — |
| 55 | — |
| 56 | — |
| 57 | — |
| 58 | — |
| 59 | — |
| 60 | — |
| 61 | — |
| 62 | — |
| 63 | — |
| 64 | — |
| 65 | 77.8 ± 9.6 |
| 66 | — |
| 67 | — |
| 68 | — |
| 69 | — |
| 70 | — |
| 71 | — |
| 72 | — |
| 73 | — |
| 74 | — |

TABLE 4-continued

| Example | Death of retinal nerve cell (%) |
|---|---|
| 75 | — |
| 76 | — |

In Table 4, - indicates that the experiment was not performed.

As shown in Table 4, the compounds of examples of the invention displayed the retinal nerve cell protection effect at the concentration of 20 μM under necroptosis inducing (TCZ; TNFα+cycloheximide+zVAD) condition. In particular, the compounds of examples 6, 11, and 17 displayed as low death rate of the retinal nerve cells as less than 50%, suggesting that they had excellent retinal neuron protection effect.

Therefore, it was confirmed that the compound represented by formula 1 of the present invention had excellent retinal nerve cell protection effect under necroptosis inducing condition, so that the pharmaceutical composition comprising the compound above as an active ingredient can be effectively used as a pharmaceutical composition for the prevention or treatment of retinal disease.

<Experimental Example 4> Evaluation of $IC_{50}$ to RIPK1 (Receptor-Interacting Serine/Threonine-Protein Kinase 1)

RIPK1 enzyme immuno-precipitated in HEK293 (Human Embryonic Kidney 293) cell lysate was used as a kinase. The experiment was performed according to the method described in Cell. 12; 137(6):1112-23(2009).

RIPK1 protein was over-expressed in HEK293 cell line, to which lysis buffer (50 mM Tris-Cl [pH 8.0], 150 mM NaCl, 1 mM EDTA, 1% NP-40, 0.4 mM phenylmethylsulfonyl fluoride (PMSF)) was added for cell lysis. Centrifugation was performed at 13,000 rpm for 10 minutes to separate the supernatant. RIPK1 monoclonal antibody (610459, BD Bioscience) and A/G agarose beads (sc-2003, Santa Cruz Biotechnology) were added thereto, followed by immuno-precipitation in a 4° C. rotator for 12 hours.

The compounds of examples of the invention were diluted at the different concentrations of 10 μM~0.05 μM (10, 5, 1, 0.5, 0.1, 0.05 uM) and mixed with the immuno-precipitated RIPK1 enzyme, followed by reaction in a 24° C. constant-temperature water bath for 15 minutes. Additional reaction was induced for 30 minutes at 30° C. after 100 μM of ATP and 10 μCi[$^{32}$P] γ-ATP were added thereto. The reaction mixture was washed with buffer once, to which protein loading buffer was added, followed by heating at 100° C. for 3 minutes. The reaction mixture was then loaded on 8% SDS-PAGE gel. Radioactive image of the phosphorylated RIPK1 was detected with FLA-7000 (GE healthcare). The image Quant TL program was used for the quantification. Based on the results, $IC_{50}$ of the compound was calculated by using sigmaplot 10.0 program. The results are shown in Table 5.

TABLE 5

| Example | $IC_{50}$ (nM) |
|---|---|
| 1 | — |
| 2 | — |
| 3 | — |
| 4 | 1,125 |
| 5 | — |
| 6 | — |
| 7 | — |
| 8 | — |
| 9 | — |
| 10 | — |
| 11 | — |
| 12 | — |
| 13 | — |
| 14 | — |
| 15 | — |
| 16 | — |
| 17 | — |
| 18 | — |
| 19 | — |
| 20 | — |
| 21 | — |
| 22 | — |
| 23 | — |
| 24 | — |
| 25 | — |
| 26 | — |
| 27 | — |
| 28 | — |
| 29 | — |
| 30 | 102.5 |
| 31 | — |
| 32 | — |
| 33 | — |
| 34 | — |
| 35 | 360.2 |
| 36 | 17.7 |
| 37 | — |
| 38 | — |
| 39 | 193.1 |
| 40 | — |
| 41 | — |
| 42 | — |
| 43 | — |
| 44 | — |
| 45 | — |
| 46 | — |
| 47 | — |
| 48 | — |
| 49 | — |
| 50 | — |
| 51 | 216.9 |
| 52 | 8,174.4 |
| 53 | — |
| 54 | — |
| 55 | — |
| 56 | — |
| 57 | — |
| 58 | — |
| 59 | — |
| 60 | — |
| 61 | — |
| 62 | — |
| 63 | 230.1 |
| 64 | — |
| 65 | — |
| 66 | — |
| 67 | — |
| 68 | — |
| 69 | — |
| 70 | — |
| 71 | — |
| 72 | — |
| 73 | — |
| 74 | 65.6 |
| 75 | 73.4 |
| 76 | 61.2 |
| Comparative Example 1 | 95.5 |

In Table 5, - indicates that the experiment was not performed.

As shown in Table 5, the compounds of examples of the invention were confirmed to have low $IC_{50}$ concentration against RIPK1 (receptor-interacting serine/threonine-protein kinase 1). Particularly, the compounds of examples 36, 74, 75, and 76 demonstrated 50% inhibition of RIPK1 (receptor-interacting serine/threonine-protein kinase 1) at a lower concentration than the compound of Comparative Example 1.

Therefore, it was confirmed that the compound represented by formula 1 of the present invention had excellent activity to inhibit RIPK1 (receptor-interacting serine/threonine-protein kinase 1) causing retinal disease even at a low concentration, so that the pharmaceutical composition comprising the compound above as an active ingredient can be effectively used as a pharmaceutical composition for the prevention or treatment of retinal disease.

<Experimental Example 5> Evaluation of Retinal Cell Protection Effect by Instillation The following experiment was performed to evaluate the retinal cell protection effect of the compound represented by formula 1 of the invention.

First, eye drops of Example 39 and Comparative Examples 1 and 2 having the eye drop type composition (%) as shown in Table 6 below were prepared.

extracted, followed by H&E staining to investigate retinal cell protection effect (n=3, 6 eyes). FIG. 1 is a schematic diagram illustrating the construction of the dry macular degeneration rat model and the eye drop instillation of the compounds of the invention.

Figure 2:
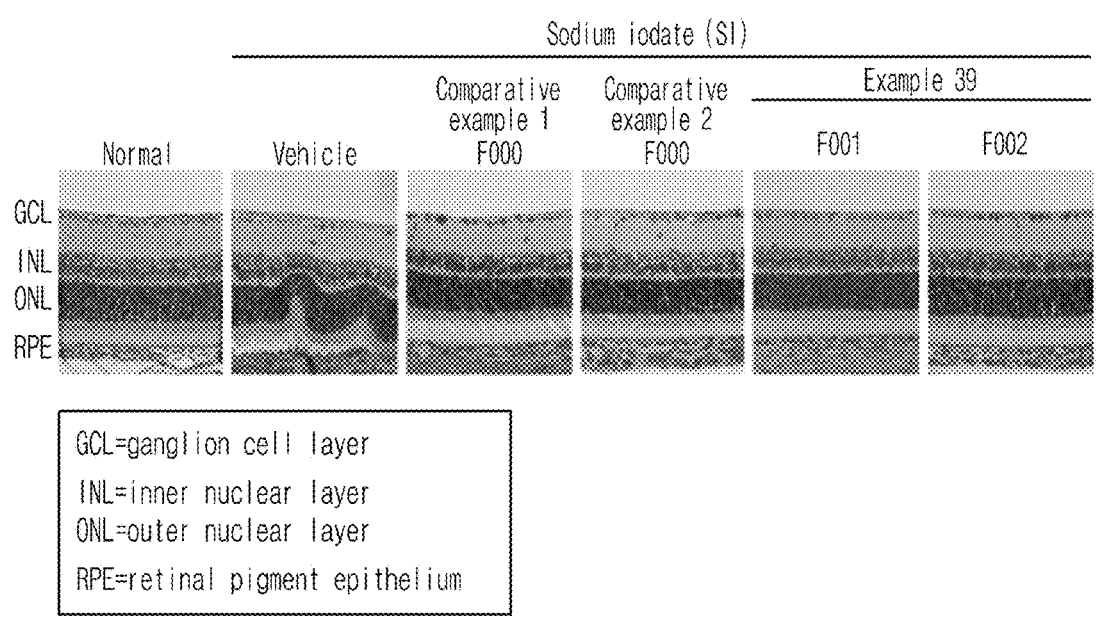
FIG. 2 is an image illustrating the protecting effect of the compounds of examples on retinal degeneration in the dry macular degeneration rat model.

The eyeballs were extracted from the dry macular degeneration rat model constructed by the same manner as described in FIG. 1, followed by histostaining. As a result, retina degeneration was not observed in those eyeballs eye drop instillated with the compounds of example 39 nor those of Comparative Examples 1 and 2. The results are shown in FIG. 2.

To measure the survival rate (%) of retinal pigment epithelial cells, the eyeballs extracted from the experimental rats were fixed in 4% glutaraldehyde solution for 4 hours and embedded in paraffin. Tissue sections were prepared in 5 μm thickness, followed by H&E (Hematoxylin and Eosin) staining. Photomicrographs were taken of 2-3 different areas within the RPE (retinal pigment epithelium) layer on 100× optical microscope (Leica), and the number of stained cells was counted. The number of RPE cells in the normal rat group was regarded as 100%, based on which the survival rate was calculated. The results are shown in FIG. 3.

Figure 3:
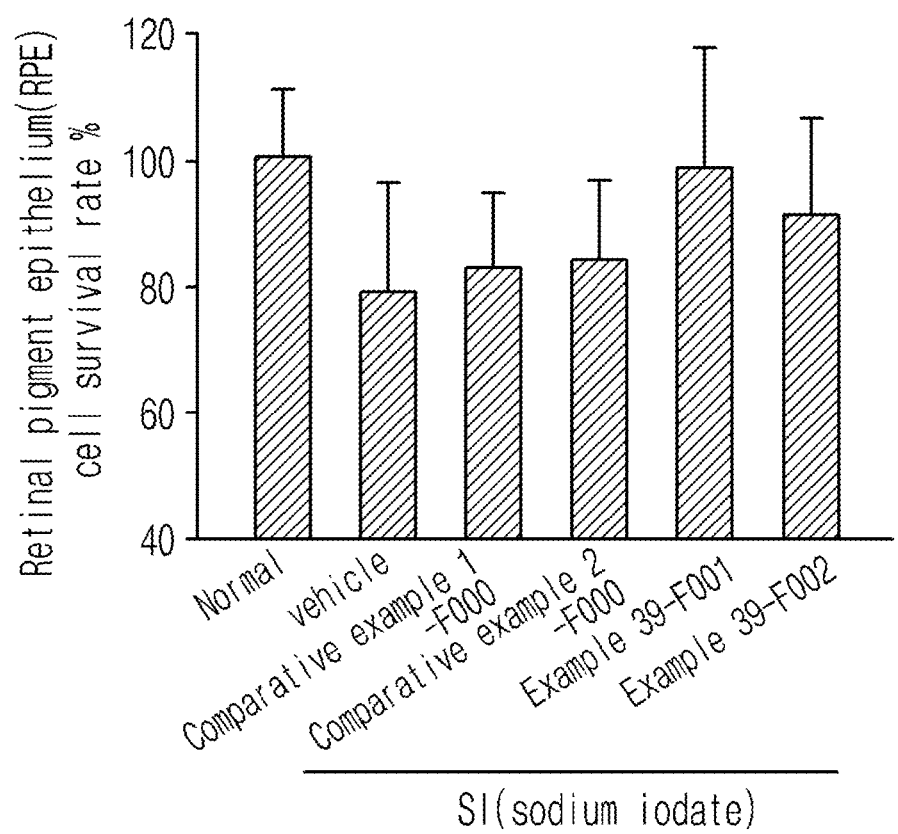
FIG. 3 is an image illustrating the protecting effect of the compounds of examples on retinal pigment epithelial cells in the dry macular degeneration rat model.

As shown in FIG. 3, the compounds of example 39 (F001 and F002) of the invention displayed better retinal pigment

TABLE 6

| Compound | Example 39 | | | | Comparative Example 1 | | Comparative Example 2 | |
|---|---|---|---|---|---|---|---|---|
| | F001 | F002 | F003 | F004 | F000 | F000 | F001 | F002 |
| Transcutol | — | 0.5 | — | 0.75 | — | — | — | 0.75 |
| Kolliphor TPGS | 4 | — | — | — | — | — | — | — |
| Cremophor EL | — | 2 | 4 | 3 | — | — | 4 | 3 |
| Labrafil M1944CS | — | 2 | — | 3 | — | — | — | 3 |
| Sodium chloride | 0.734 | 0.685 | 0.41 | — | — | — | 0.685 | 0.41 |
| Citric acid hydrate | 0.013 | | 0.0128 | | — | — | 0.0128 | |
| Sodium citrate hydrate | 0.45 | | 0.45 | | — | — | 0.45 | |
| PEG400 (polyethylene glycol 400) | 0.053 | | — | 30 | 15 | — | | |
| propyleneglycol | — | | 0.053 | — | — | | 0.053 | |
| Povidone K90 | 1.14 | | 1.5 | — | — | | 1.5 | |
| HCl | proper amount | | proper amount | — | — | | proper amount | |
| NaOH | proper amount | | proper amount | — | — | | proper amount | |
| DMSO | — | | — | 10 | — | | — | |
| Glycerine | — | | — | — | 12.5 | | — | |
| EDTA | — | | — | — | 0.05 | | — | |
| Boric acid | — | | — | — | 0.164 | | — | |
| Borax | — | | — | — | 0.1176 | | — | |
| Content (μg/ml) | 335.3 | 480.1 | 313.2 | 749.6 | 1000 | 1000 | 334.3 | 760.6 |

In Table 6, - indicates no addition.

From 3 days before the administration of sodium iodate (SI) to the 8-week-old dry macular degeneration rat model, the compound of the invention was instillated twice a day (50 μl/each eye drop instillation) and SI (ip, 50 mg/kg) was administered once. Additionally, the compound was instillated twice a day for 7 days. 7 days later, the eyeballs were epithelial cell protection effect than the compounds of Comparative Examples 1 and 2.

Therefore, it was confirmed that the compound represented by formula 1 of the present invention did not cause retinal degeneration but had excellent retinal pigment epithelial cell protection effect, so that the pharmaceutical composition comprising the compound above as an active ingredient can be effectively used as a pharmaceutical composition for the prevention or treatment of retinal disease.

<Experimental Example 6> Evaluation of Protective Effect on Retinal Layer Thickness Reduction by Instillation 1

The following experiment was performed to evaluate the retinal layer thickness protection effect of the compounds of the invention.

To measure the number (%) of ONL (outer nuclear layer) cells, the tissue sections of the eyeballs extracted from the rat used in Experimental Example 5 were stained with H&E solution. The number of stained cells in the outer nuclear layer was counted by photographing with optical microscope. 10 different areas were selected to count the cells for each retina. The cell number of the normal group was regarded as 100%. The results are shown in FIG. 4(A).

Figure 4A:
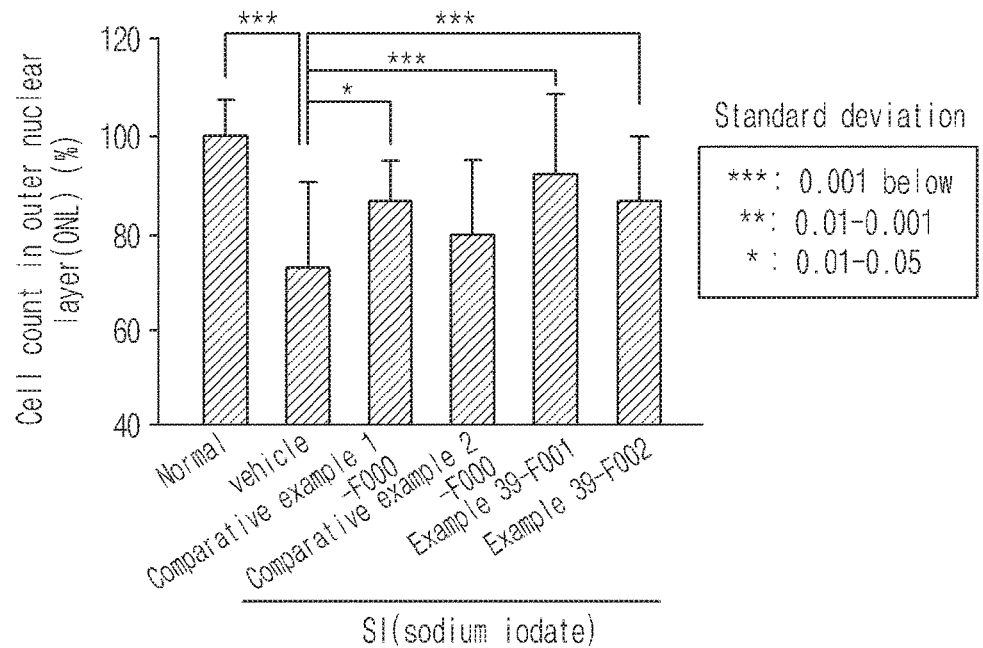
FIG. 4(A) is a graph illustrating the results of counting the number of cells in the outer nuclear layer after the eye drop instillation of the compounds of examples of the invention to the dry macular degeneration rat model.

As shown in FIG. 4(A), the compounds of example 39 (F001 and F002) of the invention displayed better ONL cell protection effect than the compounds of Comparative Examples 1 and 2.

To measure the thickness (μm) of ONL (outer nuclear layer), the tissue sections of the eyeballs extracted from the rat used in Experimental Example 5 were stained with H&E solution. Photographs were taken by optical microscope and the thickness of ONL was measured by using "image J" program. Ten different regions were analyzed for each retina. The thickness (μm) of ONL of the normal group was regarded as 100%. The results are shown in FIG. 4(B).

Figure 4B:
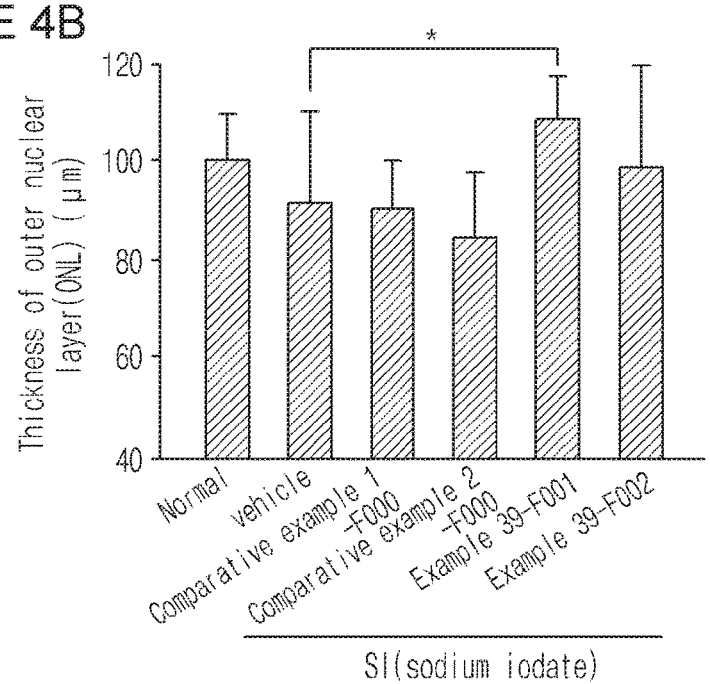
FIG. 4(B) is a graph illustrating the results of measuring the outer nuclear thickness (μm) after the instillation of the compounds of examples of the invention to the dry macular degeneration rat model.

As shown in FIG. 4(B), the compounds of example 39 (F001 and F002) of the invention displayed better ONL thickness protection effect than the compounds of Comparative Examples 1 and 2.

Therefore, it was confirmed that the compound represented by formula 1 of the present invention not only had the outer nuclear layer cell protection effect but also had outer nuclear layer thickness protection effect, so that the pharmaceutical composition comprising the same as an active ingredient can be effectively used as a pharmaceutical composition for the treatment of retinal disease.

<Experimental Example 7> Evaluation of Retinal Detachment Inhibitory Effect by MRI (Magnetic Resonance Imaging)

The following experiment was performed to evaluate the retinal detachment inhibitory effect of the compounds of the invention.

Figure 5:
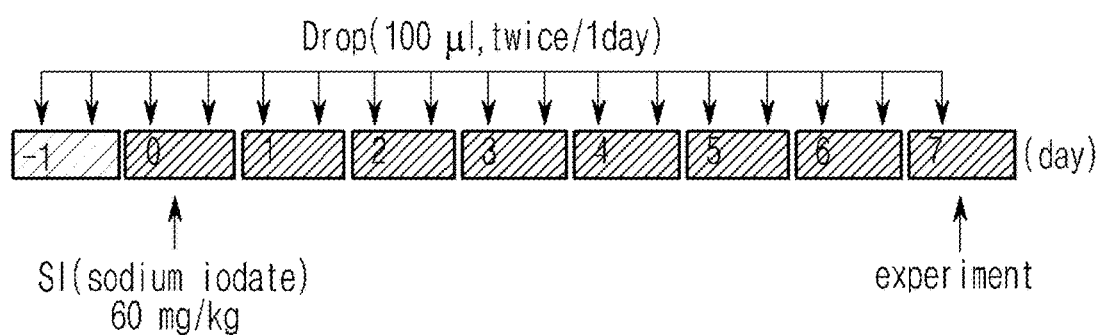
FIG. 5 is a schematic diagram illustrating the construction of the dry macular degeneration rabbit model and eye drop instillation of the compounds of examples of the invention.

First, 1 ml of 60 mg/ml sodium iodate (SI) was intravenously injected into a brown rabbit (Chinchilla, male, 3 kg) to induce degeneration of retinal pigment epithelium and photoreceptor cells, resulting in the construction of a dry macular degeneration rabbit model. Retinal degeneration was observed (*Eye* 2005.19, 464-468) one week after the SI administration, and a schematic diagram illustrating the eye drop instillation of the compounds is shown in FIG. 5.

Figure 6:
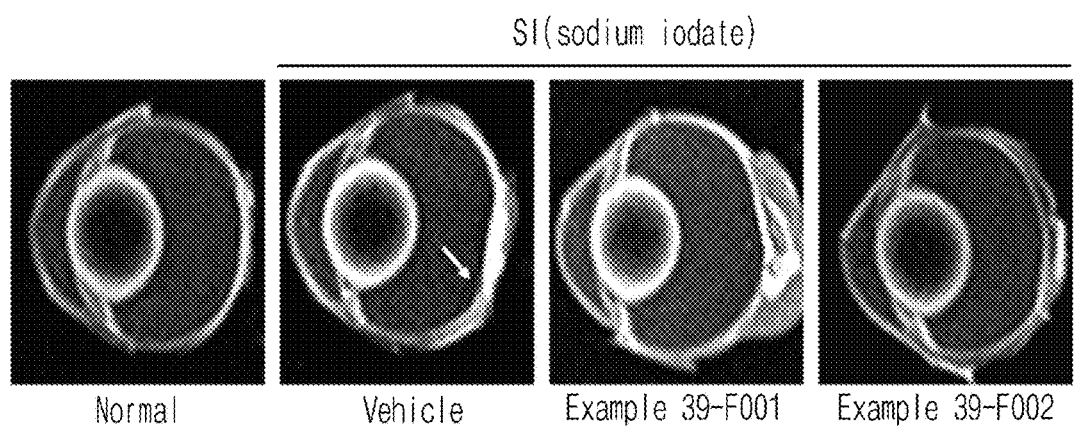
FIG. 6 is an image illustrating the results of MRI of the dry macular degeneration rabbit model after the instillation of the compounds of examples of the invention.

The dry macular degeneration rabbit model was instillated with the compound of the invention for 7 days (100 μl, twice a day). On day 7, the eyeballs were photographed by MRI for small animals. As a result, as shown in FIG. 6, retinal detachment was observed in the non-treated group, but the groups treated with the compounds of example 39 (F001 and F002) showed normal retinal structure.

Therefore, it was confirmed that the compound represented by formula 1 of the present invention had excellent retinal detachment inhibitory effect, so that the pharmaceutical composition comprising the same as an active ingredient can be effectively used as a pharmaceutical composition for the treatment of retinal disease.

<Experimental Example 8> Evaluation of Retinal Degeneration Inhibitory Effect by Histostaining (H&E Staining)

The following experiment was performed to evaluate the retinal degeneration inhibitory effect of the compounds of the invention.

The eyeballs obtained from the dry macular degeneration rabbit model of Experimental Example 7 were fixed in 4% paraformaldehyde. The cornea and lens were eliminated, followed by dehydration with alcohol and then paraffin blocks were prepared. The tissue blocks were sectioned by using a microtome to prepare tissue slides. The tissue slides were stained with hematoxylin-eosin (H&E staining), followed by observation under optical microscope. The results are shown in FIG. 7.

Figure 7:
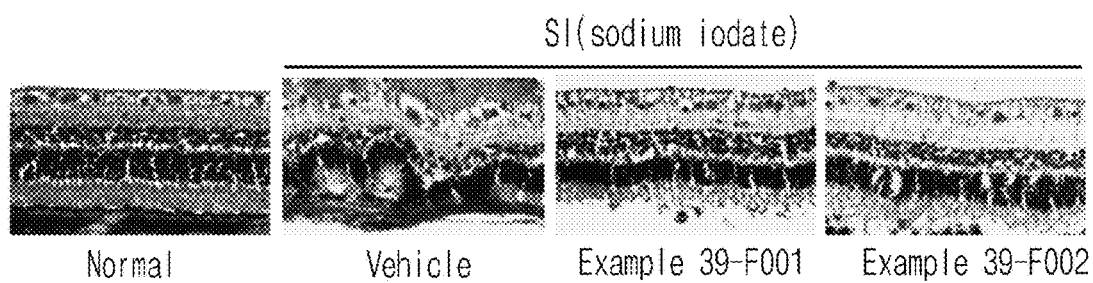
FIG. 7 is an image illustrating the results of observation of the retina of the dry macular degeneration rabbit model after H&E staining.

As shown in FIG. 7, the retinal structure was changed and degenerated in the non-treated group. However, the retinal structure remained normal in the group treated with the compounds of example 39 (F001 and F002).

Therefore, it was confirmed that the compound represented by formula 1 of the present invention had excellent retinal degeneration inhibitory effect, so that the pharmaceutical composition comprising the same as an active ingredient can be effectively used as a pharmaceutical composition for the treatment of retinal disease.

<Experimental Example 9> Evaluation of Protective Effect on Retinal Layer Thickness Reduction by Instillation 2

The following experiment was performed to evaluate the retinal layer thickness protection effect of the compounds of the invention.

Figure 8:
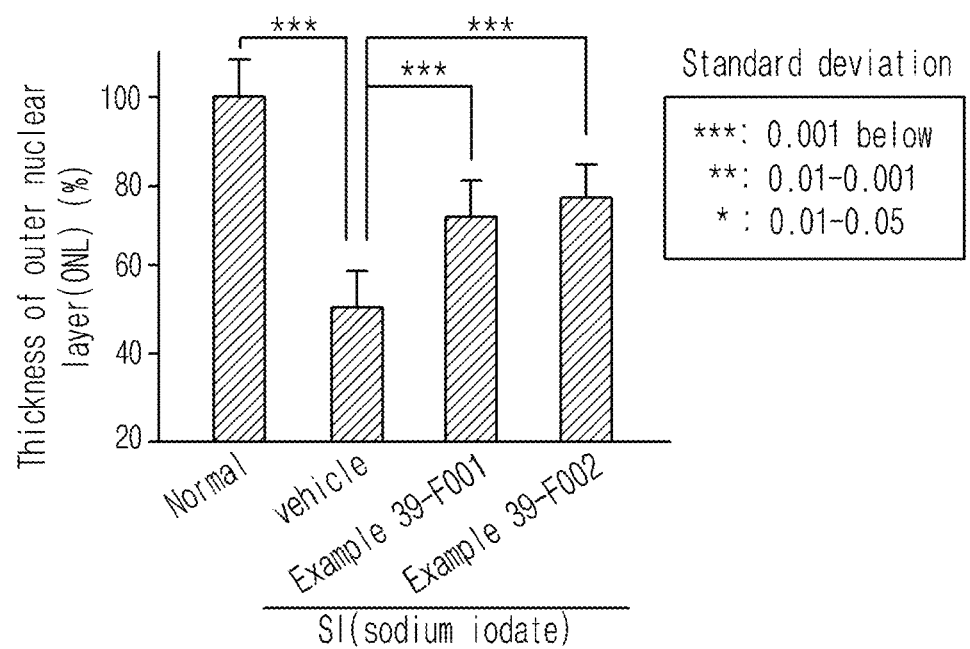
FIG. 8 is an image illustrating the results of measuring the outer nuclear layer thickness of the dry macular degeneration rabbit model.

The eyeballs were extracted from the dry macular degeneration rabbit model used in Experimental Example 7, and the thickness of ONL was measured. As a result, the compounds of example 39 of the invention displayed 70-80% retinal layer thickness protection effect and the results are shown in FIG. 8.

Therefore, it was confirmed that the compound represented by formula 1 of the present invention had excellent retinal layer thickness protection effect, so that the pharmaceutical composition comprising the same as an active ingredient can be effectively used as a pharmaceutical composition for the treatment of retinal disease.

<Experimental Example 10> Evaluation of Drug Efficacy by ERG (Electroretinography) 1

The following experiment was performed to evaluate the drug efficacy of the compound of the invention by ERG (Electroretinography).

Figure 9:
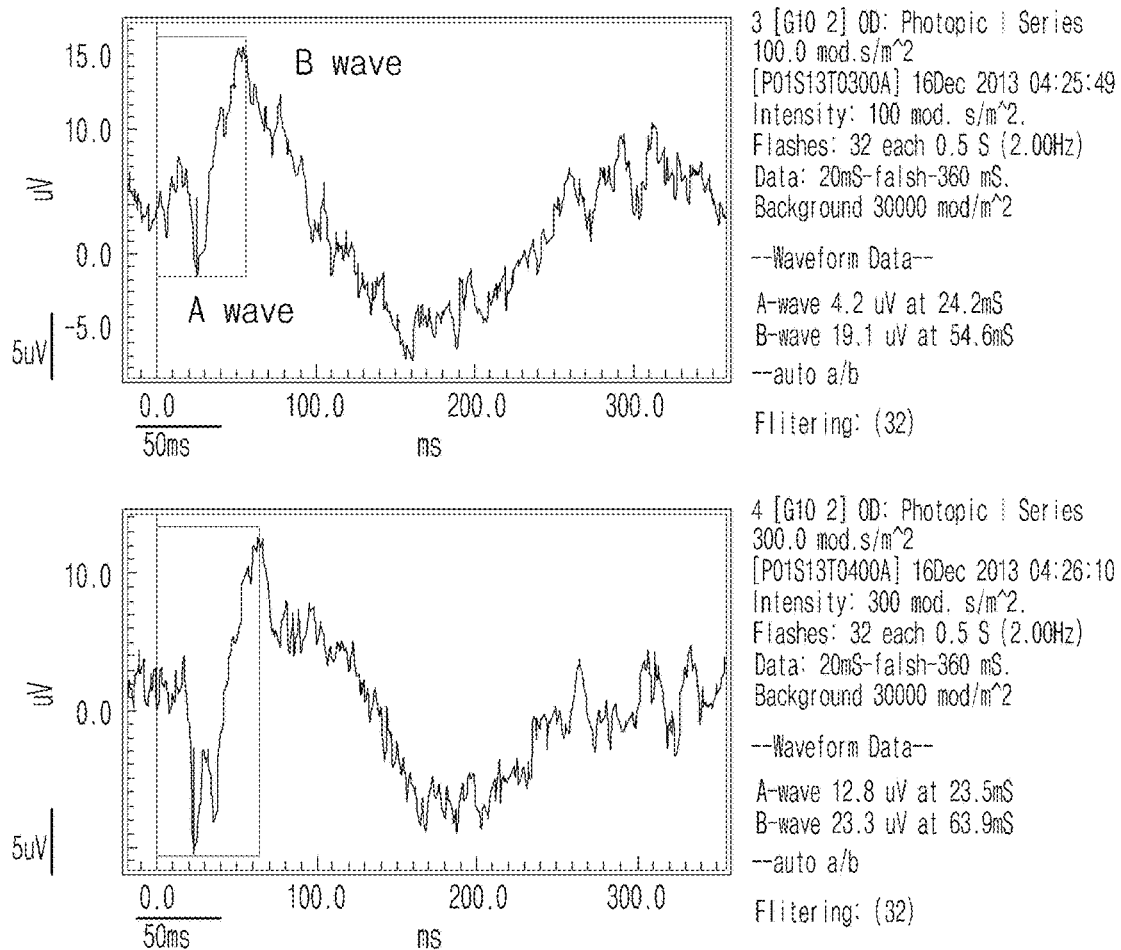
FIG. 9 is an image illustrating the results of measuring the potential difference of the retina of the dry macular degeneration rabbit model by ERG (Electroretinography)

The normal rabbit was anesthetized, which was adapted for 20 minutes in a dark room. Retinal potential difference was measured by ERG equipment. Electroretinography is a method to observe the response of photoreceptor cells with two light intensities. Particularly, A and B waves were measured from 100 to 10000 mcd, and the retinal potential difference measured at 3000 mcd. The schematic diagram is shown in FIG. 9. Drug efficacy was evaluated by observing the photoreceptor cells, for which the stronger response to wave A was selected.

Evaluation of candidate substances for dry macular degeneration was performed using a retinal degeneration rabbit model. The compounds of Comparative Examples 2 and 3 were used as comparative compounds. The compounds of example 39 of the invention and Comparative Example 2 were formulated as eye drops as shown in Table 2, which were instillated twice a day (100 μl/eye drop instillation). The compound of Comparative Example 3 was orally administered once a day (10 mg/rabbit, dissolved in saline). One week later, ERG was performed and the results are shown in Table 7, FIG. 10, and FIG. 11.

TABLE 7

| Example | Wave ratio | Drug efficacy (%) |
|---|---|---|
| Normal | 1.00 | 100 |
| Veh. | 0.52 | 0 |
| Examples39-F003 | 0.82 | 62 |
| Examples39-F004 | 0.91 | 81 |
| Comparative Example2-F001 | 0.91 | 81 |
| Comparative Example2-F002 | 0.83 | 64 |
| Comparative Example3-MH | 0.74 | 46 |
| Comparative Example3-HC | 0.67 | 31 |

In Table 7,

MH indicates monohydrate which was used for oral administration because it was not dissolved in water; and HC indicates hyclate which was used as injection/oral-preparation since it was well dissolved in water.

Figure 10:
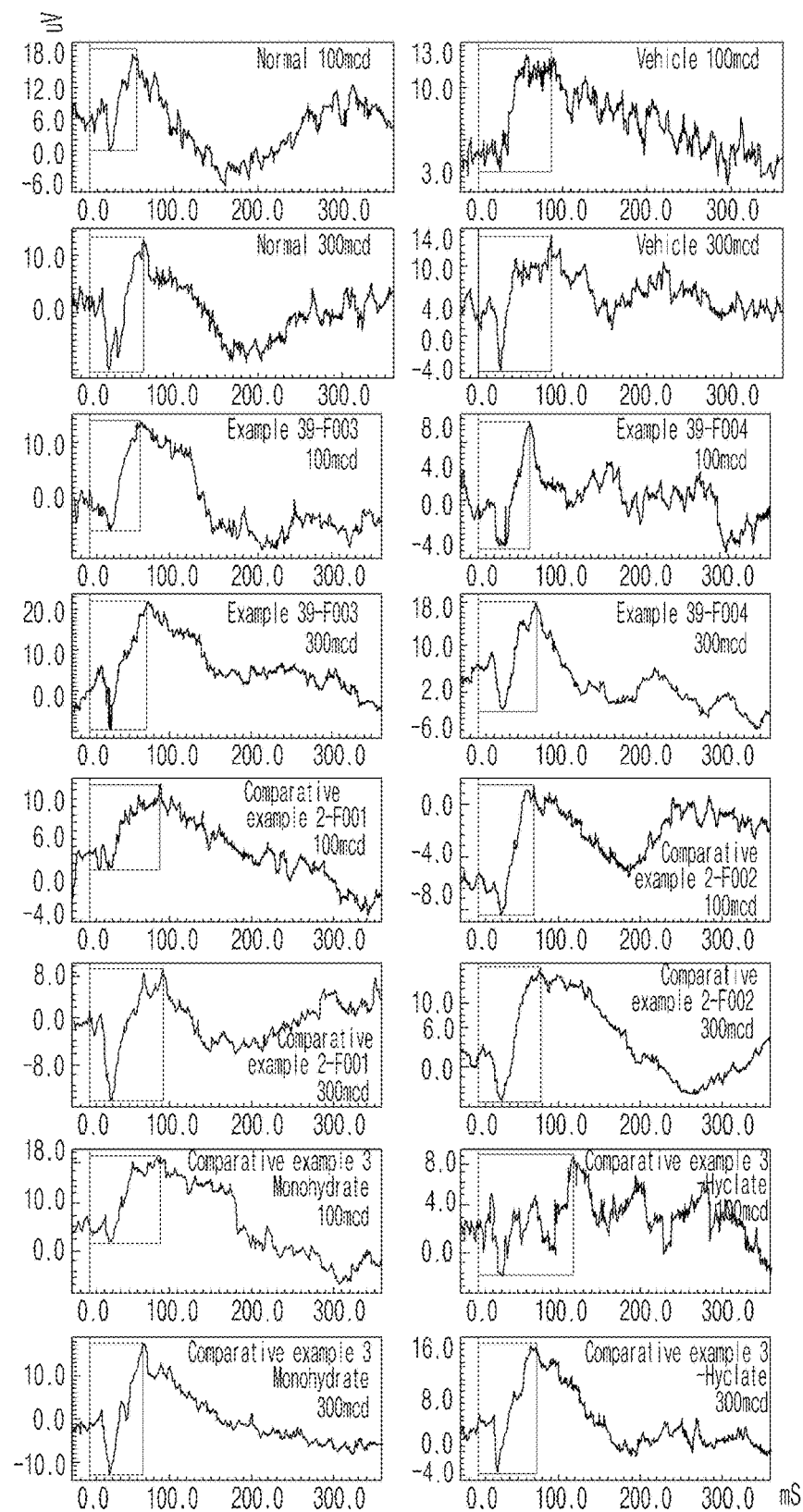
FIG. 10 is an image illustrating the protective effect of the compounds of examples on the retinal photoreceptor cell degeneration in the dry macular degeneration rabbit model which was investigated by ERG.

As shown in Table 7 and FIG. 10, when ERG was performed with the SI (sodium iodate) induced retinal degeneration model, wave A was significantly reduced in the retinal degeneration model. It was reduced to 50% at 300 mcd, compared to normal. In particular, the drug efficacy of the compound of example 39-F004 (81%) was significantly higher than the compound of Comparative Example 3-HC (doxycycline, 31%) orally administered, suggesting that the compound of example 39 had better retinal protection effect.

As shown in FIG. 11, the compounds of example 39-F003 and example 39-F004 were confirmed to exhibit 81.9% and 91.2% response compared to normal (100%), respectively. In the meantime, the compounds of Comparative Example 2-F001, Comparative Example 2-F002, Comparative Example 3-MH, and Comparative Example 3-HC were confirmed to exhibit 90.9%, 82.9%, 74.1%, and 66.9% response compared to normal (100%), respectively. More precisely, the compounds of example 39-F003 (81.9%) and example 39-F004 (91.2%) displayed significantly higher response strength than the compounds of Comparative Example 3-MH (74.1%) and Comparative Example 3-HC (66.9%).

Therefore, it was confirmed that the compound represented by formula 1 of the present invention had excellent cell protection effect, so that the pharmaceutical composition comprising the same as an active ingredient can be effectively used as a pharmaceutical composition for the treatment of retinal disease.

<Experimental Example 11> Evaluation of Drug Efficacy by Fundoscopy

To evaluate the drug efficacy of the compounds of the invention, the following experiment was performed using retinal fundus photographs.

First, to construct a dry macular degeneration pig model, 10 mg/kg of iodoacetic acid (IAA) was dissolved in PBS (phosphate buffered saline) and injected intravenously to a mini pig (Yutacan Micropig). One week after the IAA administration, retinal degeneration was confirmed by retinal fundus photography and fluorescence (*Experimental eye research* 2012. 97, 137-147), and a schematic diagram illustrating the eye drop instillation of the compounds is shown in FIG. 12.

Figure 12:
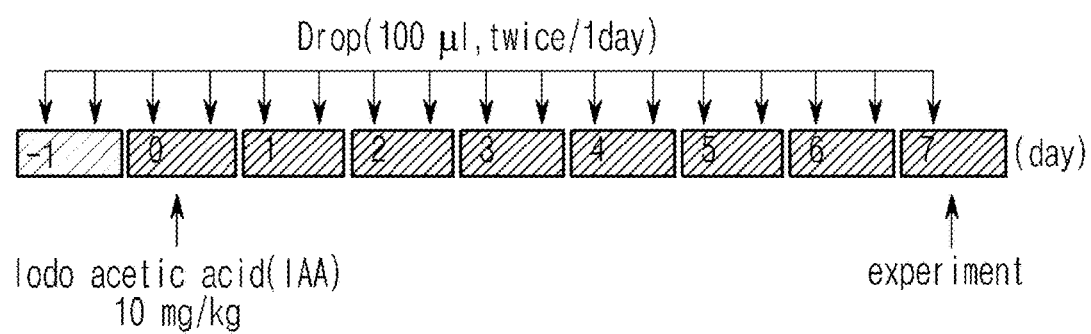
FIG. 12 is a schematic diagram illustrating the construction of the dry macular degeneration pig model and eye drop instillation of the compounds of examples of the invention.
Figure 13:
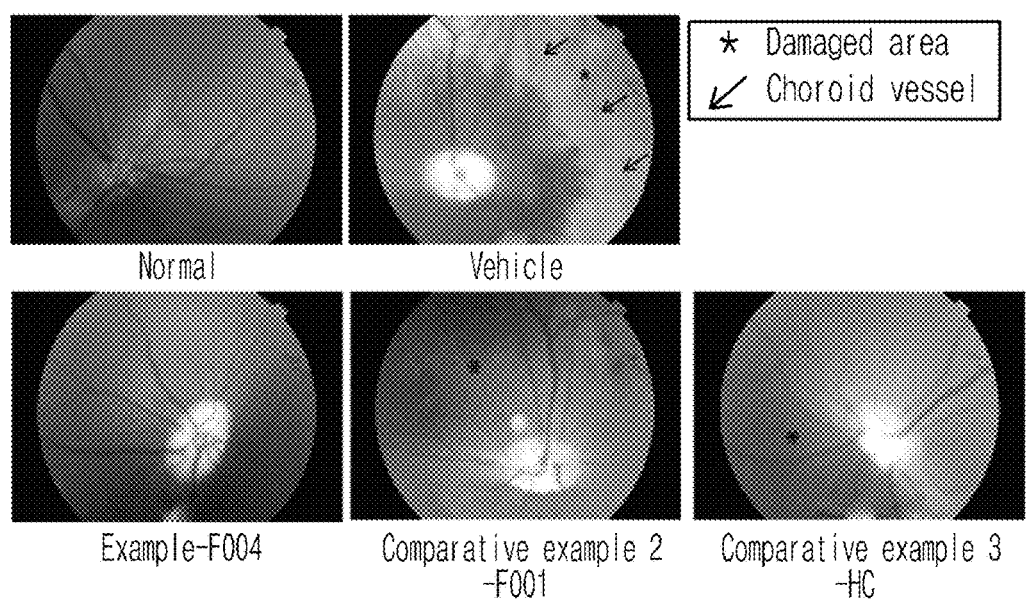
FIG. 13 is a photograph of the fundus taken by Fundoscopy 7 days after instillation of the compounds of examples of the invention to the dry macular degeneration pig model (*: damaged area; ✓: choroidal vessels)

The eye drop instillation of the compounds of the invention was performed from a day before the IAA administration as shown in FIG. 12. 7 days after the induction of retinal degeneration in the pig, retinal fundus photographs were taken and the results are shown in FIG. 13.

As shown in FIG. 13, in the non-treated group (Veh), retinal pigment epithelium was degenerated, so that choroidal vessels and bright areas were observed. In the groups treated with the compounds of Comparative Examples (2-F001 (eye drop instillation) and 3-HC (oral-administration)), damaged areas (*) were observed. However, in the group treated with the compound of example 39 (39-F004, eye drop instillation) of the invention, normal retina was observed.

Therefore, it was confirmed that the compound represented by formula 1 of the present invention had excellent retinal detachment inhibitory effect, so that the pharmaceutical composition comprising the same as an active ingredient can be effectively used as a pharmaceutical composition for the treatment of retinal disease.

<Experimental Example 12> Evaluation of Drug Efficacy by ERG (Electroretinography) 2

The following experiment was performed to evaluate the drug efficacy of the compound of the invention by ERG (Electroretinography).

The experiment was performed by the same manner as described in Experimental Example 10 except that a dry macular degeneration pig model was used instead of the dry macular degeneration rabbit model. The results are shown in Table 8, FIG. 14, and FIG. 15.

TABLE 8

| Example | Wave ratio | Drug efficacy (%) |
|---|---|---|
| Normal | 1.00 | 100 |
| Veh. | 0.25 | 0 |
| Example39-F004 | 0.53 | 37 |
| Comparative Example2-F001 | 0.32 | 10 |
| Comparative Example3-HC | 0.38 | 18 |

In Table 8, the composition of the compound of Comparative Example 3-HC was saline (0.9%).

Figure 14:
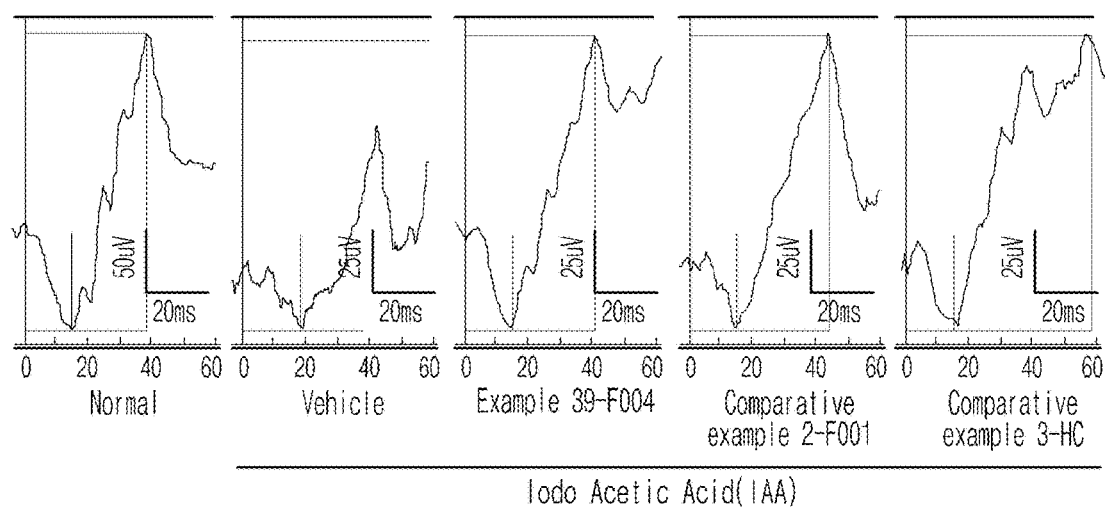
FIG. 14 is an image illustrating the protective effect of the compounds of examples on the retinal photoreceptor cell degeneration in the dry macular degeneration pig model which was investigated by ERG.
Figure 15:
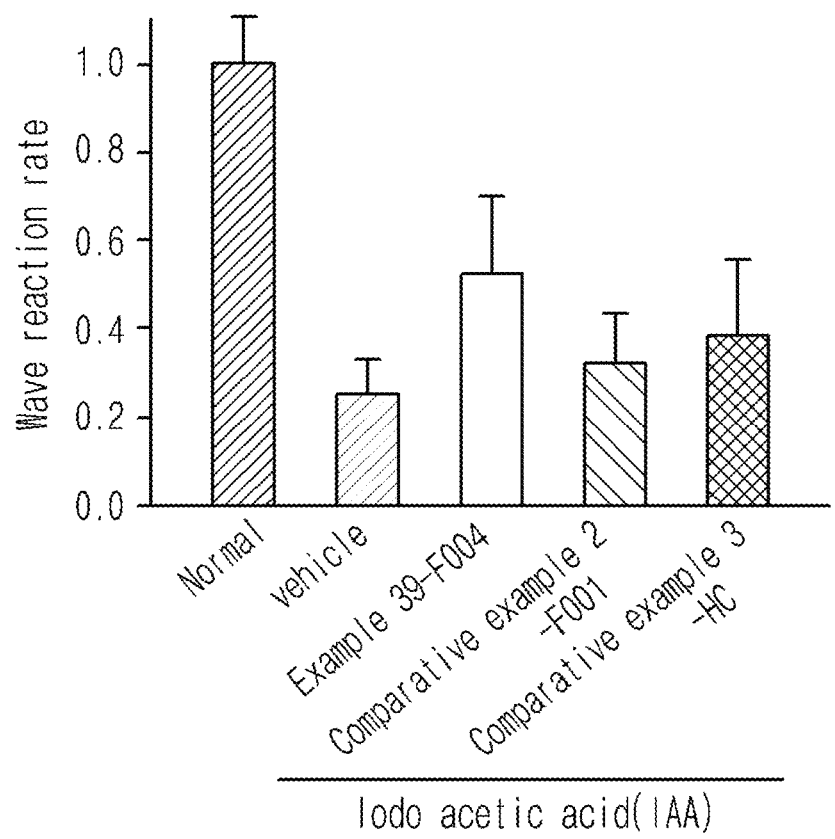
FIG. 15 is a graph illustrating the protective effect of the compounds of examples on the retinal photoreceptor cell degeneration in the dry macular degeneration pig model which was investigated by ERG.

As shown in Table 8, FIG. 14, and FIG. 15, wave A response was observed in the normal group, but wave A response was reduced in the groups treated with the compounds of Comparative Examples (2-F001 and 3-HC). In the meantime, all A waves were preserved in the example 39-F004 treated group. It means that the compound of example 39 (F004) had better retinal protection effect than the compounds of Comparative Examples (2-F001 and 3-HC).

Therefore, it was confirmed that the compound represented by formula 1 of the present invention had excellent cell protection effect, so that the pharmaceutical composition comprising the same as an active ingredient can be effectively used as a pharmaceutical composition for the treatment of retinal disease.

<Manufacturing Example 1> Preparation of Eye Drops

| | |
|---|---|
| Derivative represented by formula 1 | 0.1 g |
| Aminoethylsulfonic acid | 0.2 g |
| Benzalkonium chloride | 0.005 g |
| Tyloxapol | 0.02 g |
| Povidone (K3O) | 2.0 g |
| Sodium acetate | 0.02 g |
| Conc. glycerin | 2.2 g |
| Sodium hydroxide | proper amount |
| Purified water | proper amount |
| Total | 100 ml |

Eye drops were prepared by mixing all the above components by the conventional method for preparing eye drops.

<Manufacturing Example 2> Preparation of Health Food

| | |
|---|---|
| Derivative represented by formula 1 | 500 ng |
| Vitamin complex | proper amount |
| Vitamin A acetate | 70 mg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinic acid amide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

<Manufacturing Example 3> Preparation of Health Beverage

| | |
|---|---|
| Derivative represented by formula 1 | 500 ng |
| Citric acid | 1000 mg |
| Oligosaccharide | 100 g |
| Maesil (Prunus mume) extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

INDUSTRIAL APPLICABILITY

The novel indene derivative of the present invention, the optical isomer of the same, or the pharmaceutically acceptable salts of the same have excellent inhibitory efficiency of receptor-interacting serine/threonine-protein kinase 1 (RIPK1). Therefore, the composition containing the same as an active ingredient can be effectively used as a pharmaceutical composition for preventing or treating retinal disease exemplified by retinitis pigmentosa (RP), Leber congenital amaurosis (LCA), Stargardts disease, Usher syndrome, choroideremia, rod-cone or cone-rod dystrophy, ciliopathy, mitochondrial disorders, progressive retinal atrophy, degenerative retinal diseases, age-related macular degeneration (AMD), wet AMD, dry AMD, geographical atrophy, inherited or acquired macular degeneration, retinal photoreceptor diseases, retinal pigment epithelial diseases, diabetic retinopathy, cystic macular edema, uveitis, retinal detachment, traumatic retinal injury, iatrogenic retinal injury, macular holes, macular capillarectasia, ganglion cell diseases, optic nerve diseases, glaucoma, optic neuropathy, ischemic retinal diseases, retinopathy of prematurity, occlusion of retinal vessels, inherited macroaneurysm, retinal vascular diseases, ophthalmic vascular diseases, glaucomatous retinal neurodegeneration, ischemic optic neuropathy and the like.

What is claimed is:

1. A compound, an optical isomer, or a pharmaceutically acceptable salt of the same, wherein the compound is selected from the group consisting of:
   (1) (4-bromo-7-chlorothieno[2,3-c]pyridine-2-yl)(morpholino)methanone;
   (2) (4-(4-fluorophenyl)thieno[2,3-c]pyridine-2-yl)(morpholino)methanone;
   (3) (4-bromothieno[2,3-c]pyridine-2-yl)(morpholino)methanone;
   (4) (4-(4-fluorophenyl)thieno[2,3-b]pyridine-2-yl)(morpholino)methanone;
   (5) (7-chloro-4-(4-fluorophenyl)thieno[2,3-c]pyridine-2-yl)(morpholino)methanone;
   (7) 4-((4-(4-fluorophenyl)benzo[b]thiophene-2-yl)methyl)morpholine;
   (8) 4-(4-(4-fluorophenyl)benzo[b]thiophene-2-carbonyl)morpholine-3-carboxylic acid;
   (9) (4-(1H-indole-5-yl)benzo[b]thiophene-2-yl)(morpholino)methanone;
   (10) N-(4-(2-(morpholine-4-carbonyl)benzo[b]thiophene-4-yl)phenyl)acetamide;

(14) (5-bromo-1H-benzo[d]imidazole-2-yl)(morpholino)methanone;
(17) (4,6-dimethylbenzo[b]thiophene-2-yl)(morpholino)methanone;
(18) (6,7-dimethylbenzo[b]thiophene-2-yl)(morpholino)methanone;
(19) (6-methoxybenzo[b]thiophene-2-yl)(morpholino)methanone;
(20) N,N-diethyl-2-(morpholine-4-carbonyl)benzo[b]thiophene-4-carboxamide;
(24) (5-methoxy-1H-benzo[d]imidazole-2-yl)(morpholino)methanone;
(27) (6-methylbenzofuran-2-yl)(morpholino)methanone;
(29) (7-bromobenzo[b]thiophene-2-yl)(morpholino)methanone;
(30) (4-(2-fluorophenyl)benzo[b]thiophene-2-yl)(morpholino)methanone;
(31) (4-(biphenyl-4-yl)benzo[b]thiophene-2-yl)(morpholino)methanone;
(32) morpholino(4-p-tolylbenzo[b]thiophene-2-yl)methanone;
(33) 4-(2-(morpholine-4-carbonyl)benzo[b]thiophene-4-yl)benzoic acid;
(34) (4-(4-methoxyphenyl)benzo[b]thiophene-2-yl)(morpholino)methanone;
(35) (4-(4-fluorophenyl)benzo[b]thiophene-2-yl)(pyrrolidine-1-yl)methanone;
(36) (4-(3-fluorophenyl)benzo[b]thiophene-2-yl)(morpholino)methanone;
(37) (4-aminopiperidine-1-yl)(4-(4-fluorophenyl)benzo[b]thiophene-2-yl)methanone hydrochloride;
(38) (4-(4-fluorophenyl)benzo[b]thiophene-2-yl)(piperazine-1-yl)methanone hydrochloride;
(39) (4-(4-fluorophenyl)benzo[b]thiophene-2-yl)(morpholino)methanone;
(40) (5-(4-fluorophenyl)benzo[b]thiophene-2-yl)(morpholino)methanone;
(41) (4-(biphenyl-3-yl)benzo[b]thiophene-2-yl)(morpholino)methanone;
(42) (4-(3-aminophenyl)benzo[b]thiophene-2-yl)(morpholino)methanone;
(43) 4-(2-(morpholine-4-carbonyl)benzo[b]thiophene-4-yl)benzamide;
(44) (4-(4-hydroxyphenyl)benzo[b]thiophene-2-yl)(morpholino)methanone;
(45) morpholino(4-(4-(trifluoromethoxy)phenyl)benzo[b]thiophene-2-yl)methanone;
(46) (4-(4-fluorophenyl)benzo[b]thiophene-2-yl)(oxazolidine-3-yl)ethanone;
(47) (4-(4-fluorophenyl)benzo[b]thiophene-2-yl)(piperidine-1-yl)methanone;
(48) (4-(4-fluorophenyl)benzo[b]thiophene-2-yl)(4-hydroxypiperidine-1-yl)methanone;
(49) (4-(4-fluorophenyl)benzo[b]thiophene-2-yl)(4-methylpiperazine-1-yl)methanone hydrochloride;
(50) (4-(4-(methylthio)phenyl)benzo[b]thiophene-2-yl)(morpholino)methanone;
(51) (4-(4-fluorophenyl)benzo[b]thiophene-2-yl)(thiomorpholino)methanone;
(52) (4-(4-fluorophenyl)benzo[b]thiophene-2-yl)(1,4-oxazepane-4-yl)ethanone;
(53) (7-chloro-4-(4-fluorophenyl)benzo[b]thiophene-2-yl)(morpholino)methanone;
(54) (4-(4-bromophenyl)benzo[b]thiophene-2-yl)(morpholino)methanone;
(55) (4-(6-methoxypyridine-3-yl)benzo[b]thiophene-2-yl)(morpholino)methanone;
(56) (4-(3-fluorobenzyl)benzo[b]thiophene-2-yl)(morpholino)methanone;
(57) (4-(2,4-difluorobenzyl)benzo[b]thiophene-2-yl)(morpholino)methanone;
(58) (4-(2,4-difluorophenylamino)benzo[b]thiophene-2-yl)(morpholino)methanone;
(59) (4-(4-fluorophenoxy)benzo[b]thiophene-2-yl)(morpholino)methanone;
(60) (4-(4-fluorophenethyl)benzo[b]thiophene-2-yl)(morpholino)methanone;
(61) (4-(4-fluorobenzyloxy)benzo[b]thiophene-2-yl)(morpholino)methanone;
(62) (4-(4-fluorobenzylsulfonyl)benzo[b]thiophene-2-yl)(morpholino)methanone;
(63) (4-(2,4-difluorophenyl)benzo[b]thiophene-2-yl)(morpholino)methanone;
(64) methyl 4-(2-(morpholine-4-carbonyl)benzo[b]thiophene-4-yl)benzene sulfiante;
(65) (7-(4-fluorophenyl)benzo[b]thiophene-2-yl)(morpholino)methanone;
(66) (4-(6-fluoropyridine-3-yl)benzo[b]thiophene-2-yl)(morpholino)methanone hydrochloride;
(67) (4-(4-fluorobenzyl)benzo[b]thiophene-2-yl)(morpholino)methanone;
(68) (4-(4-fluorophenylamino)benzo[b]thiophene-2-yl)(morpholino)methanone;
(69) (4-((4-fluorophenyl)(methyl)amino)benzo[b]thiophene-2-yl)(morpholino)methanone;
(70) 4-fluoro-N-(2-(morpholine-4-carbonyl)benzo[b]thiophene-4-yl)benzenesulfonamide;
(71) (4-(4-fluorobenzylthio)benzo[b]thiophene-2-yl)(morpholino)methanone;
(72) 1-methyl-5-(2-(morpholine-4-carbonyl)benzo[b]thiophene-4-yl)-1H-pyrrole-2-carbonitrile;
(73) (4-(1-methyl-1H-pyrazol-4-yl)benzo[b]thiophene-2-yl)(morpholino)methanone;
(74) morpholino(4-(thiophene-2-yl)benzo[b]thiophene-2-yl)methanone;
(75) (4-(furan-3-yl)benzo[b]thiophene-2-yl)(morpholino)methanone; and
(76) morpholino(4-(thiophene-3-yl)benzo[b]thiophene-2-yl)methanone.

2. A pharmaceutical composition for the treatment of retinal disease comprising the compound of claim 1, the optical isomer thereof, or the pharmaceutically acceptable salt of the same as an active ingredient, and a pharmaceutical acceptable carrier.

3. The pharmaceutical composition for the treatment of retinal disease according to claim 2, wherein the compound is characterized by inhibiting receptor-interacting serine/threonine-protein kinase 1.

4. The pharmaceutical composition for the treatment of retinal disease according to claim 2, wherein the retinal disease is selected from the group consisting of retinitis pigmentosa (RP), Leber congenital amaurosis (LCA), Stargardts disease, Usher syndrome, choroideremia, rod-cone or cone-rod dystrophy, ciliopathy, mitochondrial disorders, progressive retinal atrophy, degenerative retinal diseases, age-related macular degeneration (AMD), wet AMD, dry AMD, geographical atrophy, inherited or acquired macular degeneration, retinal photoreceptor diseases, retinal pigment epithelial diseases, diabetic retinopathy, cystic macular edema, uveitis, retinal detachment, traumatic retinal injury, iatrogenic retinal injury, macular holes, macular capillarectasia, ganglion cell diseases, optic nerve diseases, glaucoma, optic neuropathy, ischemic retinal diseases, retinopathy of prematurity, occlusion of retinal vessels, inherited macroaneurysm, retinal vascular diseases, ophthalmic vascular diseases, glaucomatous retinal neurodegeneration, and ischemic optic neuropathy.

5. A method of treating retinal disease in a subject, comprising administering to the subject an effective amount of a compound, an optical isomer, or a pharmaceutically acceptable salt thereof, wherein the compound is selected from the group consisting of:
(1) (4-bromo-7-chlorothieno[2,3-c]pyridine-2-yl)(morpholino)methanone;
(2) (4-(4-fluorophenyl)thieno[2,3-c]pyridine-2-yl)(morpholino)methanone;
(3) (4-bromothieno[2,3-c]pyridine-2-yl)(morpholino)methanone;
(4) (4-(4-fluorophenyl)thieno[2,3-b]pyridine-2-yl)(morpholino)methanone;
(5) (7-chloro-4-(4-fluorophenyl)thieno[2,3-c]pyridine-2-yl)(morpholino)methanone;
(6) morpholino(naphtho[1,2-b]thiophene-2-yl)methanone;
(7) 4-((4-(4-fluorophenyl)benzo[b]thiophene-2-yl)methyl)morpholine;
(8) 4-(4-(4-fluorophenyl)benzo[b]thiophene-2-carbonyl)morpholine-3-carboxylic acid;
(9) (4-(1H-indole-5-yl)benzo[b]thiophene-2-yl)(morpholino)methanone;
(10) N-(4-(2-(morpholine-4-carbonyl)benzo[b]thiophene-4-yl)phenyl)acetamide;
(11) (5-hydroxy-1H-indole-2-yl)(morpholino)methanone;
(12) (5-chloro-1H-indole-2-yl)(morpholino)methanone;
(13) (5-methyl-1H-benzo[d]imidazole-2-yl)(morpholino)methanone;
(14) (5-bromo-1H-benzo[d]imidazole-2-yl)(morpholino)methanone;
(15) benzofuran-2-yl(morpholino)methanone;
(16) (5-bromobenzofuran-2-yl)(morpholino)methanone;
(17) (4,6-dimethylbenzo[b]thiophene-2-yl)(morpholino)methanone;
(18) (6,7-dimethylbenzo[b]thiophene-2-yl)(morpholino)methanone;
(19) (6-methoxybenzo[b]thiophene-2-yl)(morpholino)methanone;
(20) N,N-diethyl-2-(morpholine-4-carbonyl)benzo[b]thiophene-4-carboxamide;
(21) (5-methyl-1H-indole-2-yl)(morpholino)methanone;
(22) (5-methoxy-1H-indole-2-yl)(morpholino)methanone;
(23) (1H-benzo[d]imidazole-2-yl)(morpholino)methanone;
(24) (5-methoxy-1H-benzo[d]imidazole-2-yl)(morpholino)methanone;
(25) (1-methyl-1H-indole-2-yl)(morpholino)methanone;
(26) (5-methoxybenzofuran-2-yl)(morpholino)methanone;
(27) (6-methylbenzofuran-2-yl)(morpholino)methanone;
(28) (5-aminobenzo[b]thiophene-2-yl)(morpholino)methanone;
(29) (7-bromobenzo[b]thiophene-2-yl)(morpholino)methanone;
(30) (4-(2-fluorophenyl)benzo[b]thiophene-2-yl)(morpholino)methanone;
(31) (4-(biphenyl-4-yl)benzo[b]thiophene-2-yl)(morpholino)methanone;
(32) morpholino(4-p-tolylbenzo[b]thiophene-2-yl)methanone;
(33) 4-(2-(morpholine-4-carbonyl)benzo[b]thiophene-4-yl)benzoic acid;
(34) (4-(4-methoxyphenyl)benzo[b]thiophene-2-yl)(morpholino)methanone;
(35) (4-(4-fluorophenyl)benzo[b]thiophene-2-yl)(pyrrolidine-1-yl)methanone;
(36) (4-(3-fluorophenyl)benzo[b]thiophene-2-yl)(morpholino)methanone;
(37) (4-aminopiperidine-1-yl)(4-(4-fluorophenyl)benzo[b]thiophene-2-yl)methanone hydrochloride;
(38) (4-(4-fluorophenyl)benzo[b]thiophene-2-yl)(piperazine-1-yl)methanone hydrochloride;
(39) (4-(4-fluorophenyl)benzo[b]thiophene-2-yl)(morpholino)methanone;
(40) (5-(4-fluorophenyl)benzo[b]thiophene-2-yl)(morpholino)methanone;
(41) (4-(biphenyl-3-yl)benzo[b]thiophene-2-yl)(morpholino)methanone;
(42) (4-(3-aminophenyl)benzo[b]thiophene-2-yl)(morpholino)methanone;
(43) 4-(2-(morpholine-4-carbonyl)benzo[b]thiophene-4-yl)benzamide;
(44) (4-(4-hydroxyphenyl)benzo[b]thiophene-2-yl)(morpholino)methanone;
(45) morpholino(4-(4-(trifluoromethoxy)phenyl)benzo[b]thiophene-2-yl)methanone;
(46) (4-(4-fluorophenyl)benzo[b]thiophene-2-yl)(oxazolidine-3-yl)methanone;
(47) (4-(4-fluorophenyl)benzo[b]thiophene-2-yl)(piperidine-1-yl)methanone;
(48) (4-(4-fluorophenyl)benzo[b]thiophene-2-yl)(4-hydroxypiperidine-1-yl)methanone;
(49) (4-(4-fluorophenyl)benzo[b]thiophene-2-yl)(4-methylpiperazine-1-yl)methanone hydrochloride;
(50) (4-(4-(methylthio)phenyl)benzo[b]thiophene-2-yl)(morpholino)methanone;
(51) (4-(4-fluorophenyl)benzo[b]thiophene-2-yl)(thiomorpholino)methanone;
(52) (4-(4-fluorophenyl)benzo[b]thiophene-2-yl)(1,4-oxazepane-4-yl)methanone;
(53) (7-chloro-4-(4-fluorophenyl)benzo[b]thiophene-2-yl)(morpholino)methanone;
(54) (4-(4-bromophenyl)benzo[b]thiophene-2-yl)(morpholino)methanone;
(55) (4-(6-methoxypyridine-3-yl)benzo[b]thiophene-2-yl)(morpholino)methanone;
(56) (4-(3-fluorobenzyl)benzo[b]thiophene-2-yl)(morpholino)methanone;
(57) (4-(2,4-difluorobenzyl)benzo[b]thiophene-2-yl)(morpholino)methanone;
(58) (4-(2,4-difluorophenylamino)benzo[b]thiophene-2-yl)(morpholino)methanone;
(59) (4-(4-fluorophenoxy)benzo[b]thiophene-2-yl)(morpholino)methanone;
(60) (4-(4-fluorophenethyl)benzo[b]thiophene-2-yl)(morpholino)methanone;
(61) (4-(4-fluorobenzyloxy)benzo[b]thiophene-2-yl)(morpholino)methanone;
(62) (4-(4-fluorobenzylsulfonyl)benzo[b]thiophene-2-yl)(morpholino)methanone;
(63) (4-(2,4-difluorophenyl)benzo[b]thiophene-2-yl)(morpholino)methanone;
(64) methyl 4-(2-(morpholine-4-carbonyl)benzo[b]thiophene-4-yl)benzene sulfiante;
(65) (7-(4-fluorophenyl)benzo[b]thiophene-2-yl)(morpholino)methanone;
(66) (4-(6-fluoropyridine-3-yl)benzo[b]thiophene-2-yl)(morpholino)methanone hydrochloride;

(67) (4-(4-fluorobenzyl)benzo[b]thiophene-2-yl)(morpholino)methanone;
(68) (4-(4-fluorophenylamino)benzo[b]thiophene-2-yl)(morpholino)methanone;
(69) (4-((4-fluorophenyl)(methyl)amino)benzo[b]thiophene-2-yl)(morpholino)methanone;
(70) 4-fluoro-N-(2-(morpholine-4-carbonyl)benzo[b]thiophene-4-yl)benzenesulfonamide;
(71) (4-(4-fluorobenzylthio)benzo[b]thiophene-2-yl)(morpholino)methanone;
(72) 1-methyl-5-(2-(morpholine-4-carbonyl)benzo[b]thiophene-4-yl)-1H-pyrrole-2-carbonitrile;
(73) (4-(1-methyl-1H-pyrazol-4-yl)benzo[b]thiophene-2-yl)(morpholino)methanone;
(74) morpholino(4-(thiophene-2-yl)benzo[b]thiophene-2-yl)methanone;
(75) (4-(furan-3-yl)benzo[b]thiophene-2-yl)(morpholino)methanone; and
(76) morpholino(4-(thiophene-3-yl)benzo[b]thiophene-2-yl)methanone.

6. The method of treating retinal disease according to claim 5, wherein the compound is characterized by inhibiting receptor-interacting serine/threonine-protein kinase 1.

7. The method of treating retinal disease according to claim 5, wherein the retinal disease is selected from the group consisting of retinitis pigmentosa (RP), Leber congenital amaurosis (LCA), Stargardts disease, Usher syndrome, choroideremia, rod-cone or cone-rod dystrophy, ciliopathy, mitochondrial disorders, progressive retinal atrophy, degenerative retinal diseases, age-related macular degeneration (AMD), wet AMD, dry AMD, geographical atrophy, inherited or acquired macular degeneration, retinal photoreceptor diseases, retinal pigment epithelial diseases, diabetic retinopathy, cystic macular edema, uveitis, retinal detachment, traumatic retinal injury, iatrogenic retinal injury, macular holes, macular capillarectasia, ganglion cell diseases, optic nerve diseases, glaucoma, optic neuropathy, ischemic retinal diseases, retinopathy of prematurity, occlusion of retinal vessels, inherited macroaneurysm, retinal vascular diseases, ophthalmic vascular diseases, glaucomatous retinal neurodegeneration, and ischemic optic neuropathy.

* * * * *

UNITED STATES PATENT AND TRADEMARK OFFICE
CERTIFICATE OF CORRECTION

Page 1 of 1

PATENT NO. : 10,501,473 B2
APPLICATION NO. : 15/417724
DATED : December 10, 2019
INVENTOR(S) : Eunhee Kim et al.

It is certified that error appears in the above-identified patent and that said Letters Patent is hereby corrected as shown below:

In the Claims

Claim 1, Lines 48 and 49, delete:
"(46) (4-(4-fluorophenyl)benzo[b]thiophene-2-yl)(oxazolidine-3-yl)ethanone;"
And add:
--(46) (4-(4-fluorophenyl)benzo[b]thiophene-2-yl)(oxazolidine-3-yl)methanone;--

Claim 1, Lines 60 and 61, delete:
"(52) (4-(4-fluorophenyl)benzo[b]thiophene-2-yl)(1,4-oxazepane-4-yl) ethanone;"
And add:
--(52) (4-(4-fluorophenyl)benzo[b]thiophene-2-yl)(1,4-oxazepane-4-yl) methanone;--

Signed and Sealed this
Fourth Day of February, 2020

Andrei Iancu
*Director of the United States Patent and Trademark Office*